(12) United States Patent
Smith et al.

(10) Patent No.: US 9,399,802 B2
(45) Date of Patent: *Jul. 26, 2016

(54) METHODS AND MATERIALS FOR DETECTING CONTAMINATED FOOD PRODUCTS

(71) Applicant: Cascade Biosystems, Inc., Colfax, WI (US)

(72) Inventors: Kenneth D. Smith, Colfax, WI (US); Nina Yazvenko, Vancouver, WA (US); Mariya Smit, Vancouver, WA (US)

(73) Assignee: Cascade Biosystems, Inc., Colfax, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/841,015

(22) Filed: Aug. 31, 2015

(65) Prior Publication Data

US 2015/0361484 A1    Dec. 17, 2015

Related U.S. Application Data

(63) Continuation of application No. 14/090,167, filed on Nov. 26, 2013, now Pat. No. 9,150,932, which is a continuation of application No. 13/027,980, filed on Feb. 15, 2011, now Pat. No. 8,623,616.

(60) Provisional application No. 61/304,781, filed on Feb. 15, 2010.

(51) Int. Cl.
*C12Q 1/68* (2006.01)

(52) U.S. Cl.
CPC ............... *C12Q 1/689* (2013.01); *C12Q 1/683* (2013.01); *C12Q 2600/158* (2013.01)

(58) Field of Classification Search
CPC ............ C12Q 1/686; C12Q 2527/137; C12Q 2565/518; C09K 3/00; C12P 19/34
USPC ....................................................... 435/91.2
See application file for complete search history.

(56) References Cited

U.S. PATENT DOCUMENTS

| | | | |
|---|---|---|---|
| 4,699,876 A | 10/1987 | Libeskind | |
| 4,775,619 A | 10/1988 | Urdea | |
| 5,102,784 A | 4/1992 | George, Jr. | |
| 5,403,711 A | 4/1995 | Walder et al. | |
| 5,679,510 A | 10/1997 | Ray et al. | |
| 5,795,718 A | 8/1998 | Eisenbeis | |
| 5,858,665 A | 1/1999 | Hepp et al. | |
| 6,110,677 A | 8/2000 | Western et al. | |
| 6,114,117 A | 9/2000 | Hepp et al. | |
| 6,156,953 A | 12/2000 | Preuss et al. | |
| 6,492,120 B1 | 12/2002 | Galvan et al. | |
| 6,825,010 B2 | 11/2004 | Spier et al. | |
| 7,524,629 B2 | 4/2009 | Olek et al. | |
| 8,278,048 B2 * | 10/2012 | Smith | C12Q 1/682 435/6.11 |
| 8,470,533 B2 | 6/2013 | Smith et al. | |
| 8,551,701 B2 | 10/2013 | Smith et al. | |
| 8,597,886 B2 | 12/2013 | Smith et al. | |
| 8,623,616 B2 * | 1/2014 | Smith | C12Q 1/683 435/6.11 |
| 8,632,974 B2 * | 1/2014 | Smith | C12Q 1/682 435/6.11 |
| 8,865,407 B2 * | 10/2014 | Smith | C12Q 1/682 435/196 |
| 9,150,921 B2 | 10/2015 | Smith et al. | |
| 9,150,932 B2 | 10/2015 | Smith et al. | |
| 9,150,935 B2 | 10/2015 | Smith et al. | |
| 2002/0015951 A1 | 2/2002 | Bader et al. | |
| 2002/0123620 A1 | 9/2002 | Danenberg | |
| 2003/0124594 A1 * | 7/2003 | Church | C07K 1/047 435/6.11 |
| 2003/0235837 A1 | 12/2003 | Keim et al. | |
| 2005/0003390 A1 | 1/2005 | Axenovich et al. | |
| 2006/0240431 A1 | 10/2006 | Fu | |
| 2007/0231800 A1 | 10/2007 | Roberts et al. | |
| 2008/0021205 A1 | 1/2008 | Blau et al. | |
| 2009/0263809 A1 | 10/2009 | Roberton et al. | |
| 2013/0344578 A1 | 12/2013 | Smith et al. | |
| 2015/0004609 A1 | 1/2015 | Smith et al. | |
| 2015/0225769 A1 | 8/2015 | Smith et al. | |
| 2015/0361485 A1 | 12/2015 | Smith | |
| 2015/0361501 A1 | 12/2015 | Smith | |

FOREIGN PATENT DOCUMENTS

| | | |
|---|---|---|
| WO | WO 98/04739 | 2/1998 |
| WO | WO 98/19168 | 5/1998 |
| WO | WO 02/059359 | 8/2002 |
| WO | WO 2004/101788 | 11/2004 |
| WO | WO 2004/108897 | 12/2004 |
| WO | WO 2010/019414 | 2/2010 |

OTHER PUBLICATIONS

Albretsen et al., "Applications of magnetic beads with covalently attached oligonucleotides in hybridization: isolation and detection of specific measles virus mRNA from a crude cell lysate," Anal. Biochem., 1990, 189(1):40-50.

Beaucage et al., "Deoxynucleoside phosphoramidites—a new class of key intermediates for deoxypolynucleotide synthesis," Tet. Let., 1981, 22(20):1859-1862.

Bekkaoui et al., "Cycling probe technology with RNase H attached to an oligonucleotide," BioTechniques, Feb. 1996, 20:240-248.

Black, Microbiology. Principles and Applications, Third Edition, 1996, pp. 144-148.

Chan et al., "Quantitative Analysis of Circulating Methylated DNA as a Biomarker for Hepatocellular Carcinoma," Clin. Chem., Jul. 24, 2008, 54:1664-1672.

Di Gioia et al., "Quantitative evaluation of RASSF1A methylation in the non-lesional, regenerative and neoplastic liver," BMC Cancer, 2006, 6:89, 12 pages.

(Continued)

*Primary Examiner* — Cynthia B Wilder
(74) *Attorney, Agent, or Firm* — Fish & Richardson P.C.

(57) ABSTRACT

This document provides methods and materials for detecting contaminated food products. For example, methods and materials for using an enzymatic amplification cascade of restriction endonucleases to detect nucleic acid of a microorganism or virus (e.g., a pathogen) within a sample (e.g., food product sample) being tested, thereby assessing a food product for possible contamination are provided.

20 Claims, 15 Drawing Sheets

(56) References Cited

OTHER PUBLICATIONS

Dill et al., "Immunoassays based on electrochemical detection using microelectrode arrays," Biosensors and Bioelectronics, 2004, 20:736-742.
Fischer et al., "Prognostic significance of RASSF1A promoter methylation on survival of non-small cell lung cancer patients treated with gemcitabine," Lung Cancer, 2007, 56:115-123.
Froehler et al., "Synthesis of DNA via deoxynucleoside H-phosphonate intermediates," Nucl. Acid Res., 1986, 14:5399-5407.
Gaffney et al., "Large-scale oligonucleotides synthesis by the H-Phosphonate method," Tet. Let., 1988, 29:2619-2622.
Garegg et al., "Nucleoside H-phosphonates III. Chemical synthesis of oligodeoxyribonucleotides by the hydrogenphosphonate approach," Tet. Let., 1986, 27:4051-4054.
Garegg et al., "Nucleoside H-phosphonates IV. Automated solid phase synthesis of oligoribonucleotides by the hydrogenphosphonate approach," Tet. Let., 27:4055-4058 (1986).
GenBank® Accession No. AJ536123; GenBank® GI No. 40643613, Nov. 14, 2006, 3 pages.
GenBank® Accession No. AJ536131; GenBank® GI No. 40643629, Nov. 14, 2006, 3 pages.
GenBank® Accession No. AJ536135; GenBank® GI No. 40643637, Nov. 14, 2006, 4 pages.
GenBank® Accession No. BA000007 GenBank® GI No. 47118301, Jan. 18, 2008, p. 1 of 157.
GenBank® Accession No. CP000052; GenBank® GI No. 761681535 Mar. 2010, 4 pages.
GenBank® Accession No. NC_002952 GenBank® GI No. 49482253, Jan. 22, 2012, p. 1 of 109.
GenBank® Accession No. NC_000962; GenBank® GI No. 5711668119 Jan. 2012, 2 pages.
GenBank® Accession No. NC_001803; GenBank® GI No. 9629367, Nov. 22, 2009, 8 pages.
GenBank® Accession No. NC_002016; GenBank® GI No. 8486122, Jul. 16, 2008, 2 pages.
GenBank® Accession No. NC_002695; GenBank® GI No. 15829254 at 1267936-1268205, Jan. 25, 2012, p. 1 of 178.
GenBank® Accession No. NC_002946; GenBank® GI No. 59800473, Jan. 20, 2012, p. 1 of 285 pages.
GenBank® Accession No. NC_003198; GenBank® GI No. 16758993, Jan. 20, 2012, 1 page.
GenBank® Accession No. NC_003210; GenBank® GI No. 16802048, Jan. 20, 2012, 1 page.
GenBank® Accession No. NC_003266; GenBank® GI No. 51527264, May 6, 2009, p. 1 of 21 pages.
GenBank® Accession No. NC_003485; GenBank® GI No. 19745201, Jan. 20, 2012, p. 1 of 350.
GenBank® Accession No. NC_003912; GenBank® GI No. 57236892, Aug. 1, 2011, p. 1 of 337.
GenBank® Accession No. NC_004603; GenBank® GI No. 28896774, Jan. 20, 2012, p. 1 of 441.
GenBank® Accession No. NC_007607; GenBank® GI No. 82524407, Apr. 1, 2010, p. 1 of 92.
GenBank® Accession No. NC_008533; GenBank® GI No. 116515308, Jan. 26, 2012, p. 1 of 383.
GenBank® Accession No. NC_010741; GenBank® GI No. 189025236, May 2, 2011, p. 1 of 174.
GenBank® Accession No. NC_013450; GenBank® GI No. 269201690, Feb. 14, 2012, p. 1 of 404.
GenBank® Accession No. NM_020469; GenBank® GI No. 58331215, Apr. 12, 2012, 4 pages.
GenBank® Accession No. X01712.1; GenBank® GI No. 59898, Apr. 18, 2005, 2 pages.
Guerini et al., "Rapid enrichment strategy for isolation of Listeria from bovine hide, carcass, and meat samples," J. Food Prot., 2007, 70(1):53-57.
He et al., "Selective and homogeneous fluorescent DNA detection by target-induced strand displacement using cationic conjugated polyelectrolytes," Anal. Chem., 2008, 80(6):2239-2243.
Jin et al., "Multiplexed bead-based mesofluidic system for detection of food-borne pathogenic bacteria," Appl. Environ. Microbiol., 2009, 75:6647-6654.
Kanagawa, "Bias and artifacts in multitemplate polymerase chain reactions (PCR)," J Biosci Bioeng., 2003, 96(4):317-323.
Kiesling et al., "Sequence specific detection of DNA using nicking endonuclease signal amplification (NESA)," Nucl Acid Res, 2007 35(18):e117.
Liu et al., "Electrochemical detection of hepatitis C virus based on site-specific DNA cleavage of BamHI endonuclease," Chem Commun (Camb), Apr. 7, 2009, (13):1635-1637.
Maruya et al., "Differential methylation status of tumor-associated genes in head and neck squamous carcinoma: incidence and potential implications," Clin. Cancer Res., 2004, 10:3825-3830.
McClelland et al., Effect of site-specific modification on restriction endonucleases and DNA modification methyltransferases, Nucleic Acids Res., 1994, 22:3640-3659.
Nam et al., "Evaluation of universal pre-enrichment broth for isolation of *Salmonella* spp., *Escherichia coli* O157:H7, and Listeria monocytogenes from dairy farm environmental samples," Foodborne Pathog. Dis., 2004, 1(1):37-44.
O'Mahony and Papkovsky, "Rapid high throughput assessment of aerobic bacteria in complex samples by fluorescence-based oxygen respirometry," Applied and Environmental Microbiology, 2006, 72:1279-1287.
O'Mahony et al., "Analysis of total aerobic viable counts in samples of raw meat using fluorescence-based probe and oxygen consumption assay," Food Control, 2009, 20:129-135.
Pei, D. et. al., "Site-specific cleavage of duplex DNA by a semisynthetic nuclease via triple-helix formation," Proceedings of the National Academy of Sciences of the United States of America, vol. 87, No. 24, (1990), pp. 9858-9862.
Perelle et al., "A LightCycler real-time PCR hybridization probe assay for detecting food-borne thermophilic Campylobacter," Mol. Cell. Probes, 2004, 18:321-327.
Polz and Cavanaugh, "Bias in Template-to-Product Ratios in Multitemplate PCR," Applied and Environmental Microbiology, 1998, 64(10):3724-3730.
Rykova et al., "Methylation-Based Analysis of Circulating DNA for Breast Tumor Screening," Ann. N.Y. Acad. Sci., 2008, 1137:232-235.
Schrank et al., "Influence of enrichment media and application of a PCR based method to detect *Salmonella* in poultry industry products and clinical samples," Vet. Micro., 2001, 82:45-53.
Sipos et al., "Effect of primer mismatch, annealing temperature and PCR cycle number on 16S rRNA gene-targeting bacterial community analysis," FEMS Microbiol Ecol., 2007, 60(2):341-350.
Sud'ina et al., "Affinity Modification of the Restriction Endonuclease SsoII by 2'-Aldehyde-Containing Double Stranded DNAs," Biochemistry (Moscow), vol. 70, No. 8, 2005, pp. 941-947.
Sunami et al., "Analysis of methylated circulating DNA in cancer patients' blood," Methods Mol. Biol., 2009, 507:349-356.
Szyf, "Targeting DNA methylation in cancer," Ageing Res. Rev., 2003, 2(3):299-328.
Urdea, "Synthesis and characterization of branched DNA (BDNA) for the direct and quantitative detection of CMV, HBV, HCV, and HIV," Clinical Chemistry, 1993, 39(4):725-726.
Wang et al., "Human thiopurine S-methyltransferase pharmacogenetics: Variant allozyme misfolding and aggresome formation," Proc. Natl. Acad. Sci. USA, 2005, 102(26):9394-9399, Published online before print Jun. 20, 2005.
Wang et al., "Identification of epigenetic aberrant promoter methylation of RASSF1A in serum DNA and its clinicopathological significance in lung cancer," Lung Cancer, 2007, 56:289-294.
Weisenberger et al., "DNA methylation analysis by digital bisulfate genomic sequencing and digital MethyLight," Nucl Acid Res., 2008, 36(14):4689-4698.
Widschwendter et al., "Epigenotyping in peripheral blood cell DNA and breast cancer risk: a proof of principle study," PLoS One, 2008, 3(7):e2656.

(56) References Cited

OTHER PUBLICATIONS

Yeo et al., "High frequency of promoter hypermethylation of RASSF1A in tumorous and non-tumorous tissue of breast cancer," Pathology, 2005, 37:125-130.
Zhang et al., "Genetic diversity of intimin genes of attaching and effacing *Escherichia coli* strains," J. Clin. Microbiol., 2002, 40:4486-4492.
European Patent Application No. 09807076.6, Communication pursuant to Article 94(3) EPC, mailed Mar. 21, 2012, 3 pages.
European Search Report for App. No. 09807076.6, mailed Sep. 7, 2011, 5 pages.
International Preliminary Report on Patentability for PCT/US2011/024908, mailed Aug. 30, 2012, 11 pages.
International Preliminary Report on Patentability for PCT/US2011/024912, mailed Aug. 30, 2012, 11 pages.
International Preliminary Report on Patentability for PCT/US2011/024913, mailed Aug. 30, 2012, 11 pages.
International Preliminary Report on Patentability for PCT/US2011/024916, mailed Aug. 30, 2012, 11 pages.
International Preliminary Report on Patentability PCT/US2009/052716, issued Feb. 15, 2011, 5 pages.
International Search Report and Written Opinion of the International Searching Authority in PCT/US2009/052716, mailed May 3, 2010, 7 pages.
International Search Report and Written Opinion of the International Searching Authority, PCT/US2011/024908, mailed Apr. 15, 2011, 13 pages.
International Search Report and Written Opinion of the International Searching Authority, PCT/US2011/024912, mailed Sep. 29, 2011, 18 pages.
International Search Report and Written Opinion of the International Searching Authority, PCT/US2011/024913, mailed Apr. 15, 2011, 14 pages.
International Search Report and Written Opinion of the International Searching Authority, PCT/US2011/024916, mailed Oct. 4, 2011, 15 pages.
Invitation to Pay Additional Fees and, Where Applicable, Protest Fee, PCT/US2009/052716, mailed Mar. 8, 2010, 7 pages.
U.S. Appl. No. 12/535,017, Office Action, mailed Feb. 24, 2012, 14 pages.
U.S. Appl. No. 13/027,887, Office Action, mailed Apr. 24, 2012, 28 pages.

\* cited by examiner

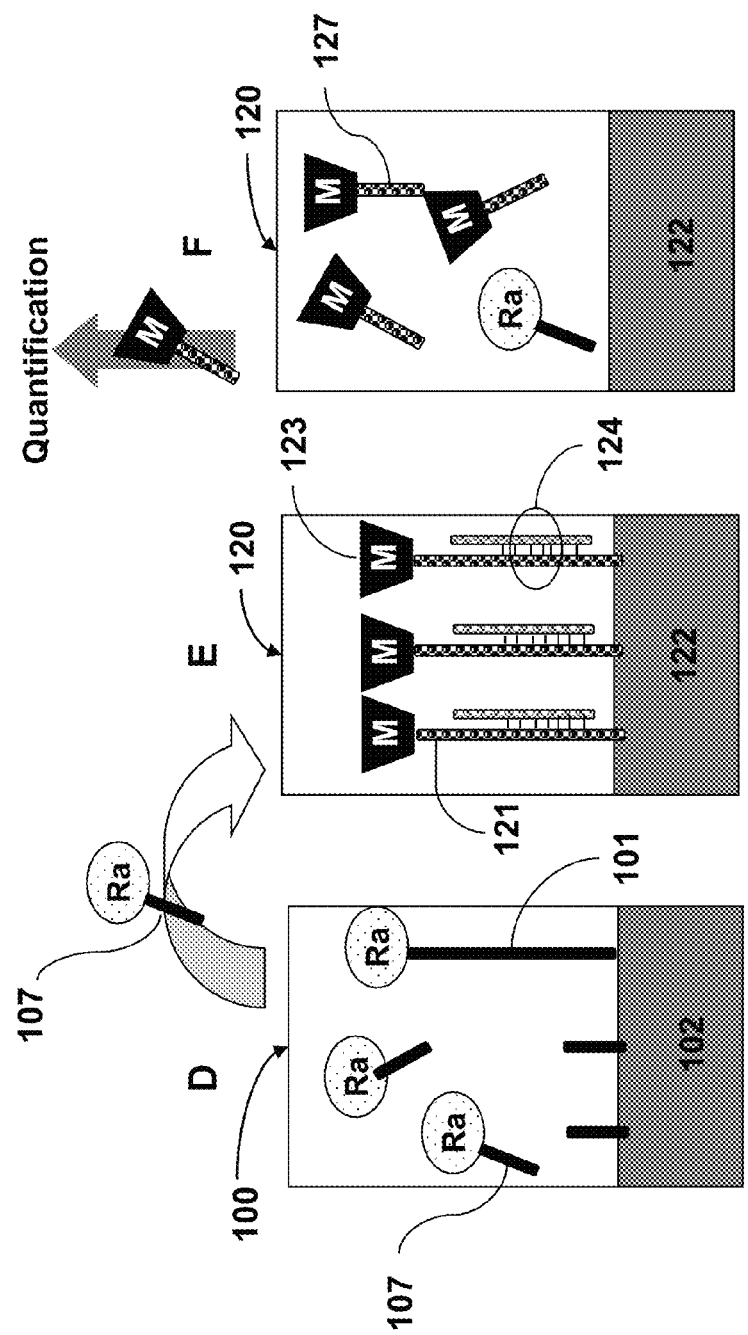

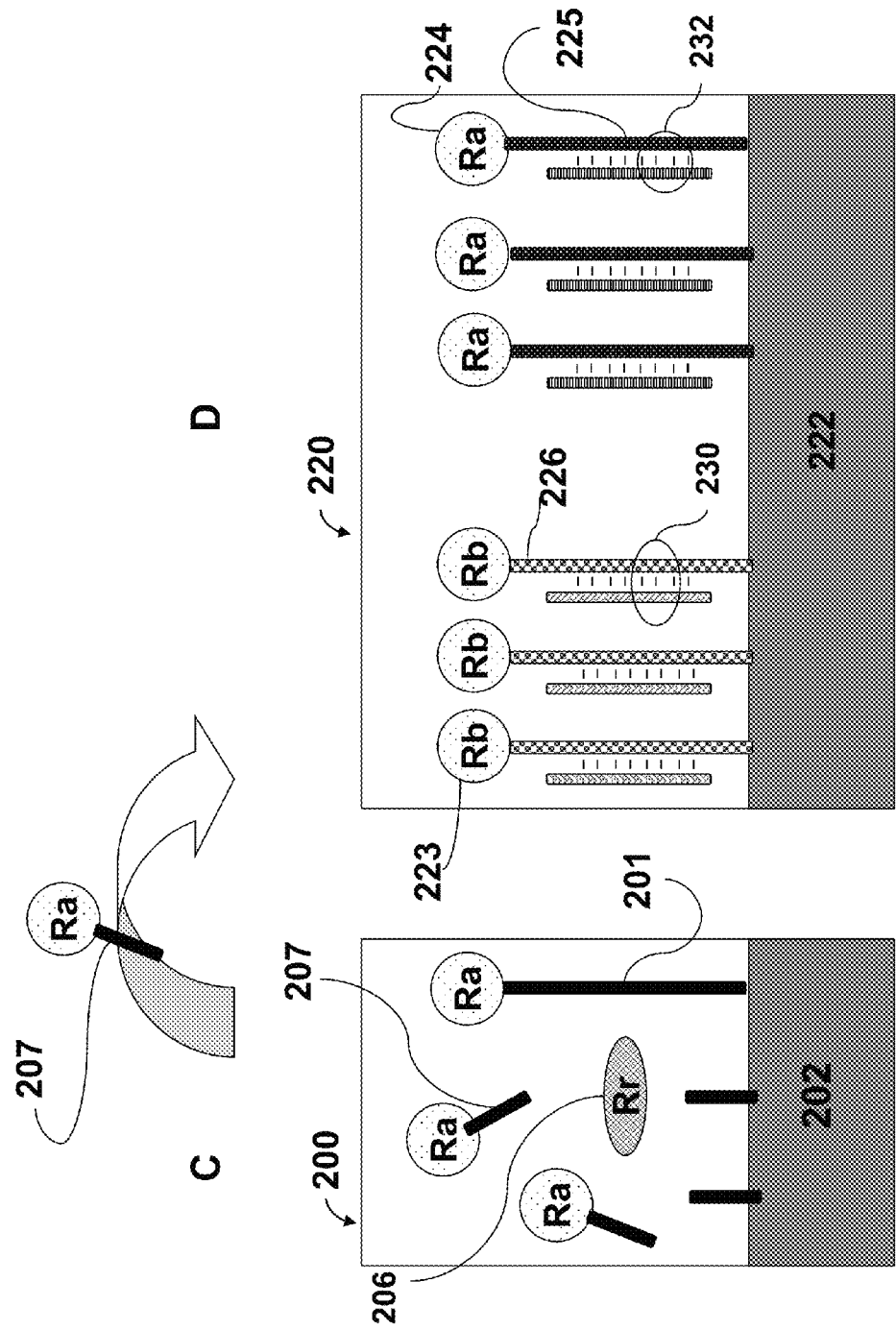
Figure 3 con't

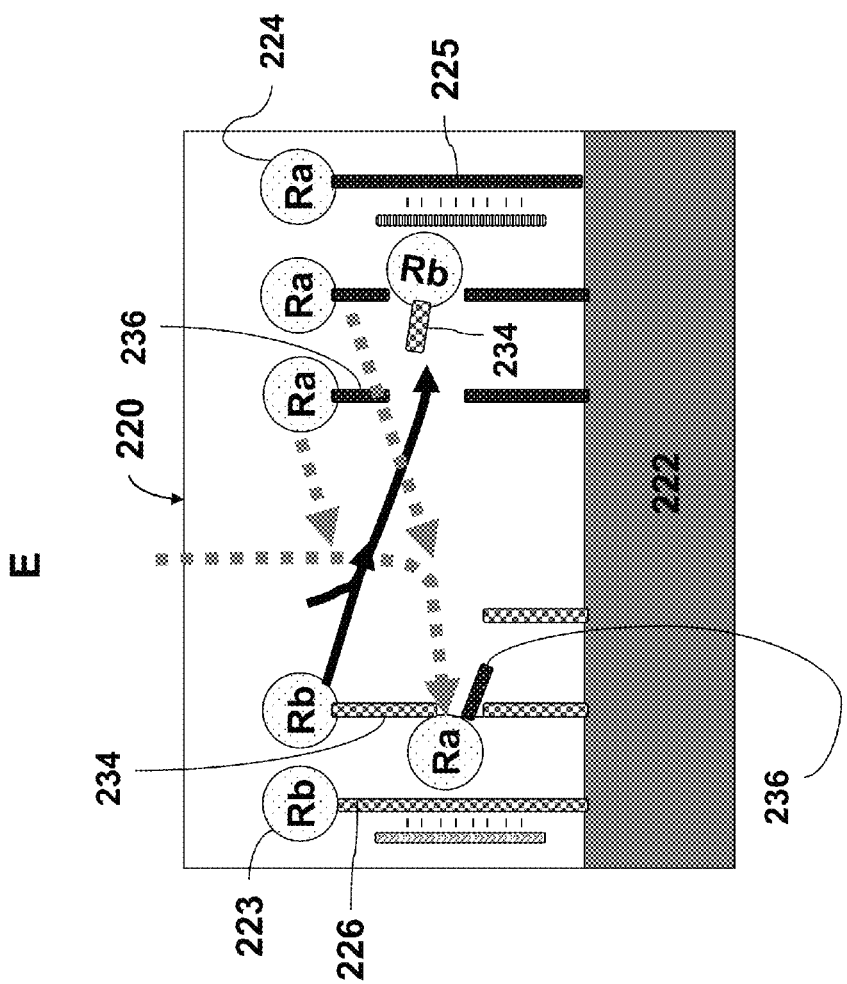
Figure 3 con't

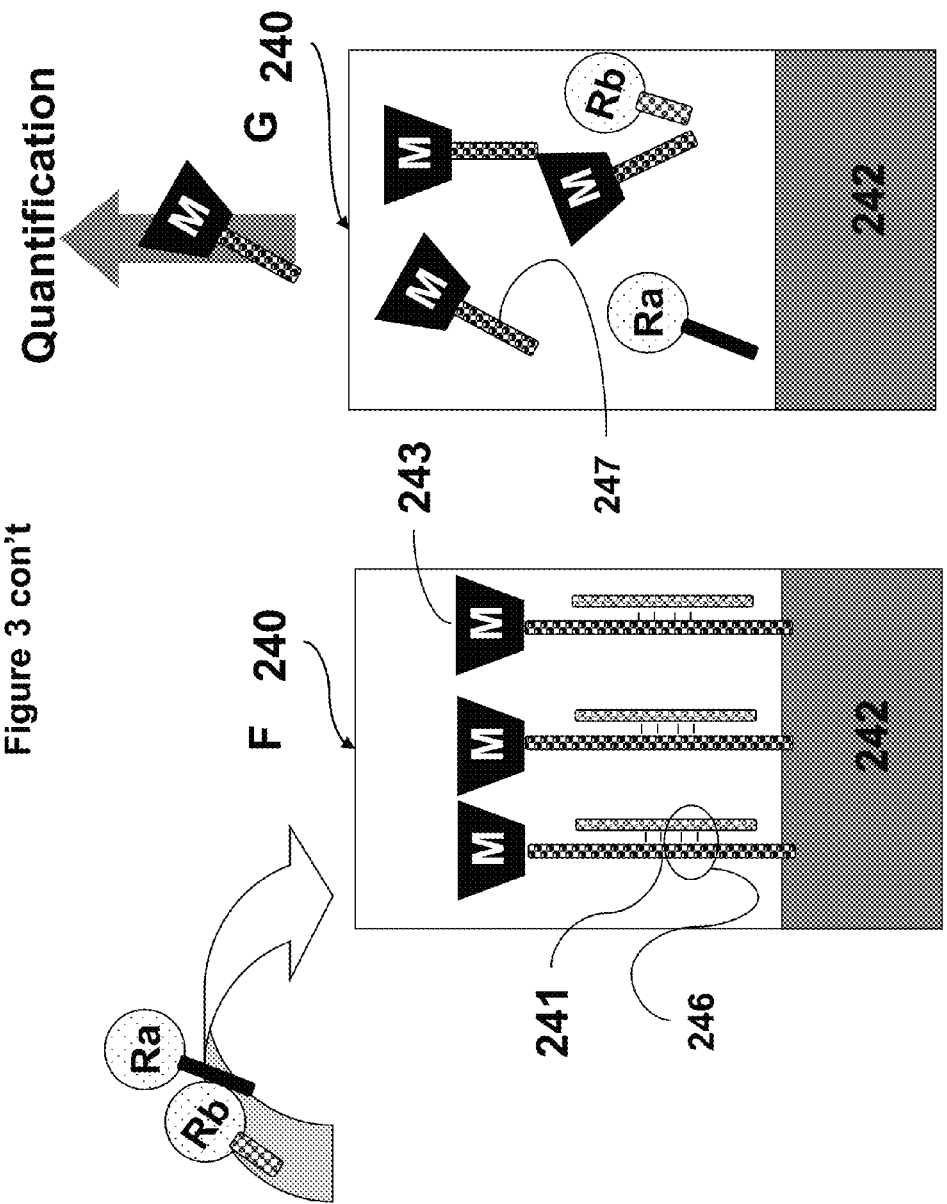

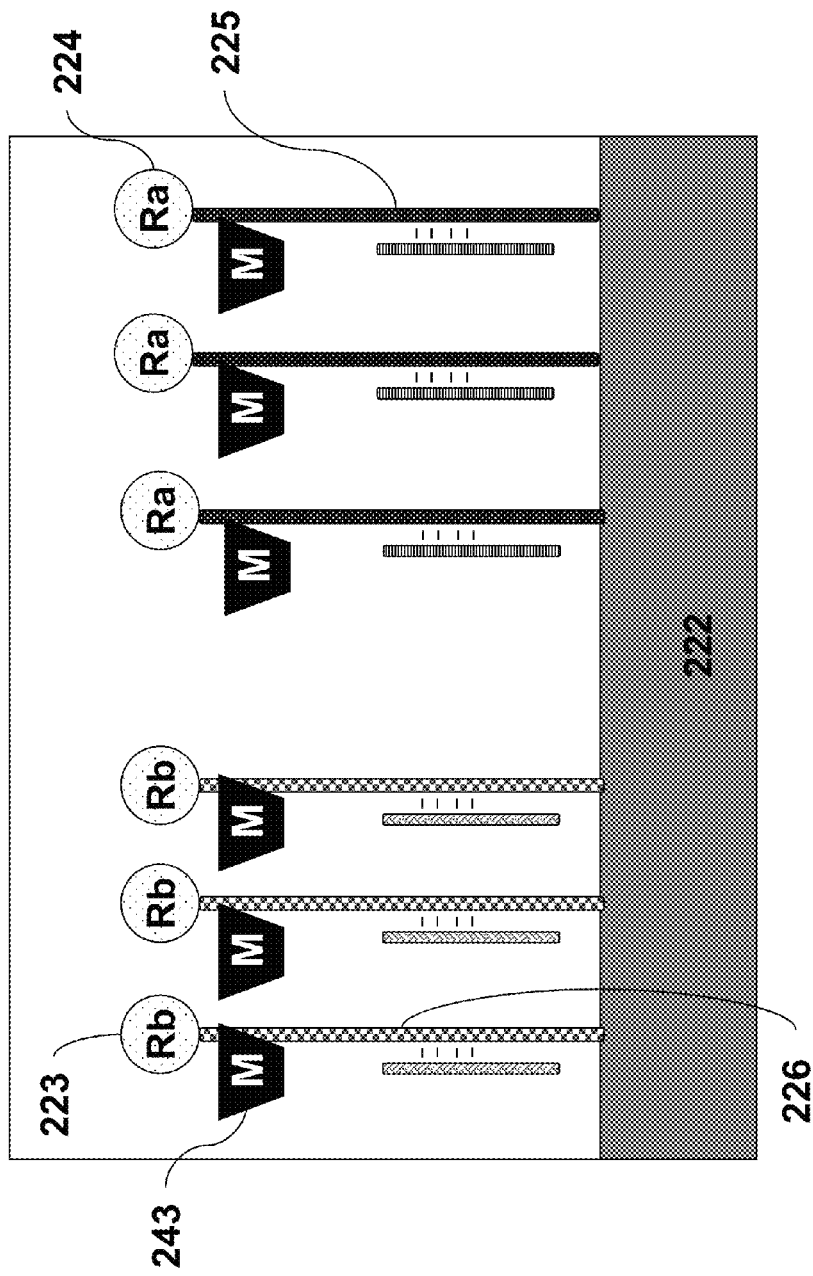

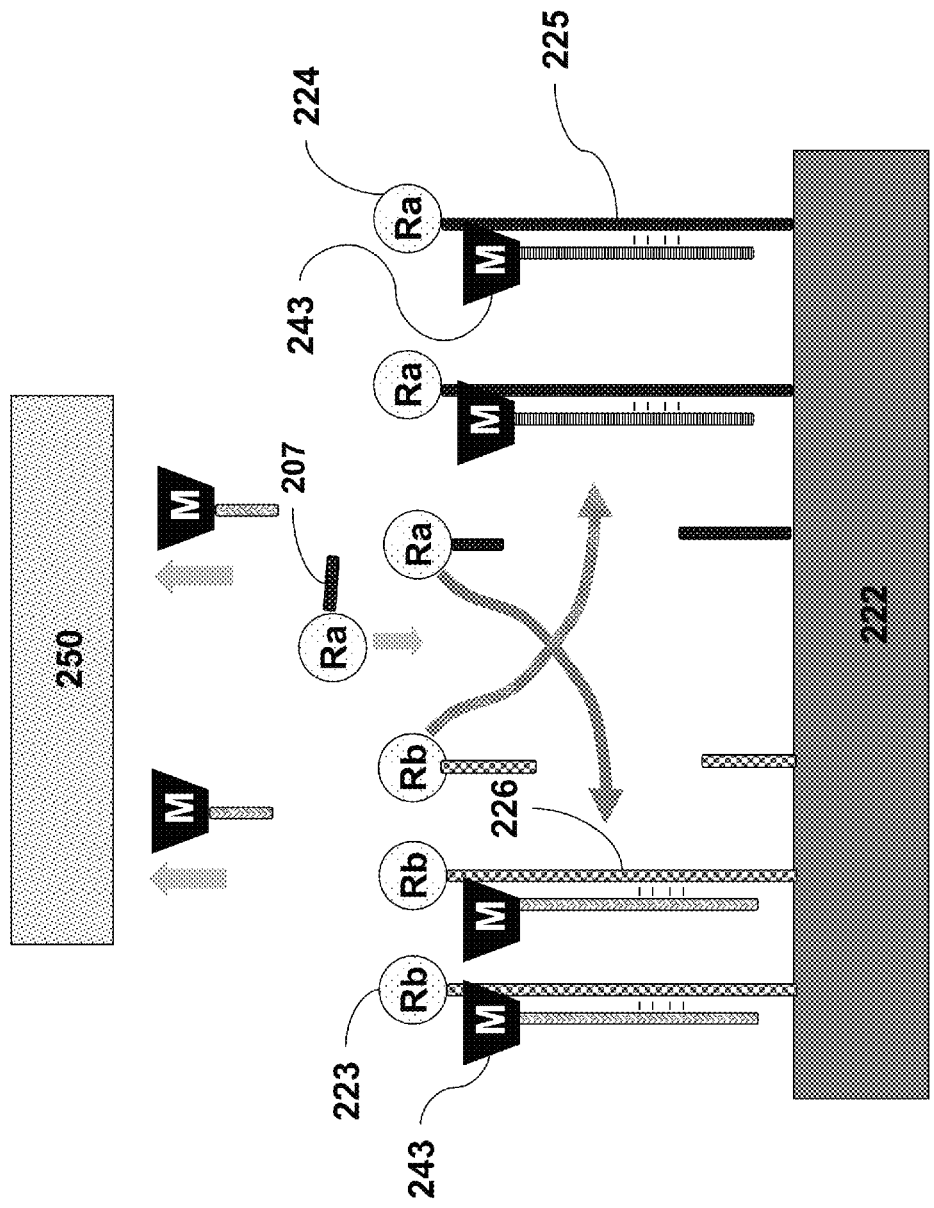

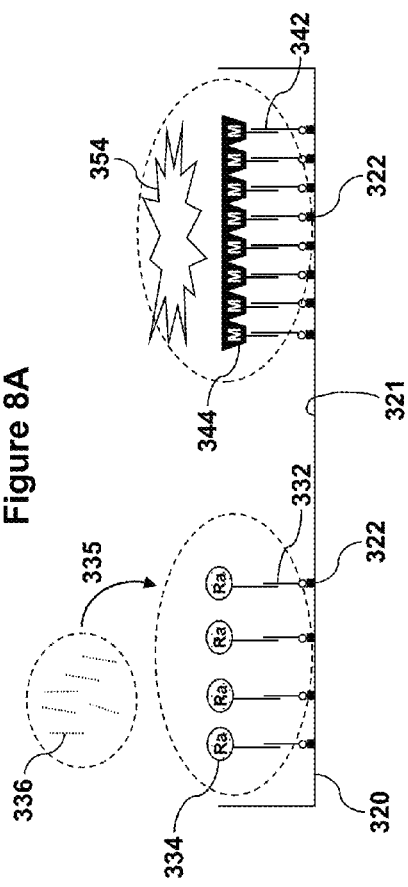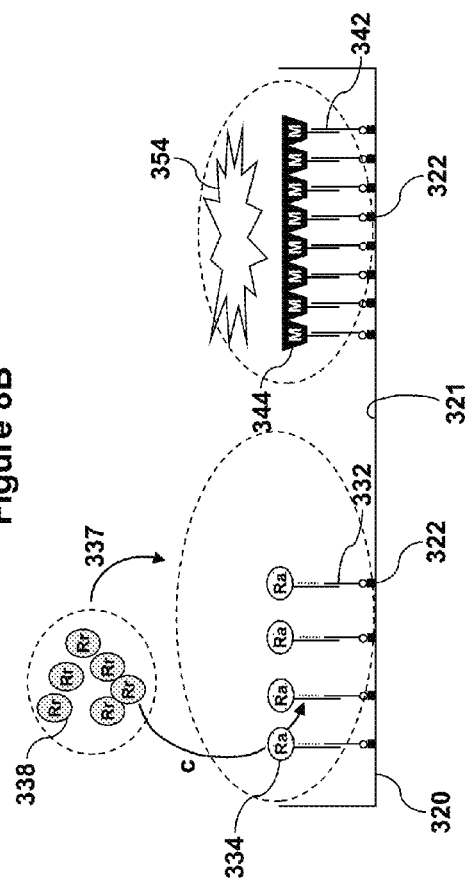

```
                        SEQUENCE LISTING

<160> NUMBER OF SEQ ID NOS: 31

<210> SEQ ID NO 1
<211> LENGTH: 30
<212> TYPE: DNA
<213> ORGANISM: Artificial Sequence
<220> FEATURE:
<223> OTHER INFORMATION: thiol and biotin containing nucleic acid

<400> SEQUENCE: 1
ggtagtgcga aatgccattg ctagttgttt                                        30

<210> SEQ ID NO 2
<211> LENGTH: 21
<212> TYPE: DNA
<213> ORGANISM: Artificial Sequence
<220> FEATURE:
<223> OTHER INFORMATION: partial complement of SEQ ID NO:1

<400> SEQUENCE: 2
aaacaactag caatggcatt t                                                 21

<210> SEQ ID NO 3
<211> LENGTH: 40
<212> TYPE: DNA
<213> ORGANISM: Escherichia coli

<400> SEQUENCE: 3
acagtcattc ctgtcaactg agcactttgc agtaacggtt                             40

<210> SEQ ID NO 4
<211> LENGTH: 36
<212> TYPE: DNA
<213> ORGANISM: Artificial Sequence
<220> FEATURE:
<223> OTHER INFORMATION: nucleic acid containing cleavage site

<400> SEQUENCE: 4
cattgctagt tgtttccatg gggtagtgcg aaatgc                                 36

<210> SEQ ID NO 5
<211> LENGTH: 36
<212> TYPE: DNA
<213> ORGANISM: Artificial Sequence
<220> FEATURE:
<223> OTHER INFORMATION: partial complement of SEQ ID NO:4

<400> SEQUENCE: 5
gcatttcgca ctaccccatg gaaacaacta gcaatg                                 36

<210> SEQ ID NO 6
<211> LENGTH: 38
<212> TYPE: DNA
<213> ORGANISM: Salmonella enterica

<400> SEQUENCE: 6
```
gctggctttc cctttccagt acgcttcgcc gttcgcgc                                   38

<210> SEQ ID NO 7
<211> LENGTH: 40
<212> TYPE: DNA
<213> ORGANISM: Listeria monocytogenes

<400> SEQUENCE: 7
ctatgaaacg tattgaagaa tcgccaatcg aaaaattagt                                 40

<210> SEQ ID NO 8
<211> LENGTH: 40
<212> TYPE: DNA
<213> ORGANISM: Escherichia coli

<400> SEQUENCE: 8
gcaaaagaca ttatggatgc tggcaaactg gtcaccgacg                                 40

<210> SEQ ID NO 9
<211> LENGTH: 40
<212> TYPE: DNA
<213> ORGANISM: Escherichia coli

<400> SEQUENCE: 9
gcaaaagaca ttatggatgc tggcaaattg gtcaccgacg                                 40

<210> SEQ ID NO 10
<211> LENGTH: 40
<212> TYPE: DNA
<213> ORGANISM: Escherichia coli

<400> SEQUENCE: 10
gagaagaaga gactgaagat tccatctgtt ggtaaataat                                 40

<210> SEQ ID NO 11
<211> LENGTH: 40
<212> TYPE: DNA
<213> ORGANISM: Escherichia coli

<400> SEQUENCE: 11
gagaagaaga gactgaagat tccatctgtt agtaaataat                                 40

<210> SEQ ID NO 12
<211> LENGTH: 40
<212> TYPE: DNA
<213> ORGANISM: Escherichia coli

<400> SEQUENCE: 12
acagtcattc ctgtcaactg agcactttgc agtaacggtt                                 40

<210> SEQ ID NO 13
<211> LENGTH: 40
<212> TYPE: DNA
<213> ORGANISM: Escherichia coli

<400> SEQUENCE: 13
acagtcattc ctgtcagctg agcactttgc agtaacggtt                                 40

<210> SEQ ID NO 14
<211> LENGTH: 40
<212> TYPE: DNA
<213> ORGANISM: Escherichia coli

<400> SEQUENCE: 14
ttgttacggt cattcctgtt aactgtgcac tttgtaacaa          40

<210> SEQ ID NO 15
<211> LENGTH: 40
<212> TYPE: DNA
<213> ORGANISM: Escherichia coli

<400> SEQUENCE: 15
ttgtgactgt cattcctgtt aactgtgcac tttgcagtag          40

<210> SEQ ID NO 16
<211> LENGTH: 40
<212> TYPE: DNA
<213> ORGANISM: Escherichia coli

<400> SEQUENCE: 16
tcaaagttat taccactctg cagattaacc tctgccgttc          40

<210> SEQ ID NO 17
<211> LENGTH: 40
<212> TYPE: DNA
<213> ORGANISM: Escherichia coli

<400> SEQUENCE: 17
tcaaagttat caccactctg cagattaacc tctgccgttc          40

<210> SEQ ID NO 18
<211> LENGTH: 40
<212> TYPE: DNA
<213> ORGANISM: Escherichia coli

<400> SEQUENCE: 18
aatttcctca ccgggagtta acaatggcgt aacaaatttc          40

<210> SEQ ID NO 19
<211> LENGTH: 38
<212> TYPE: DNA
<213> ORGANISM: Salmonella enterica

<400> SEQUENCE: 19
gctggctttc cctttccagt acgcttcgcc gttcgcgc            38

<210> SEQ ID NO 20
<211> LENGTH: 40
<212> TYPE: DNA
<213> ORGANISM: Listeria monocytogenes

<400> SEQUENCE: 20
ctatgaaacg tattgaagaa tcgccaatcg aaaaattagt          40

<210> SEQ ID NO 21
<211> LENGTH: 40
<212> TYPE: DNA
<213> ORGANISM: Thermophylic campylobacter

<400> SEQUENCE: 21
ttccctactc aacttgtgtt aagcaggagt atagagtatt          40

<210> SEQ ID NO 22
<211> LENGTH: 40
<212> TYPE: DNA
<213> ORGANISM: Vibrio parahaemolyticus

<400> SEQUENCE: 22
gctcaatgga caactcgata tcggagtgat cagctgtgac    40

<210> SEQ ID NO 23
<211> LENGTH: 40
<212> TYPE: DNA
<213> ORGANISM: Staphylococcus aureus

<400> SEQUENCE: 23
tgatctagcg aaagcaagat atcacaaaat cgtcattatg    40

<210> SEQ ID NO 24
<211> LENGTH: 40
<212> TYPE: DNA
<213> ORGANISM: Campylobacter jejuni

<400> SEQUENCE: 24
agattaggta aagtggttga tatcttggaa actggagctt    40

<210> SEQ ID NO 25
<211> LENGTH: 40
<212> TYPE: DNA
<213> ORGANISM: Shigella dysenteriae

<400> SEQUENCE: 25
tcctccggca gaagcagaaa aagcttatta tgcttccatc    40

<210> SEQ ID NO 26
<211> LENGTH: 40
<212> TYPE: DNA
<213> ORGANISM: Vibrio parahaemolyticus

<400> SEQUENCE: 26
gctcaatgga caactcgata tcggagtgat cagctgtgac    40

<210> SEQ ID NO 27
<211> LENGTH: 140
<212> TYPE: DNA
<213> ORGANISM: Escherichia coli

<400> SEQUENCE: 27
ggggaaaggg actcaggctc agttcatcat ggagaaatat ggtattccgc aaatctccac    60
tggcgatatg ctgcgtgctg cggtcaaatc tggctccgag ctgggtaaac aagcaaaaga   120
cattatggat gctggcaaac                                              140

<210> SEQ ID NO 28
<211> LENGTH: 139
<212> TYPE: DNA
<213> ORGANISM: Escherichia coli

<400> SEQUENCE: 28
gggaaaggga ctcaggctca gttcatcatg gagaaatatg gtattccgca aatctccact    60
ggcgatatgc tgcgtgctgc ggtcaaatct ggctccgagc tgggtaaaca agcaaaagac   120
attatggatg ctggcaaac                                               139

<210> SEQ ID NO 29
<211> LENGTH: 139
<212> TYPE: DNA
<213> ORGANISM: Escherichia coli

<400> SEQUENCE: 29

```
gggaaaggga ctcaggctca gttcatcatg gagaaatatg gtattccgca aatctccact    60
ggcgatatgc tgcgtgctgc ggtcaaatct ggctccgagc tgggtaaaca agcaaaagac   120
attatggatg ctggcaaat                                                139

<210> SEQ ID NO 30
<211> LENGTH: 139
<212> TYPE: DNA
<213> ORGANISM: Escherichia coli

<400> SEQUENCE: 30
gggaaaggga ctcaggctca gttcatcatg gagaaatatg gtattccgca aatctccact    60
ggcgatatgc tgcgtgctgc ggtcaaatct ggctccgagc tgggtaaaca agcaaaggac   120
attatggatg ctggcaaac                                                139

<210> SEQ ID NO 31
<211> LENGTH: 200
<212> TYPE: DNA
<213> ORGANISM: Escherichia coli

<400> SEQUENCE: 31
gggaaaggga ctcaggctca gttcatcatg gagaaatatg gtattccgca aatctccact    60
ggcgatatgc tgcgtgctgc ggtcaaatct ggctccgagc tgggtaaaca agcaaaagac   120
attatggatg ctggcaaact ggtcaccgac gaactggtga tcgcgctggt taaagagcgc   180
attgctcagg aagactgccg                                               200
```

METHODS AND MATERIALS FOR DETECTING CONTAMINATED FOOD PRODUCTS

CROSS-REFERENCE TO RELATED APPLICATION

This application is a continuation of U.S. application Ser. No. 14/090,167, filed Nov. 26, 2013 (now U.S. Pat. No. 9,150,932), which is a continuation of U.S. application Ser. No. 13/027,980, filed Feb. 15, 2011 (now U.S. Pat. No. 8,623,616), which claims the benefit of priority of U.S. Provisional Application Ser. No. 61/304,781, filed Feb. 15, 2010. The disclosure of the prior applications are considered part of (and are incorporated by reference in) the disclosure of this application.

BACKGROUND

1. Technical Field

This document relates to methods and materials involved in detecting contaminated food products. For example, this document relates to methods and materials involved in using an enzymatic amplification cascade of restriction endonucleases to detect nucleic acid of a microorganism or virus (e.g., a pathogen) within a sample (e.g., food product sample) being tested, thereby assessing a food product for possible contamination.

2. Background

The presence of pathogens in food products represents a risk to public health and safety. For example, food products contaminated with pathogens, if consumed, can lead to sickness and in some cases death. Thus, many food manufacturers, producers, processors, and suppliers invest substantial resources toward proper sampling and testing techniques to help ensure that food products are safe for consumption.

SUMMARY

This document provides methods and materials for detecting contaminated food products. For example, this document provides methods and materials related to the use of an enzymatic amplification cascade of restriction endonucleases to detect nucleic acid of a microorganism or virus (e.g., a pathogen) within a sample (e.g., a food product sample) being tested, thereby assessing a food product for possible contamination. In some cases, this document provides methods and materials for detecting a target microorganism's or virus' nucleic acid. For example, this document provides methods and materials for detecting the presence or absence of target nucleic acid (e.g., a target pathogen's nucleic acid) within a sample (e.g., a food product sample), methods and materials for detecting the amount of target nucleic acid (e.g., a target pathogen's nucleic acid) present within a sample (e.g., a food product sample), kits for detecting the presence or absence of target nucleic acid (e.g., a target pathogen's nucleic acid) within a sample (e.g., a food product sample), kits for detecting the amount of target nucleic acid (e.g., a target pathogen's nucleic acid) present within a sample (e.g., a food product sample), and methods for making such kits.

In general, the methods and materials provided herein can include performing an enzymatic amplification cascade of restriction endonucleases as described herein to detect a target microorganism's or virus's nucleic acid (e.g., a target pathogen's nucleic acid) in a sample (e.g., a food product sample) in a manner that is rapid, inexpensive, sensitive, and specific. For example, a food product sample can be obtained and/or processed such that target microbial or viral nucleic acid (e.g., target pathogen nucleic acid), if present within the sample, is capable of hybridizing to probe nucleic acid of an enzymatic amplification cascade of restriction endonucleases described herein. In some cases, such an obtained and/or processed food product sample can be assessed for the presence, absence, or amount of target microbial or viral nucleic acid (e.g., target pathogen nucleic acid) using an enzymatic amplification cascade of restriction endonucleases described herein without using a nucleic acid amplification technique (e.g., a PCR-based nucleic acid technique). Assessing samples (e.g., food product samples) for the presence, absence, or amount of target nucleic acid using an enzymatic amplification cascade of restriction endonucleases described herein without using a nucleic acid amplification technique can allow food manufacturers, producers, processors, and suppliers as well as food testing entities and government agencies to test food products without the need for potentially expensive thermal cycling devices and potentially time consuming thermal cycling techniques. In addition, the methods and materials provided herein can allow food manufacturers, producers, processors, and suppliers as well as food testing entities and government agencies to assess food products as well as materials that come in contact with food products (e.g., processing machinery, processing personnel, and water supplies) for nucleic acid of any type of microbial organism (e.g., a microbial pathogen) or virus (e.g., a viral pathogen) suspected of contaminating a food product. For example, the methods and materials provided herein can be used to detect the presence, absence, or amount of microbial organisms such as *Escherichia coli* or *Staphylococcus aureus* in a beef product (e.g., ground beef).

In general, one aspect of this document features a method for assessing a food product for contamination. The method comprises, or consists essentially of, (a) contacting a sample from the food product with a probe nucleic acid comprising an amplifying restriction endonuclease and a nucleotide sequence complementary to a sequence of a target nucleic acid present within a microorganism or virus under conditions wherein, if the target nucleic acid is present in the sample, at least a portion of the target nucleic acid hybridizes to at least a portion of the probe nucleic acid to form a double-stranded portion of nucleic acid comprising a restriction endonuclease cut site, (b) contacting the double-stranded portion of nucleic acid with a recognition restriction endonuclease having the ability to cut the double-stranded portion of nucleic acid at the restriction endonuclease cut site under conditions wherein the recognition restriction endonuclease cleaves the double-stranded portion of nucleic acid at the restriction endonuclease cut site, thereby separating a portion of the probe nucleic acid comprising the amplifying restriction endonuclease from at least another portion of the probe nucleic acid, (c) contacting the portion of the probe nucleic acid comprising the amplifying restriction endonuclease with a reporter nucleic acid comprising a double-stranded portion of nucleic acid comprising a restriction endonuclease cut site of the amplifying restriction endonuclease under conditions wherein the amplifying restriction endonuclease cleaves the reporter nucleic acid at the restriction endonuclease cut site of the amplifying restriction endonuclease, thereby separating a portion of the reporter nucleic acid from at least another portion of the reporter nucleic acid, and (d) determining the presence or absence of the portion of the reporter nucleic acid, wherein the presence of the portion of the reporter nucleic acid indicates that the sample contains the target nucleic acid and is thereby contaminated, and wherein the absence of the portion of the reporter nucleic acid indicates that the sample does not contain the target nucleic acid and is thereby not contaminated. The food product can be selected from the group consisting of beef products, poultry products, pork products, and dairy products. The food product can be ground beef or a beef trimming. The food product can be milk. The food product can be chicken meat. The sample can comprise a food product sample obtained from the food product. The sample can comprise a liquid rinse obtained from the food product. The sample can comprise a pooled plurality of samples randomly obtained from the food product. Prior to step (a), the sample can be a sample that was cultured to enrich the population of microorganisms or viruses, if present, within the sample. The sample can be a sample that was cultured for at least 30 minutes in the presence of enrichment medium. Prior to step (a), the sample can be a sample that was processed to remove non-nucleic acid material from the sample, thereby increasing the concentration of nucleic acid, if present, within the sample. The sample can be a sample that was subjected to a nucleic acid extraction technique. Prior to step (a), the sample can be a sample that was subjected to a nucleic acid amplification technique to increase the concentration of microbial or viral nucleic acid, if present, within the sample. The sample can be a sample that was subjected to a PCR-based technique designed to amplify the target nucleic acid. Prior to step (a), the method can comprise culturing the sample to enrich the population of microorganisms or viruses, if present, within the sample. The culturing can comprise culturing the sample for at least 30 minutes in the presence of enrichment medium. Prior to step (a), the method can comprise removing non-nucleic acid material from the sample, thereby increasing the concentration of nucleic acid, if present, within the sample. The removing can comprise performing a nucleic acid extraction technique. Prior to step (a), the method can comprise performing a nucleic acid amplification technique to increase the concentration of microbial or viral nucleic acid, if present, within the sample. The nucleic acid amplification technique can comprise a PCR-based technique designed to amplify the target nucleic acid. Prior to step (a), the method can comprise (i) culturing the sample to enrich the population of microorganisms or viruses, if present, within the sample and removing non-nucleic acid material from the sample, thereby increasing the concentration of nucleic acid, if present, within the sample or (ii) culturing the sample to enrich the population of microorganisms or viruses, if present, within the sample, removing non-nucleic acid material from the sample, thereby increasing the concentration of nucleic acid, if present, within the sample, and performing a nucleic acid amplification technique to increase the concentration of microbial or viral nucleic acid, if present, within the sample.

In some cases, the probe nucleic acid can be single-stranded probe nucleic acid. The probe nucleic acid can be attached to a solid support. The probe nucleic acid can be directly attached to a solid support. The portion of the probe nucleic acid comprising the amplifying restriction endonuclease can be released from the solid support via the step (b). Step (a) and step (b) can be performed in the same compartment, or step (a), step (b), and step (c) can be performed in the same compartment, or step (a), step (b), step (c), and step (d) can be performed in the same compartment. Step (a) and step (b) can be performed in a first compartment, and step (c) can be performed in a second compartment. Step (a) and step (b) can be performed by adding the sample to a compartment comprising the probe nucleic acid and the recognition restriction endonuclease. The probe nucleic acid can comprise (i) a single-stranded portion comprising the nucleotide sequence complementary to the sequence of the target nucleic acid and (ii) a double-stranded portion. The probe nucleic acid can comprise a first nucleic acid strand comprising the nucleotide sequence complementary to the sequence of the target nucleic acid hybridized to a second nucleic acid strand comprising the amplifying restriction endonuclease. The first nucleic acid strand can be attached to a solid support. The first nucleic acid strand can be directly attached to a solid support. A portion of the second nucleic acid strand can hybridize with the first nucleic acid strand to form the double-stranded portion. The portion of the probe nucleic acid comprising the amplifying restriction endonuclease that is separated from the at least another portion of the probe nucleic acid in step (b) can comprise a portion of the first nucleic acid strand and all of the second strand. The portion of the probe nucleic acid comprising the amplifying restriction endonuclease that is separated from the at least another portion of the probe nucleic acid in step (b) can comprise at least a portion of the target nucleic acid.

In some cases, the method can comprise using a plurality of the probe nucleic acid in the step (a). The method can comprise using a plurality of the reporter nucleic acid in the step (c). The reporter nucleic acid in the step (c) can be in molar excess of the portion of the probe nucleic acid comprising the amplifying restriction endonuclease from the step (b). The number of molecules of the portion of the probe nucleic acid comprising the amplifying restriction endonuclease that is separated from the at least another portion of the probe nucleic acid in step (b) can be in an essentially linear relationship to the number of molecules of the target nucleic acid present in the sample. The reporter nucleic acid can be attached to a solid support. The reporter nucleic acid can be directly attached to a solid support. The reporter nucleic acid can comprise a single-stranded portion of nucleic acid. The reporter nucleic acid can comprise a label. The label can be a fluorescent label, a radioactive label, an enzyme label, or a redox label. The portion of the reporter nucleic acid that is separated from the at least another portion of the reporter nucleic acid can comprise the label. The reporter nucleic acid can comprise a first nucleic acid strand comprising the label hybridized to a second nucleic acid strand. The second nucleic acid strand can be attached to a solid support. The second nucleic acid strand can be directly attached to a solid support. A portion of the first nucleic acid strand can hybridize with the second nucleic acid strand to form the double-stranded portion of nucleic acid comprising the restriction endonuclease cut site of the amplifying restriction endonuclease. The reporter nucleic acid can comprise a third nucleic acid strand. The third nucleic acid strand can hybridize with the second nucleic acid strand to form the double-stranded portion of nucleic acid comprising the restriction endonuclease cut site of the amplifying restriction endonuclease. The reporter nucleic acid can be attached to a solid support, and the portion of the reporter nucleic acid that is separated from the at least another portion of the reporter nucleic acid and that comprises the label can be released from the solid support via the step (c). The determining step (d) can comprise detecting the label. The label can be a fluorescent label, and the determining step (d) can comprise detecting the fluorescent label. The determining step (d) can comprise detecting the portion of the reporter nucleic acid separated from the at least another portion of the reporter nucleic acid using a capillary electrophoresis technique. The steps (a), (b), and (c) can be performed without nucleic acid amplification, or the steps (a), (b), (c), and (d) can be performed without nucleic acid amplification. The determining step can comprise determining the amount of the target nucleic acid present within the sample.

In another aspect, this document features a method for assessing a food product for contamination. The method comprises, or consists essentially of, (a) contacting a sample from the food product with a probe nucleic acid comprising an initial amplifying restriction endonuclease and a nucleotide sequence complementary to a sequence of a target nucleic acid present within a microorganism or virus under conditions wherein, if the target nucleic acid is present in the sample, at least a portion of the target nucleic acid hybridizes to at least a portion of the probe nucleic acid to form a double-stranded portion of nucleic acid comprising a restriction endonuclease cut site, (b) contacting the double-stranded portion of nucleic acid with a recognition restriction endonuclease having the ability to cut the double-stranded portion of nucleic acid at the restriction endonuclease cut site under conditions wherein the recognition restriction endonuclease cleaves the double-stranded portion of nucleic acid at the restriction endonuclease cut site, thereby separating a portion of the probe nucleic acid comprising the initial amplifying restriction endonuclease from at least another portion of the probe nucleic acid, (c) contacting the portion of the probe nucleic acid comprising the initial amplifying restriction endonuclease with a first nucleic acid comprising a secondary amplifying restriction endonuclease and a double-stranded portion of nucleic acid comprising a restriction endonuclease cut site of the initial amplifying restriction endonuclease under conditions wherein the initial amplifying restriction endonuclease cleaves the first nucleic acid at the restriction endonuclease cut site of the initial amplifying restriction endonuclease, thereby separating a portion of the first nucleic acid comprising the secondary amplifying restriction endonuclease from at least another portion of the first nucleic acid, (d) contacting the portion of the first nucleic acid comprising the secondary amplifying restriction endonuclease with a second nucleic acid comprising the initial amplifying restriction endonuclease and a double-stranded portion of nucleic acid comprising a restriction endonuclease cut site of the secondary amplifying restriction endonuclease under conditions wherein the secondary amplifying restriction endonuclease cleaves the second nucleic acid at the restriction endonuclease cut site of the secondary amplifying restriction endonuclease, thereby separating a portion of the second nucleic acid comprising the initial amplifying restriction endonuclease from at least another portion of the second nucleic acid, (e) contacting the portion of the second nucleic acid comprising the initial amplifying restriction endonuclease with a reporter nucleic acid comprising a double-stranded portion of nucleic acid comprising a restriction endonuclease cut site of the initial amplifying restriction endonuclease under conditions wherein the initial amplifying restriction endonuclease cleaves the reporter nucleic acid at the restriction endonuclease cut site of the initial amplifying restriction endonuclease, thereby separating a portion of the reporter nucleic acid from at least another portion of the reporter nucleic acid, and (f) determining the presence or absence of the portion of the reporter nucleic acid, wherein the presence of the portion of the reporter nucleic acid indicates that the sample contains the target nucleic acid and is thereby contaminated, and wherein the absence of the portion of the reporter nucleic acid indicates that the sample does not contain the target nucleic acid and is thereby not contaminated. The food product can be selected from the group consisting of beef products, poultry products, pork products, and dairy products. The food product can be ground beef or a beef trimming. The food product can be milk. The food product can be chicken meat. The sample can comprise a food product sample obtained from the food product. The sample can comprise a liquid rinse obtained from the food product. The sample can comprise a pooled plurality of samples randomly obtained from the food product. Prior to step (a), the sample can be a sample that was cultured to enrich the population of microorganisms or viruses, if present, within the sample. The sample can be a sample that was cultured for at least 30 minutes in the presence of enrichment medium. Prior to step (a), the sample can be a sample that was processed to remove non-nucleic acid material from the sample, thereby increasing the concentration of nucleic acid, if present, within the sample. The sample can be a sample that was subjected to a nucleic acid extraction technique. Prior to step (a), the sample can be a sample that was subjected to a nucleic acid amplification technique to increase the concentration of microbial or viral nucleic acid, if present, within the sample. The sample can be a sample that was subjected to a PCR-based technique designed to amplify the target nucleic acid. Prior to step (a), the method can comprise culturing the sample to enrich the population of microorganisms or viruses, if present, within the sample. The culturing can comprise culturing the sample for at least 30 minutes in the presence of enrichment medium. Prior to step (a), the method can comprise removing non-nucleic acid material from the sample, thereby increasing the concentration of nucleic acid, if present, within the sample. The removing can comprise performing a nucleic acid extraction technique. Prior to step (a), the method can comprise performing a nucleic acid amplification technique to increase the concentration of microbial or viral nucleic acid, if present, within the sample. The nucleic acid amplification technique can comprise a PCR-based technique designed to amplify the target nucleic acid. Prior to step (a), the method can comprise (i) culturing the sample to enrich the population of microorganisms or viruses, if present, within the sample and removing non-nucleic acid material from the sample, thereby increasing the concentration of nucleic acid, if present, within the sample or (ii) culturing the sample to enrich the population of microorganisms or viruses, if present, within the sample, removing non-nucleic acid material from the sample, thereby increasing the concentration of nucleic acid, if present, within the sample, and performing a nucleic acid amplification technique to increase the concentration of microbial or viral nucleic acid, if present, within the sample.

In some cases, the probe nucleic acid can be single-stranded probe nucleic acid. The probe nucleic acid can be attached to a solid support. The probe nucleic acid can be directly attached to a solid support. The portion of the probe nucleic acid comprising the initial amplifying restriction endonuclease can be released from the solid support via the step (b). Step (a) and step (b) can be performed in the same compartment, step (a), step (b), and step (c) can be performed in the same compartment, step (a), step (b), step (c), and step (d) can be performed in the same compartment, step (a), step (b), step (c), step (d), and step (e) can be performed in the same compartment, or step (a), step (b), step (c), step (d), step (e), and step (f) can be performed in the same compartment. Step (c) and step (d) can be performed in the same compartment. Step (a) and step (b) can be performed in a first compartment, and step (c) and step (d) can be performed in a second compartment. Step (a) and step (b) can be performed by adding the sample to a compartment comprising the probe nucleic acid and the recognition restriction endonuclease. Step (c) and step (d) can be performed by adding the portion of the probe nucleic acid comprising the initial amplifying restriction endonuclease to a compartment comprising the first nucleic acid and the second nucleic acid. The probe nucleic acid can comprise (i) a single-stranded portion comprising the nucleotide sequence complementary to the sequence of the target nucleic acid and (ii) a double-stranded portion. The probe nucleic acid can comprise a first nucleic acid strand comprising the nucleotide sequence complementary to the sequence of the target nucleic acid hybridized to a second nucleic acid strand comprising the initial amplifying restriction endonuclease. The first nucleic acid strand can be attached to a solid support. The first nucleic acid strand can be directly attached to a solid support. A portion of the second nucleic acid strand can hybridize with the first nucleic acid strand to form the double-stranded portion. The portion of the probe nucleic acid comprising the initial amplifying restriction endonuclease that is separated from the at least another portion of the probe nucleic acid in step (b) can comprise a portion of the first nucleic acid strand and all of the second strand. The portion of the probe nucleic acid comprising the initial amplifying restriction endonuclease that is separated from the at least another portion of the probe nucleic acid in step (b) can comprise at least a portion of the target nucleic acid. The method can comprise using a plurality of the probe nucleic acid in the step (a). The method can comprise using a plurality of the reporter nucleic acid in the step (e). The reporter nucleic acid in the step (e) can be in molar excess of the portion of the probe nucleic acid comprising the initial amplifying restriction endonuclease from the step (b). The number of molecules of the portion of the probe nucleic acid comprising the initial amplifying restriction endonuclease that is separated from the at least another portion of the probe nucleic acid in step (b) can be in an essentially linear relationship to the number of molecules of the target nucleic acid present in the sample. The first nucleic acid and the second nucleic acid can be attached to a solid support. The first nucleic acid and the second nucleic acid can be directly attached to a solid support. The first nucleic acid and the second nucleic acid can be attached to a solid support in the same compartment. The portion of the first nucleic acid comprising the secondary amplifying restriction endonuclease can be released from the solid support via the step (c). The portion of the second nucleic acid comprising the initial amplifying restriction endonuclease can be released from the solid support via the step (d). The first nucleic acid can comprise a first nucleic acid strand comprising the secondary amplifying restriction endonuclease hybridized to a second nucleic acid strand to form the double-stranded portion of nucleic acid comprising the restriction endonuclease cut site of the initial amplifying restriction endonuclease. The first nucleic acid strand can be attached to a solid support. The first nucleic acid strand can be directly attached to a solid support. The second nucleic acid strand can be attached to a solid support. The second nucleic acid strand can be directly attached to a solid support. The second nucleic acid can comprise a first nucleic acid strand comprising the initial amplifying restriction endonuclease hybridized to a second nucleic acid strand to form the double-stranded portion of nucleic acid comprising the restriction endonuclease cut site of the secondary amplifying restriction endonuclease. The first nucleic acid strand can be attached to a solid support. The first nucleic acid strand can be directly attached to a solid support. The second nucleic acid strand can be attached to a solid support. The second nucleic acid strand can be directly attached to a solid support. The reporter nucleic acid can be attached to a solid support. The reporter nucleic acid can be directly attached to a solid support. The reporter nucleic acid can comprise a single-stranded portion of nucleic acid. The reporter nucleic acid can comprise a label. The label can be a fluorescent label, a radioactive label, an enzyme label, or a redox label. The portion of the reporter nucleic acid that is separated from the at least another portion of the reporter nucleic acid can comprise the label. The reporter nucleic acid can comprise a first nucleic acid strand comprising the label hybridized to a second nucleic acid strand. The second nucleic acid strand can be attached to a solid support. The second nucleic acid strand can be directly attached to a solid support. A portion of the first nucleic acid strand can hybridize with the second nucleic acid strand to form the double-stranded portion of nucleic acid comprising the restriction endonuclease cut site of the initial amplifying restriction endonuclease. The reporter nucleic acid can comprise a third nucleic acid strand. The third nucleic acid strand can hybridize with the second nucleic acid strand to form the double-stranded portion of nucleic acid comprising the restriction endonuclease cut site of the initial amplifying restriction endonuclease. The reporter nucleic acid can be attached to a solid support, and the portion of the reporter nucleic acid that is separated from the at least another portion of the reporter nucleic acid and that comprises the label can be released from the solid support via the step (e). The determining step (f) can comprise detecting the label. The label can be a fluorescent label, and the determining step (f) can comprise detecting the fluorescent label. The determining step (f) can comprise detecting the portion of the reporter nucleic acid separated from the at least another portion of the reporter nucleic acid using a capillary electrophoresis technique. The steps (a), (b), (c), (d), and (e) can be performed without nucleic acid amplification, or the steps (a), (b), (c), (d), (e), and (f) can be performed without nucleic acid amplification. The determining step can comprise determining the amount of the target nucleic acid present within the sample.

In another aspect, this document features a method for assessing a food product for contamination. The method comprises, or consists essentially of, (a) contacting a sample from the food product with a probe nucleic acid comprising an initial amplifying restriction endonuclease and a nucleotide sequence complementary to a sequence of a target nucleic acid present within a microorganism or virus under conditions wherein, if the target nucleic acid is present in the sample, at least a portion of the target nucleic acid hybridizes to at least a portion of the probe nucleic acid to form a double-stranded portion of nucleic acid comprising a restriction endonuclease cut site, (b) contacting the double-stranded portion of nucleic acid with a recognition restriction endonuclease having the ability to cut the double-stranded portion of nucleic acid at the restriction endonuclease cut site under conditions wherein the recognition restriction endonuclease cleaves the double-stranded portion of nucleic acid at the restriction endonuclease cut site, thereby separating a portion of the probe nucleic acid comprising the initial amplifying restriction endonuclease from at least another portion of the probe nucleic acid, (c) contacting the portion of the probe nucleic acid comprising the initial amplifying restriction endonuclease with a first reporter nucleic acid comprising a secondary amplifying restriction endonuclease and a double-stranded portion of nucleic acid comprising a restriction endonuclease cut site of the initial amplifying restriction endonuclease under conditions wherein the initial amplifying restriction endonuclease cleaves the first reporter nucleic acid at the restriction endonuclease cut site of the initial amplifying restriction endonuclease, thereby separating a portion of the first nucleic acid comprising the secondary amplifying restriction endonuclease from at least another portion of the first nucleic acid, (d) contacting the portion of the first reporter nucleic acid comprising the secondary amplifying restriction endonuclease with a second reporter nucleic acid comprising the initial amplifying restriction endonuclease and a double-stranded portion of nucleic acid comprising a restriction endonuclease cut site of the secondary amplifying restriction endonuclease under conditions wherein the initial amplifying restriction endonuclease cleaves the second nucleic acid at the restriction endonuclease cut site of the secondary amplifying restriction endonuclease, thereby separating a portion of the second nucleic acid comprising the initial amplifying restriction endonuclease from at least another portion of the second nucleic acid, and (e) determining the presence or absence of the portion of the first reporter nucleic acid, the second reporter nucleic acid, or both the first reporter nucleic acid and the second reporter nucleic acid, wherein the presence indicates that the sample contains the target nucleic acid and is thereby contaminated, and wherein the absence indicates that the sample does not contain the target nucleic acid and is thereby not contaminated. The food product can be selected from the group consisting of beef products, poultry products, pork products, and dairy products. The food product can be ground beef or a beef trimming. The food product can be milk. The food product can be chicken meat. The sample can comprise a food product sample obtained from the food product. The sample can comprise a liquid rinse obtained from the food product. The sample can comprise a pooled plurality of samples randomly obtained from the food product. Prior to step (a), the sample can be a sample that was cultured to enrich the population of microorganisms or viruses, if present, within the sample. The sample can be a sample that was cultured for at least 30 minutes in the presence of enrichment medium. Prior to step (a), the sample can be a sample that was processed to remove non-nucleic acid material from the sample, thereby increasing the concentration of nucleic acid, if present, within the sample. The sample can be a sample that was subjected to a nucleic acid extraction technique. Prior to step (a), the sample can be a sample that was subjected to a nucleic acid amplification technique to increase the concentration of microbial or viral nucleic acid, if present, within the sample. The sample can be a sample that was subjected to a PCR-based technique designed to amplify the target nucleic acid. Prior to step (a), the method can comprise culturing the sample to enrich the population of microorganisms or viruses, if present, within the sample. The culturing can comprise culturing the sample for at least 30 minutes in the presence of enrichment medium. Prior to step (a), the method can comprise removing non-nucleic acid material from the sample, thereby increasing the concentration of nucleic acid, if present, within the sample. The removing can comprise performing a nucleic acid extraction technique. Prior to step (a), the method can comprise performing a nucleic acid amplification technique to increase the concentration of microbial or viral nucleic acid, if present, within the sample. The nucleic acid amplification technique can comprise a PCR-based technique designed to amplify the target nucleic acid. Prior to step (a), the method can comprise (i) culturing the sample to enrich the population of microorganisms or viruses, if present, within the sample and removing non-nucleic acid material from the sample, thereby increasing the concentration of nucleic acid, if present, within the sample or (ii) culturing the sample to enrich the population of microorganisms or viruses, if present, within the sample, removing non-nucleic acid material from the sample, thereby increasing the concentration of nucleic acid, if present, within the sample, and performing a nucleic acid amplification technique to increase the concentration of microbial or viral nucleic acid, if present, within the sample. The probe nucleic acid can be single-stranded probe nucleic acid. The probe nucleic acid can be attached to a solid support. The probe nucleic acid can be directly attached to a solid support. The portion of the probe nucleic acid comprising the initial amplifying restriction endonuclease can be released from the solid support via the step (b). Step (a) and step (b) can be performed in the same compartment, step (a), step (b), and step (c) can be performed in the same compartment, step (a), step (b), step (c), and step (d) can be performed in the same compartment, or step (a), step (b), step (c), step (d), and step (e) can be performed in the same compartment. Step (c) and step (d) can be performed in the same compartment. Step (a) and step (b) can be performed in a first compartment, and step (c) and step (d) can be performed in a second compartment. Step (a) and step (b) can be performed by adding the sample to a compartment comprising the probe nucleic acid and the recognition restriction endonuclease. Step (c) and step (d) can be performed by adding the portion of the probe nucleic acid comprising the initial amplifying restriction endonuclease to a compartment comprising the first reporter nucleic acid and the second reporter nucleic acid. The probe nucleic acid can comprise (i) a single-stranded portion comprising the nucleotide sequence complementary to the sequence of the target nucleic acid and (ii) a double-stranded portion. The probe nucleic acid can comprise a first nucleic acid strand comprising the nucleotide sequence complementary to the sequence of the target nucleic acid hybridized to a second nucleic acid strand comprising the initial amplifying restriction endonuclease. The first nucleic acid strand can be attached to a solid support. The first nucleic acid strand can be directly attached to a solid support. A portion of the second nucleic acid strand can hybridize with the first nucleic acid strand to form the double-stranded portion. The portion of the probe nucleic acid comprising the initial amplifying restriction endonuclease that is separated from the at least another portion of the probe nucleic acid in step (b) can comprise a portion of the first nucleic acid strand and all of the second strand. The portion of the probe nucleic acid comprising the initial amplifying restriction endonuclease that is separated from the at least another portion of the probe nucleic acid in step (b) can comprise at least a portion of the target nucleic acid.

In some cases, the method can comprise using a plurality of the probe nucleic acid in the step (a). The method can comprise using a plurality of the first reporter nucleic acid in the step (c). The first reporter nucleic acid in the step (c) can be in molar excess of the portion of the probe nucleic acid comprising the initial amplifying restriction endonuclease from the step (b). The method can comprise using a plurality of the second reporter nucleic acid in the step (d). The second reporter nucleic acid in the step (d) can be in molar excess of the portion of the probe nucleic acid comprising the initial amplifying restriction endonuclease from the step (b). The number of molecules of the portion of the probe nucleic acid comprising the initial amplifying restriction endonuclease that is separated from the at least another portion of the probe nucleic acid in step (b) can be in an essentially linear relationship to the number of molecules of the target nucleic acid present in the sample. The first reporter nucleic acid and the second reporter nucleic acid can be attached to a solid support. The first reporter nucleic acid and the second reporter nucleic acid can be directly attached to a solid support. The first reporter nucleic acid and the second reporter nucleic acid can be attached to a solid support in the same compartment. The portion of the first reporter nucleic acid comprising the secondary amplifying restriction endonuclease can be released from the solid support via the step (c). The portion of the second reporter nucleic acid comprising the initial amplifying restriction endonuclease can be released from the solid support via the step (d). The first reporter nucleic acid can comprise a label. The label can be a fluorescent label, a radioactive label, an enzyme label, or a redox label. The second reporter nucleic acid can comprise a label. The label can be a fluorescent label, a radioactive label, an enzyme label, or a redox label. The first reporter nucleic acid and the second reporter nucleic acid can comprise a label. The first reporter nucleic acid and the second reporter nucleic acid can comprise the same label. The label can comprise a fluorescent label, a radioactive label, an enzyme label, or a redox label. The first reporter nucleic acid can be attached to a solid support, the portion of the first reporter nucleic acid that is separated from the at least another portion of the first reporter nucleic acid can comprise a label, and the portion of the first reporter nucleic acid that is separated from the at least another portion of the first reporter nucleic acid and that comprises the label can be released from the solid support via the step (c). The first reporter nucleic acid can comprise a first nucleic acid strand comprising the secondary amplifying restriction endonuclease hybridized to a second nucleic acid strand to form the double-stranded portion of nucleic acid comprising the restriction endonuclease cut site of the initial amplifying restriction endonuclease. The first nucleic acid strand can be attached to a solid support. The first nucleic acid strand can be directly attached to a solid support. The second nucleic acid strand can be attached to a solid support. The second nucleic acid strand can be directly attached to a solid support. The first nucleic acid strand can comprise a label. The label can be a fluorescent label, a radioactive label, an enzyme label, or a redox label. The second nucleic acid strand can comprise a label. The label can be a fluorescent label, a radioactive label, an enzyme label, or a redox label. The second reporter nucleic acid can be attached to a solid support, the portion of the second reporter nucleic acid that is separated from the at least another portion of the second reporter nucleic acid can comprise a label, and the portion of the second reporter nucleic acid that is separated from the at least another portion of the second reporter nucleic acid and that comprises the label can be released from the solid support via the step (d). The second reporter nucleic acid can comprise a first nucleic acid strand comprising the initial amplifying restriction endonuclease hybridized to a second nucleic acid strand to form the double-stranded portion of nucleic acid comprising the restriction endonuclease cut site of the secondary amplifying restriction endonuclease. The first nucleic acid strand can be attached to a solid support. The first nucleic acid strand can be directly attached to a solid support. The second nucleic acid strand can be attached to a solid support. The second nucleic acid strand can be directly attached to a solid support. The first nucleic acid strand can comprise a label. The label can be a fluorescent label, a radioactive label, an enzyme label, or a redox label. The second nucleic acid strand can comprise a label. The label can be a fluorescent label, a radioactive label, an enzyme label, or a redox label. The portion of the first reporter nucleic acid separated from the at least another portion of the first reporter nucleic acid can comprise a fluorescent label, the portion of the second reporter nucleic acid separated from the at least another portion of the second reporter nucleic acid can comprise a fluorescent label, and the determining step (e) can comprise detecting the fluorescent label. The determining step (e) can comprise detecting the portion of the first reporter nucleic acid separated from the at least another portion of the first reporter nucleic acid using a capillary electrophoresis technique. The determining step (e) can comprise detecting the portion of the second reporter nucleic acid separated from the at least another portion of the second reporter nucleic acid using a capillary electrophoresis technique. The steps (a), (b), (c), and (d) can be performed without nucleic acid amplification, or the steps (a), (b), (c), (d), and (e) can be performed without nucleic acid amplification. The determining step can comprise determining the amount of the target nucleic acid present within the sample.

In another aspect, this document features a kit for assessing a food product for contamination. The kit comprises, or consists essentially of, a probe nucleic acid comprising an amplifying restriction endonuclease and a nucleotide sequence complementary to a sequence of a target nucleic acid present in a microorganism or virus, wherein at least a portion of the target nucleic acid is capable of hybridizing to at least a portion of the probe nucleic acid to form a double-stranded portion of nucleic acid comprising a restriction endonuclease cut site. The probe nucleic acid can be single-stranded probe nucleic acid. The kit can comprise a solid support, and the probe nucleic acid can be attached to the solid support. A portion of the probe nucleic acid comprising the amplifying restriction endonuclease can be releasable from the solid support via cleavage with a recognition restriction endonuclease having the ability to cleave at the restriction endonuclease cut site. The kit can further comprise the recognition restriction endonuclease. The probe nucleic acid can comprise (i) a single-stranded portion comprising the nucleotide sequence complementary to the sequence of the target nucleic acid and (ii) a double-stranded portion. The probe nucleic acid can comprise a first nucleic acid strand comprising the nucleotide sequence complementary to the sequence of the target nucleic acid hybridized to a second nucleic acid strand comprising the amplifying restriction endonuclease. The kit can further comprise a reporter nucleic acid comprising a double-stranded portion of nucleic acid comprising a restriction endonuclease cut site of the amplifying restriction endonuclease. The kit can comprise a solid support, and the reporter nucleic acid can be attached to the solid support. The reporter nucleic acid can be directly attached to the solid support. The reporter nucleic acid can comprise a single-stranded portion of nucleic acid. The reporter nucleic acid can comprise a label. The label can be a fluorescent label, a radioactive label, an enzyme label, or a redox label. A portion of the reporter nucleic acid comprising the label can be capable of being separated from at least another portion of the reporter nucleic acid via cleavage by the amplifying restriction endonuclease. The reporter nucleic acid can comprise a first nucleic acid strand comprising the label hybridized to a second nucleic acid strand. The kit can further comprise (a) a first signal expansion nucleic acid comprising a secondary amplifying restriction endonuclease and a double-stranded section having a restriction endonuclease cut site for the amplifying restriction endonuclease, and (b) a second signal expansion nucleic acid comprising the amplifying restriction endonuclease and a double-stranded section having a restriction endonuclease cut site for the secondary amplifying restriction endonuclease. The probe nucleic acid can be lyophilized. All the ingredients of the kit can be lyophilized or dry.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references (e.g., GenBank® records) mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 4 is a schematic of an exemplary configuration of first signal expansion nucleic acid and second signal expansion nucleic acid that can be used with the methods and materials provided herein for detecting target nucleic acid. Such first signal expansion nucleic acid and second signal expansion nucleic acid can be used with or without reporter nucleic acid. When used without a separate reporter nucleic acid step, such signal expansion nucleic acid can be referred to as reporter nucleic acid.

FIG. 5 is a schematic of an exemplary configuration of first signal expansion nucleic acid and second signal expansion nucleic acid that can be used with the methods and materials provided herein for detecting target nucleic acid. Such first signal expansion nucleic acid and second signal expansion nucleic acid can be used with or without reporter nucleic acid. When used without a separate reporter nucleic acid step, such signal expansion nucleic acid can be referred to as reporter nucleic acid.

FIGS. 8A-8D are a series of schematics showing cross-sectional end-on views of a film in an exemplary reel-to-reel system. Exemplary depictions are shown for the stages of adding target nucleic acid (FIG. 8A) and recognition restriction endonuclease (FIG. 8B), as well as release and action of amplification restriction endonuclease (FIG. 8C), and release of marker from the reporter nucleic acid (FIG. 8D).

DETAILED DESCRIPTION

Figure 1:
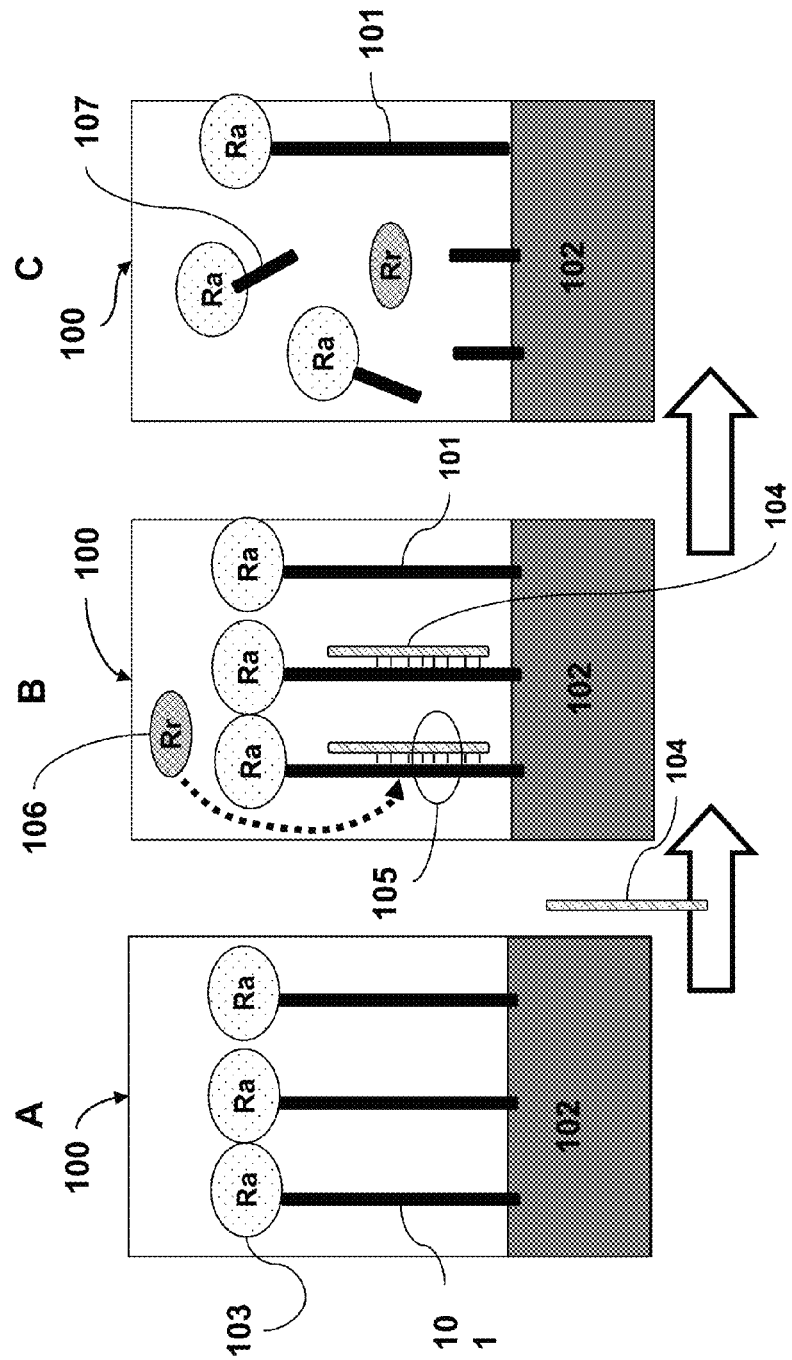
FIG. 1 is a schematic depicting an exemplary method for detecting target nucleic acid using probe nucleic acid, a recognition restriction endonuclease, and reporter nucleic acid.

This document provides methods and materials for detecting contaminated food products. For example, this document provides methods and materials related to the use of an enzymatic amplification cascade of restriction endonucleases to detect nucleic acid of a microorganism or virus (e.g., nucleic acid of a target pathogen) within a sample (e.g., a food product sample) being tested, thereby assessing a food product for possible contamination. In some cases, this document provides methods and materials for detecting a target microorganism's or virus's nucleic acid (e.g., a target pathogen's nucleic acid). For example, this document provides methods and materials for detecting the presence or absence of target nucleic acid (e.g., a target microorganism's or virus's nucleic acid) within a sample (e.g., a food product sample), methods and materials for detecting the amount of target nucleic acid (e.g., a target microorganism's or virus's nucleic acid) present within a sample (e.g., a food product sample), kits for detecting the presence or absence of target nucleic acid (e.g., a target microorganism's or virus's nucleic acid) within a sample (e.g., a food product sample), kits for detecting the amount of target nucleic acid (e.g., a target microorganism's or virus's nucleic acid) present within a sample (e.g., a food product sample), and methods for making such kits.

Any type of food product can be assessed for microbial and/or viral contamination using the methods and materials provided herein. For example, beef products (e.g., ground beef, beef trimmings, beef and veal cuts, or beef sausage), pork products (e.g., pork cuts, bacon, pork renderings, ground pork, or pork sausage), poultry products (e.g., poultry meat cuts, eggs, or cooked poultry), lamb products (e.g., lamb cuts, ground lamb, or lamb sausage), dairy products (e.g., milk, cheese, cream, butter, or yogurt), vegetable products (e.g., beans, peas, corn, lettuce, tomatoes, leaf greens, or soybean sprouts), shellfish products (e.g., scallops, mussels, or oysters), fish products (e.g., fish fillets, whole fish, fish oils, or smoked fish), processed food products (e.g., frozen meals, spreads, ham, or roast beef/pastrami), cooked buffet-style food products (e.g., salads, meats, fruit, or dessert), baked products (e.g., bread, cereal, cakes, or cookies), confectionary products, or fruit products (e.g., fresh fruit, fruit juices, jams, or marmalade) can be assessed for microbial and/or viral contamination as described herein. In addition to having the ability to assess food products for possible microbial and/or viral contamination, the methods and materials provided herein can be used to assess water or a water supply, pharmaceutical products (e.g., drugs), cosmetic products (e.g., lotions or make-up), storage facilities and/or products (e.g., grain silos), or transportation machinery (e.g., railroad cars, trucks, or pipelines) for possible microbial and/or viral contamination. For example, a local ocean environment (e.g., bay) where oysters are harvested can be assessed for possible viral contamination using the methods and materials provided herein.

In some cases, when assessing a particular food product for microbial and/or viral contamination, the sample to be tested can be a food product sample obtained directly from a larger collection of the food product to be assessed for possible contamination. For example, when assessing ground beef products for *E. coli* contamination, a number of individual beef samples (e.g., 60 samples) can be collected randomly from a lot of beef trimmings (e.g., a 2,000 pound beef trim bin or combo) that are used to make ground beef. The collected samples can be tested individually using the methods and materials provided herein or can be pooled to form one or more larger samples that are tested using the methods and materials provided herein. In some cases, when assessing a particular food product for microbial and/or viral contamination, the food product can be assessed indirectly by collecting a sample of a material that has been in contact with the food product to be tested. For example, the sample to be tested can be a sample (e.g., a liquid sample) collected from a solution used to wash or rinse the food product to be assessed for possible contamination or a solution used to wash or rinse processing machinery or other items that come in contact with the food product (e.g., the gloves of processing personnel). In some cases, a sample to be tested can be a swab sample collected from a surface of a food product or a surface of a material that has been in contact with a food product such as the hands or tools of food processing personnel.

A food product (or water sample or water supply) can be assessed for any type of microorganism or virus suspected of contaminating the food product (or water sample or water supply). Examples of potentially contaminating microorganisms include, without limitation, bacterial microorganisms such as *E. coli* (e.g., enterohemorrhagic *E. coli* such as O157: H7 *E. coli* or enteropathogenic *E. coli*), *Staphylococcus aureus*, *Salmonella* species (e.g., *Salmonella enterica*), *Listeria monocytogenes*, *Campylobacter* species (e.g., thermophylic strains of *Campylobacter jejuni*, *C. lari*, or *C. coli*), *Bacillus cereus*, *Vibrio* species, *Yersinia enterocolitica*, *Shigella* species, *Enterococcus* species (e.g., *Enterococcus faecalis* or *E. faecium*), *Helicobacter pylori*, and *Clostridium* species (e.g., *Clostridium botulinum* or *Clostridium perfringens*), fungal microorganisms such as *Aspergillus* species (e.g., *A. flavus*, *A. fumigatus*, and *A. niger*), yeast (e.g., *Candida nonvegensis* and *C. albicans*), *Penicillium* species, *Rhizopus* species, and *Alternaria* species, and protozoan microorganisms such as *Cryptosporidium panvum*, *Giardia lamblia*, and *Toxoplasma gondii*. Examples of potentially contaminating viruses include, without limitation, Norwalk and Norwalk-like viruses, Hepatitis A and E viruses, Rotavirus, and enteric adenoviruses. In some cases, a particular type of food product or sample can be assessed for one or more of the microorganisms or viruses listed in Table 1 using the methods and materials provided herein. When designing a method for detecting a microorganism or virus listed in Table 1, a probe nucleic acid can be designed to be complementary to a portion of the indicated sequences from Table 1. For example, when designing a method for detecting *Salmonella enterica* in a meat sample, a probe nucleic acid can be designed to be complementary to a portion of the *S. enterica* sequence set forth in GenBank® GI No. 16421444.

TABLE 1

Possible types of contaminations that can be tested.

| Food Product or Sample Type to be Tested | Possible Contaminant | Genomic sequence (GenBank ® GI or accession numbers) |
|---|---|---|
| Meat, poultry, dairy, egg products | *Escherichia coli* | 91070629; 26111730; 284919779; 260447279; 257762509; 257757386; 254590536; 253976232; 253972022; 242375837; 238859724; 218425442; 218363708; 218359353; 218350208; 215263233; 209910450; 209157093; 170517292; 169887498; 169752989; 157065147 |
| | Enterohaemorrhagic and Enteropathogenic *E. coli* | 257762509; 257757386; 257751862; 47118301; 56384585; 209395693; 254590536 |
| | *Salmonella enterica* | 267991652; 261245233; 224466365; 16445344; 206707319; 205271127; 197936256; 197211055; 197092687; 29140506; 62126203; 194709404; 194405610; 161361677 |
| | *Listeria monocytogenes* | 284058907; 284055817; 225875101; 30407125; 217332573 |
| | *Campylobacter jejuni* | 284925303; 157385286; 152938384; 121504137; 57165696 |
| | *C. lari* | 222538267 |
| | *C. coli* | 57021108 |
| | *Staphylococcus aureus* | 285815727; 283469229; 269939526; 262073980; 160367075; 156720466; 150373012; 149944932; 147739516; 47208328; 57284222; 87201381; 87125858; 49243355; 47118324; 47118312; 82655308; 49240382 |
| | *Bacillus cereus* | CP001407.1; CP001177.1; CP001283.1; AE017194.1; AE016877.1; CP001176.1; CP000001.1; CP001186.1; CP000227.1 |
| Seafood | *Vibrio* strains | 47118310; 262335977 |
| | *Yersinia enterocolitica* | AM286415.1 |
| | Norwalk virus | NC_001959 |
| Vegetable products, contaminated water | *Shigella* species | CP001063.1; CP000036.1; CP000034.1; E005674.1; AE014073.1; P000266.1; CP001383.1; CP000038.1 |
| | *Listeria monocytogenes* | 284058907; 284055817; 225875101; 30407125; 217332573 |
| | *Enterococcus faecalis* | 29350190 |
| | *E. faecium* | 224798581 |
| | *Cryptosporidium parvum* | NC_006980- NC_0069807 |
| | *Giardia lamblia* | 157438443 |
| | *Toxoplasma gondii* | 188573898 |
| | Hepatitis A virus | NC_008250; NC_007204; NC_003990; NC_001489 |
| Food handling, cooked food, personal hygiene | *Helicobacter pylori* | CP000012.1; CP001680.1; AE000511.1; M991728.1; CP001173.1; CP000241.1; AE001439.1; P001217.1; CP001072.2 |
| | *Escherichia coli* | 257762509; 257757386; 257751862; 47118301; 56384585; 209395693; 254590536 |
| | *Salmonella* species | 267991652; 261245233; 224466365; 16445344; 206707319; 205271127; 197936256; 197211055; 197092687; 29140506; 62126203; 194709404; 194405610; 161361677 |
| | *Shigella* species | CP001063.1; CP000036.1; CP000034.1; E005674.1; AE014073.1; P000266.1; CP001383.1; CP000038.1 |
| | *Clostridium botulinum* | CP001581.1; CP000962.1; AM412317.1; P000726.1; CP000727.1; CP000939.1; CP001056.1; CP001083.1; CP001078.1; CP000728.1 |

TABLE 1-continued

Possible types of contaminations that can be tested.

| Food Product or Sample Type to be Tested | Possible Contaminant | Genomic sequence (GenBank ® GI or accession numbers) |
| --- | --- | --- |
| | Clostridium perfringens | CP000246.1; CP000312.1; BA000016.3 |
| | Hepatitis A virus | NC_008250; NC_007204; NC_003990; NC_001489 |
| | Aspergillus flavus | 134215631 |
| | A. fumigatus | NC_007195 |
| | A. niger | NT_166525; NT_166529 |
| | Candida norvegensis | 223640020 |
| | C. albicans | 12539616 |

In one embodiment, a method for assessing a sample (e.g., a food product sample) for the presence, absence, or amount of a contaminating microorganism or virus can include detecting a target microorganism's or virus's nucleic acid (e.g., a target nucleic acid). For example, a food product sample (e.g., a food product sample to be tested or suspected to contain a target microorganism's or virus's nucleic acid) can be placed in contact with probe nucleic acid. The probe nucleic acid can be designed to have a single-stranded portion with a nucleotide sequence that is complementary to at least a portion of the target nucleic acid to be detected. In this case, target nucleic acid present within the sample can hybridize with the complementary sequence of this single-stranded portion of the probe nucleic acid to form a double-stranded section with one strand being target nucleic acid and the other strand being probe nucleic acid. In addition, the single-stranded portion of the probe nucleic acid having the nucleotide sequence that is complementary to at least a portion of the target nucleic acid to be detected can be designed such that hybridization with the target nucleic acid creates a restriction endonuclease cut site. Thus, target nucleic acid present within the sample can hybridize with the complementary sequence of the single-stranded portion of the probe nucleic acid to form a double-stranded section that creates a cut site for a restriction endonuclease. This cut site created by the hybridization of target nucleic acid to probe nucleic acid can be referred to as a recognition restriction endonuclease cut site. In addition, a restriction endonuclease that cleaves nucleic acid at such a recognition restriction endonuclease cut site can be referred to as a recognition restriction endonuclease.

The probe nucleic acid also can be designed to contain a restriction endonuclease. This restriction endonuclease, which can be a component of the probe nucleic acid, can be referred to as an amplifying restriction endonuclease. An amplifying restriction endonuclease is typically a different restriction endonuclease than the restriction endonuclease that is used as a recognition restriction endonuclease. For example, when an EcoRI restriction endonuclease is used as a recognition restriction endonuclease, a restriction endonuclease other than an EcoRI restriction endonuclease (e.g., a Hind III restriction endonuclease) is used as an amplifying restriction endonuclease. Thus, in general, probe nucleic acid is designed to contain an amplifying restriction endonuclease and to have a nucleotide sequence such that the target nucleic acid can hybridize to the probe nucleic acid and create a recognition restriction endonuclease cut site for a recognition restriction endonuclease. In some cases, the probe nucleic acid can be attached to a solid support (e.g., a well of a microtiter plate). For example, the probe nucleic acid can be attached to a solid support such that cleavage at the recognition restriction endonuclease cut site via the recognition restriction endonuclease releases a portion of the probe nucleic acid that contains the amplifying restriction endonuclease.

After contacting the sample (e.g., a food product sample) that may or may not contain target nucleic acid with the probe nucleic acid that is attached to a solid support, the target nucleic acid, if present in the sample, can hybridize to the probe nucleic acid and create the recognition restriction endonuclease cut site. At this point, the recognition restriction endonuclease, whether added to the reaction or already present in the reaction, can cleave the probe nucleic acid at the recognition restriction endonuclease cut sites that are formed by the hybridization of target nucleic acid to the probe nucleic acid, thereby releasing the portion of the probe nucleic acid that contains the amplifying restriction endonuclease from the solid support. The number of amplifying restriction endonuclease-containing portions of the probe nucleic acid that are released from the solid support can be in an essentially linear relationship (e.g., essentially a one-for-one relationship) with the number of target nucleic acid molecules that hybridize with the probe nucleic acid to form the recognition restriction endonuclease cut site.

The portions of the probe nucleic acid containing the amplifying restriction endonuclease that were released from the solid support can be collected and placed in contact with reporter nucleic acid. For example, the released portions of the probe nucleic acid, if present, can be transferred from one well of a microtiter plate (e.g., a 96-well plate) that contained the probe nucleic acid to another well of a microtiter plate that contains the reporter nucleic acid. The reporter nucleic acid can be designed to have a double-stranded portion with a restriction endonuclease cut site for the amplifying restriction endonuclease of the probe nucleic acid. This restriction endonuclease cut site for the amplifying restriction endonuclease can be referred to as an amplifying restriction endonuclease cut site. If portions of the probe nucleic acid containing the amplifying restriction endonuclease are present and placed in contact with the reporter nucleic acid, then the reporter nucleic acid can be cleaved at the amplifying restriction endonuclease cut site by the amplifying restriction endonuclease. Since the amplifying restriction endonucleases of the released portions of the probe nucleic acid are free to carry out repeated cleavage events, the number of reporter nucleic acid molecules that are cleaved can greatly exceed the number of amplifying restriction endonucleases present in the reaction. For example, the number of cleaved reporter nucleic acid molecules can greatly exceed (e.g., exponentially exceed) the number of amplifying restriction endonucleases present in the reaction and therefore can greatly exceed (e.g., exponentially exceed) the number of target nucleic acid molecules that were present in the sample contacted with the probe nucleic acid. Such a greatly expanded relationship (e.g., an exponential relationship) can allow very small amounts of target nucleic acid present in the sample to be readily detected.

After the released portions of the probe nucleic acid, if present, are contacted with the reporter nucleic acid, the presence or absence of cleaved reporter nucleic acid can be determined. The presence of cleaved reporter nucleic acid can indicate that the sample contained the target nucleic acid, thereby indicating that the sample contained the target microorganism or virus for which the sample is being tested, while the absence of cleaved reporter nucleic acid can indicate that the sample lacked the target nucleic acid, thereby indicating that the sample lacked the target microorganism or virus for which the sample is being tested. In some cases, the amount of cleaved reporter nucleic acid can be determined. In such cases, the amount of cleaved reporter nucleic acid can indicate the amount of target nucleic acid present in the sample, which can indicated the amount or level of contamination by the target microorganism or virus for which the sample is being tested. A standard curve using known amounts of target nucleic acid or known amounts target microorganisms or viruses can be used to aid in the determination of the amount of target nucleic acid or target microorganisms or viruses present within a sample.

In some cases, the reporter nucleic acid can contain a label to aid in the detection of cleaved reporter nucleic acid. For example, reporter nucleic acid can contain a fluorescent label and a quencher such that cleaved reporter nucleic acid provides a fluorescent signal and uncleaved reporter nucleic acid does not provide a fluorescent signal. In some cases, the reporter nucleic acid can contain a label (e.g., a colorimetric label, a fluorescent label or an enzyme (e.g., a redox enzyme) such as horse radish peroxidase) and can be attached to a solid support (e.g., a well of a microtiter plate). For example, the reporter nucleic acid can be attached to a solid support such that cleavage at the amplifying restriction endonuclease cut site by the amplifying restriction endonuclease releases a portion of the reporter nucleic acid that contains the label. The resulting reaction mixture can be collected and assessed for the presence, absence, or amount of released portions of the reporter nucleic acid using the label. For example, the released portions of the reporter nucleic acid, if present, can be transferred from one well of a microtiter plate (e.g., a 96-well plate) that contained the reporter nucleic acid to another well of a microtiter plate, where the transferred material can be assessed for a signal from the label.

One example of a method of detecting target nucleic acid that includes using probe nucleic acid and reporter nucleic acid is set forth in FIG. 1. With reference to FIG. 1, first reaction chamber 100 (e.g., a microtiter plate well) can contain probe nucleic acid 101. Probe nucleic acid 101 can be attached (e.g., immobilized) to solid support 102 and can include amplifying restriction endonuclease 103 (Ra). Probe nucleic acid 101 can be attached to solid support 102 such that amplifying restriction endonuclease 103 is released from solid support 102 upon cleavage of a nucleic acid component of probe nucleic acid 101. Probe nucleic acid 101 can have a single-stranded section having a nucleotide sequence that is complementary to at least a portion of target nucleic acid 104. Probe nucleic acid 101 can be contacted with a sample that may or may not contain target nucleic acid 104. If target nucleic acid 104 is present, at least a portion of target nucleic acid 104 and probe nucleic acid 101 can hybridize to form a double-stranded section of nucleic acid. Such a double-stranded section can contain at least one recognition restriction endonuclease cut site 105. Addition of recognition restriction endonuclease 106 (Rr) to first reaction chamber 100 can result in the cleave of probe nucleic acid 101 at recognition restriction endonuclease cut site 105 formed by one strand of probe nucleic acid and one strand of target nucleic acid, thereby releasing portion 107 of probe nucleic acid 101 from solid support 102. Portion 107 can include amplifying restriction endonuclease 103.

The reaction product from first reaction chamber 100 containing released portion 107, if target nucleic acid 104 was present, can be transferred (e.g., manually or automatically) to second reaction chamber 120. Second reaction chamber 120 can contain reporter nucleic acid 121. Reporter nucleic acid 121 can be attached (e.g., immobilized) to solid support 122 and can include marker (e.g., a label) 123 (M). Reporter nucleic acid 121 can be attached to solid support 122 such that marker 123 is released from solid support 122 upon cleavage of a nucleic acid component of reporter nucleic acid 121. Reporter nucleic acid 121 can have at least one double-stranded portion that contains at least one amplifying restriction endonuclease cut site 124. Addition of the reaction product from first reaction chamber 100 to second reaction chamber 120 can result in the cleavage of reporter nucleic acid 121 at amplifying restriction endonuclease cut site 124 if the reaction product contains portion 107. Such cleavage of reporter nucleic acid 121 can result in the release of portion 127 from solid support 122. Portion 127 can include marker 123.

The reaction product from second reaction chamber 120 can be assessed to determine the presence, absence, or amount of portion 127. The presence of portion 127 can indicate that the sample contained target nucleic acid 104, while the absence of portion 127 can indicate that the sample lacked target nucleic acid 104. In some cases, the amount of portion 127 can be determined. In such cases, the amount of portion 127 can indicate the amount of target nucleic acid 104 present in the sample. The presence, absence, or amount of portion 127 can be determined using marker 123, and portion 127 having marker 123 can be distinguished from uncleaved reporter nucleic acid 121 having marker 123 since, in this example, portion 127 is released from solid support 122, while uncleaved reporter nucleic acid 121 remains attached to solid support 122. For example, in some cases, the reaction product from second reaction chamber 120 can be transferred to third reaction chamber where the presence or absence of portion 127 via marker 123 is assessed. If portion 127 is present, the amount of portion 127 present can be quantified.

Figure 2:
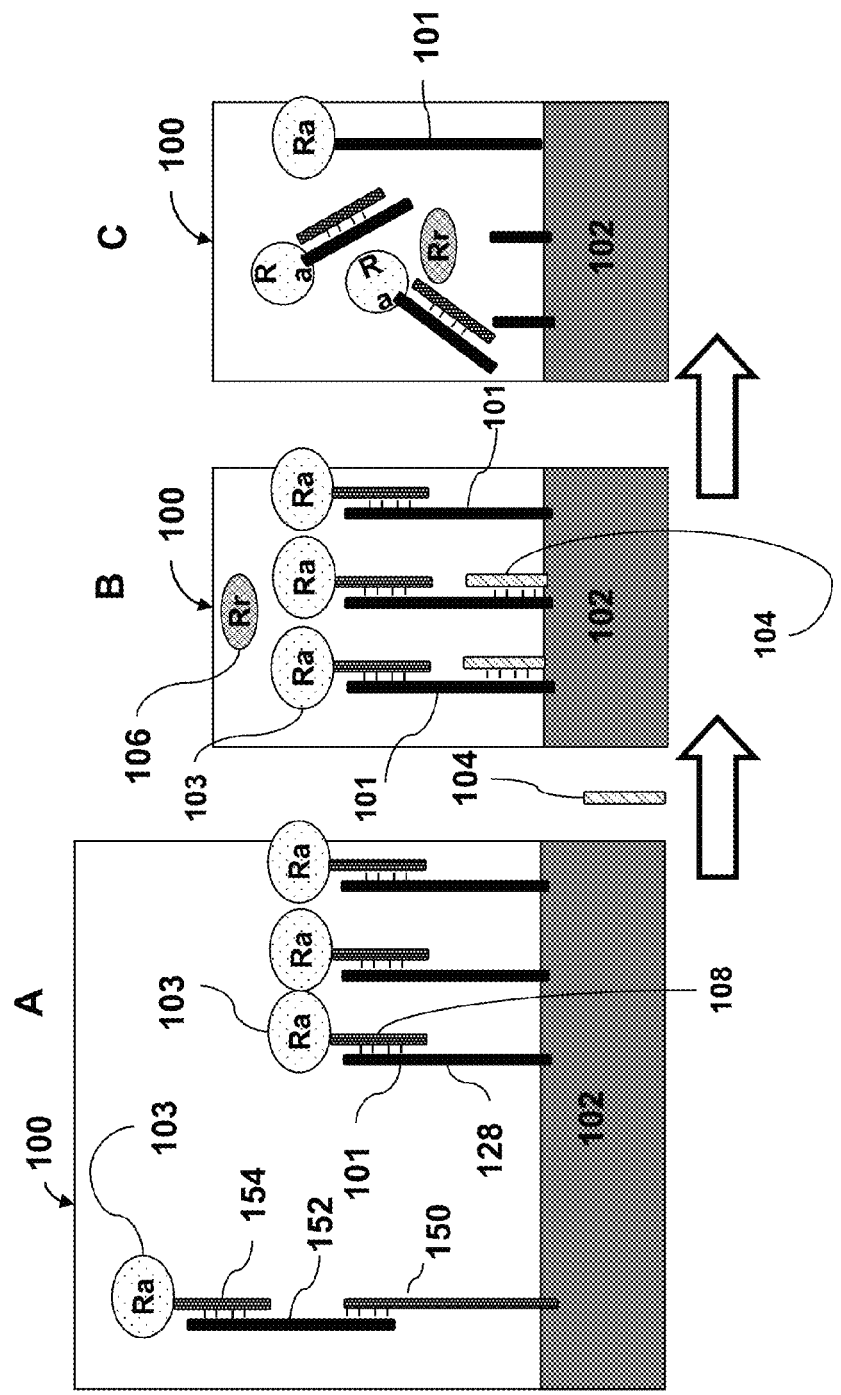
FIG. 2 is a schematic of an exemplary configuration of probe nucleic acid that can be used with the methods and materials provided herein for detecting target nucleic acid.

Probe nucleic acid 101 and reporter nucleic acid 121 can have various configurations. For example, with reference to FIG. 1, probe nucleic acid 101 can be designed to have a single nucleic acid strand such that the entire nucleic acid component of probe nucleic acid 101 is single-stranded prior to contact with target nucleic acid 104. In another example, with reference to FIG. 2, probe nucleic acid 101 can be designed to have first strand 128 and second strand 108. First strand 128 can be attached to solid support 102 and can be designed to have a single-stranded section having a nucleotide sequence that is complementary to at least a portion of target nucleic acid 104. Second strand 108 can include amplifying restriction endonuclease 103 and can have a single-stranded section having a nucleotide sequence that can hybridize to first strand 128. In some cases, first strand 128 and second strand 108 can be synthesized or obtained separately and then mixed together to form probe nucleic acid 101. For example, first strand 128 can be synthesized, biotinylated, and attached to a streptavidin-coated solid support. After synthesizing the nucleic acid component of second strand 108 and attaching amplifying restriction endonuclease 103 to the synthesized nucleic acid component, second strand 108 can be incubated with first strand 128 to form nucleic acid probe 101. In some cases, probe nucleic acid 101 can contain more than two strands. For example, probe nucleic acid can include first strand 150, second strand 152, and third strand 154. In this case, first strand 150 can be attached to solid support 102, second strand 152 can be hybridized to first strand 150 and can include a single-stranded section having a nucleotide sequence that is complementary to at least a portion of target nucleic acid 104, and third strand 154 can be hybridized to second strand 152 and can be attached to amplifying restriction endonuclease 103. Similar one, two, three, or more strand configurations can be used to make reporter nucleic acid.

In another embodiment, a method for detecting target nucleic acid can include contacting a sample (e.g., a sample to be tested or suspected to contain target nucleic acid) with probe nucleic acid. The probe nucleic acid can be designed to have a single-stranded portion with a nucleotide sequence that is complementary to at least a portion of the target nucleic acid to be detected. In this case, target nucleic acid present within the sample can hybridize with the complementary sequence of this single-stranded portion of the probe nucleic acid to form a double-stranded section with one strand being target nucleic acid and the other strand being probe nucleic acid. In addition, the single-stranded portion of the probe nucleic acid having the nucleotide sequence that is complementary to at least a portion of the target nucleic acid to be detected can be designed such that hybridization with the target nucleic acid creates a recognition restriction endonuclease cut site. Thus, target nucleic acid present within the sample can hybridize with the complementary sequence of the single-stranded portion of the probe nucleic acid to form a double-stranded section that creates a recognition restriction endonuclease cut site for a recognition restriction endonuclease. The probe nucleic acid also can be designed to contain an amplifying restriction endonuclease. Since this method includes the use of two or more different amplifying restriction endonucleases, the amplifying restriction endonuclease that is a component of the probe nucleic acid can be referred to as a first or an initial amplifying restriction endonuclease, with additional amplifying restriction endonucleases being referred to as second, third, and so on or secondary, tertiary, and so on amplifying restriction endonucleases. This initial amplifying restriction endonuclease is typically a different restriction endonuclease than the restriction endonuclease that is used as a recognition restriction endonuclease. For example, when an EcoRI restriction endonuclease is used as a recognition restriction endonuclease, a restriction endonuclease other than an EcoRI restriction endonuclease (e.g., a Hind III restriction endonuclease) is used as an initial amplifying restriction endonuclease. Thus, in general, probe nucleic acid is designed to contain an initial amplifying restriction endonuclease and to have a nucleotide sequence such that the target nucleic acid can hybridize to the probe nucleic acid and create a recognition restriction endonuclease cut site for a recognition restriction endonuclease. In some cases, the probe nucleic acid can be attached to a solid support (e.g., a well of a microtiter plate). For example, the probe nucleic acid can be attached to a solid support such that cleavage at the recognition restriction endonuclease cut site via the recognition restriction endonuclease releases a portion of the probe nucleic acid that contains the initial amplifying restriction endonuclease.

After contacting the sample that may or may not contain target nucleic acid with the probe nucleic acid that is attached to a solid support, the target nucleic acid, if present in the sample, can hybridize to the probe nucleic acid and create the recognition restriction endonuclease cut site. At this point, the recognition restriction endonuclease, whether added to the reaction or already present in the reaction, can cleave the probe nucleic acid at the recognition restriction endonuclease cut sites that are formed by the hybridization of target nucleic acid to the probe nucleic acid, thereby releasing the portion of the probe nucleic acid that contains the initial amplifying restriction endonuclease from the solid support. The number of initial amplifying restriction endonuclease-containing portions of the probe nucleic acid that are released from the solid support can be in an essentially linear relationship (e.g., essentially a one-for-one relationship) with the number of target nucleic acid molecules that hybridize with the probe nucleic acid to form the recognition restriction endonuclease cut site.

The portions of the probe nucleic acid containing the initial amplifying restriction endonuclease that were released from the solid support can be collected and placed in contact with first signal expansion nucleic acid and second signal expansion nucleic acid. The first signal expansion nucleic acid can be designed to have a double-stranded portion with a restriction endonuclease cut site for the initial amplifying restriction endonuclease of the probe nucleic acid. This restriction endonuclease cut site for the initial amplifying restriction endonuclease can be referred to as an initial amplifying restriction endonuclease cut site. The first signal expansion nucleic acid also can be designed to contain a secondary amplifying restriction endonuclease. The second signal expansion nucleic acid can be designed to have a double-stranded portion with a restriction endonuclease cut site for the secondary amplifying restriction endonuclease of the first signal expansion nucleic acid. This restriction endonuclease cut site for the secondary amplifying restriction endonuclease can be referred to as a secondary amplifying restriction endonuclease cut site. The second signal expansion nucleic acid also can be designed to contain an initial amplifying restriction endonuclease. For example, when an EcoRI restriction endonuclease is used as a recognition restriction endonuclease and a HindIII restriction endonuclease is used as an initial amplifying restriction endonuclease of the probe nucleic acid, a SmaI restriction endonuclease can be used as a secondary amplifying restriction endonuclease of the first signal expansion nucleic acid and a HindIII restriction endonuclease can be used as the initial amplifying restriction endonuclease of the second signal expansion nucleic acid.

In some cases, the first signal expansion nucleic acid and second signal expansion nucleic acid can be attached to a solid support (e.g., a well of a microtiter plate). For example, the first signal expansion nucleic acid can be attached to a solid support such that cleavage at the initial amplifying restriction endonuclease cut site via the initial amplifying restriction endonuclease releases a portion of the first signal expansion nucleic acid that contains the secondary amplifying restriction endonuclease, and the second signal expansion nucleic acid can be attached to a solid support such that cleavage at the secondary amplifying restriction endonuclease cut site via the secondary amplifying restriction endonuclease releases a portion of the second signal expansion nucleic acid that contains the initial amplifying restriction endonuclease. The first signal expansion nucleic acid can be attached to the same solid support (e.g., two different subcompartments of a larger compartment) that contains the second signal expansion nucleic acid provided that the secondary amplifying restriction endonuclease of uncleaved first signal expansion nucleic acid is unable to cleave the second signal expansion nucleic acid and provided that the initial amplifying restriction endonuclease of uncleaved second signal expansion nucleic acid is unable to cleave the first signal expansion nucleic acid. In some cases, the first signal expansion nucleic acid can be attached to the same solid support within a joint compartment such that the first signal expansion nucleic acid is within a first compartment of the joint compartment and the second signal expansion nucleic acid is within a second compartment of the joint compartment. In such cases, the secondary amplifying restriction endonuclease of uncleaved first signal expansion nucleic acid in the first compartment is unable to cleave the second signal expansion nucleic acid located in the second compartment, while the secondary amplifying restriction endonuclease of cleaved first signal expansion nucleic acid is capable of moving (e.g., diffusing) from the first compartment to the second compartment to cleave the second signal expansion nucleic acid located in the second compartment. In addition, the initial amplifying restriction endonuclease of uncleaved second signal expansion nucleic acid in the second compartment is unable to cleave the first signal expansion nucleic acid located in the first compartment, while the initial amplifying restriction endonuclease of cleaved second signal expansion nucleic acid is capable of moving (e.g., diffusing) from the second compartment to the first compartment to cleave the first signal expansion nucleic acid located in the first compartment.

If portions of the probe nucleic acid containing the initial amplifying restriction endonuclease are present and placed in contact with the first signal expansion nucleic acid, then the first signal expansion nucleic acid can be cleaved at the initial amplifying restriction endonuclease cut site by the initial amplifying restriction endonuclease, thereby releasing a portion of the first signal expansion nucleic acid that contains the secondary amplifying restriction endonuclease from the solid support. The released portions of the first signal expansion nucleic acid containing the secondary amplifying restriction endonuclease can be free to cleave the second signal expansion nucleic acid at the secondary amplifying restriction endonuclease cut site, thereby releasing a portion of the second signal expansion nucleic acid that contains the initial amplifying restriction endonuclease from the solid support. Since the initial amplifying restriction endonucleases of the released portions of the probe nucleic acid, the initial amplifying restriction endonucleases of the released portions of the second signal expansion nucleic acid, and the secondary amplifying restriction endonucleases of the released portions of the first signal expansion nucleic acid are free to carry out repeated cleavage events, the number of released portions containing the initial amplifying restriction endonucleases is greatly increased from the number that were released by the recognition restriction endonuclease. For example, the number of cleaved first signal expansion nucleic acid molecules can greatly exceed (e.g., exponentially exceed) the number of released portions of the probe nucleic acid, and the number of cleaved second signal expansion nucleic acid molecules can greatly exceed (e.g., exponentially exceed) the number of released portions of the probe nucleic acid. Such a greatly expanded relationship (e.g., an exponential relationship) can allow very small amounts of target nucleic acid present in the sample to be readily detected.

In some cases, this method can be performed with the first signal expansion nucleic acid being attached to a solid support that is different from the solid support that contains the second signal expansion nucleic acid. For example, the first signal expansion nucleic acid can be attached to one well of a microtiter plate, while the second signal expansion nucleic acid can be attached to a different well of a microtiter plate. In this case, the resulting reaction material from the well with the first signal expansion nucleic acid can be collected and transferred to the well containing the second signal expansion nucleic acid.

The portions of the second signal expansion nucleic acid containing the initial amplifying restriction endonuclease that were released from the solid support containing the second signal expansion nucleic acid along with any other released portions in this reaction (e.g., the released portions of the probe nucleic acid containing the initial amplifying restriction endonuclease and the released portions of the first signal expansion nucleic acid containing the secondary amplifying restriction endonuclease) can be collected and placed in contact with reporter nucleic acid. For example, the released portions, if present, can be transferred from one well of a microtiter plate (e.g., a 96-well plate) that contained the second signal expansion nucleic acid to another well of a microtiter plate that contains the reporter nucleic acid. The reporter nucleic acid can be designed to have a double-stranded portion with a restriction endonuclease cut site for the initial amplifying restriction endonuclease. If released portions containing the initial amplifying restriction endonuclease are present and placed in contact with the reporter nucleic acid, then the reporter nucleic acid can be cleaved at the initial amplifying restriction endonuclease cut site by the initial amplifying restriction endonuclease. Since the initial amplifying restriction endonucleases of the released portions are free to carry out repeated cleavage events, the number of reporter nucleic acid molecules that are cleaved can greatly exceed the number of initial amplifying restriction endonucleases present in the reaction. For example, the number of cleaved reporter nucleic acid molecules can greatly exceed (e.g., exponentially exceed) the number of initial amplifying restriction endonucleases present in the reaction and therefore can greatly exceed (e.g., exponentially exceed) the number of target nucleic acid molecules that were present in the sample contacted with the probe nucleic acid. Such a greatly expanded relationship (e.g., an exponential relationship) can allow very small amounts of target nucleic acid present in the sample to be readily detected.

After the released portions containing the initial amplifying restriction endonuclease, if present, are contacted with the reporter nucleic acid, the presence or absence of cleaved reporter nucleic acid can be determined. The presence of cleaved reporter nucleic acid can indicate that the sample contained the target nucleic acid, thereby indicating that the sample contained the target microorganism or virus for which the sample is being tested, while the absence of cleaved reporter nucleic acid can indicate that the sample lacked the target nucleic acid, thereby indicating that the sample lacked the target microorganism or virus for which the sample is being tested.

In some cases, the amount of cleaved reporter nucleic acid can be determined. In such cases, the amount of cleaved reporter nucleic acid can indicate the amount of target nucleic acid present in the sample, which can indicated the amount or level of contamination by the target microorganism or virus for which the sample is being tested. A standard curve using known amounts of target nucleic acid or known amounts target microorganisms or viruses can be used to aid in the determination of the amount of target nucleic acid or target microorganisms or viruses present within a sample.

In some cases, the reporter nucleic acid can contain a label to aid in the detection of cleaved reporter nucleic acid. For example, reporter nucleic acid can contain a fluorescent label and a quencher such that cleaved reporter nucleic acid provides a fluorescent signal and uncleaved reporter nucleic acid does not provide a fluorescent signal. In some cases, the reporter nucleic acid can contain a label (e.g., a colorimetric label, fluorescent label or an enzyme such as horse radish peroxidase) and can be attached to a solid support (e.g., a well of a microtiter plate). For example, the reporter nucleic acid can be attached to a solid support such that cleavage at the initial amplifying restriction endonuclease cut site by the initial amplifying restriction endonuclease releases a portion of the reporter nucleic acid that contains the label. The resulting reaction mixture can be collected and assessed for the presence, absence, or amount of released portions of the reporter nucleic acid using the label. For example, the released portions of the reporter nucleic acid, if present, can be transferred from one well of a microtiter plate (e.g., a 96-well plate) that contained the reporter nucleic acid to another well of a microtiter plate, where the transferred material can be assessed for a signal from the label.

In some cases, the presence or absence of cleaved first signal expansion nucleic acid, cleaved second signal expansion nucleic acid, or both can be determined. The presence of such cleaved nucleic acid can indicate that the sample contained the target nucleic acid, thereby indicating that the sample contained the target microorganism or virus for which the sample is being tested, while the absence of such cleaved nucleic acid can indicate that the sample lacked the target nucleic acid, thereby indicating that the sample lacked the target microorganism or virus for which the sample is being tested. In some cases, the amount of cleaved first signal expansion nucleic acid, cleaved second signal expansion nucleic acid, or both can be determined. In such cases, the amount of cleaved nucleic acid can indicate the amount of target nucleic acid present in the sample, which can indicated the amount or level of contamination by the target microorganism or virus for which the sample is being tested. In these cases, the use of cleaved first signal expansion nucleic acid, cleaved second signal expansion nucleic acid, or both to assess the sample for target nucleic acid can be in addition to the use of a separate reporter nucleic acid step or can replace the use of a separate reporter nucleic acid step. In some cases, the first signal expansion nucleic acid, the second signal expansion nucleic acid, or both can be labeled in a manner similar to that described herein for the reporter nucleic acid to aid in detection. When the presence, absence, or amount of cleaved first signal expansion nucleic acid, cleaved second signal expansion nucleic acid, or both are determined to assess the sample for target nucleic acid, the first signal expansion nucleic acid can be referred to as a first reporter nucleic acid and the second signal expansion nucleic acid can be referred to as a second reporter nucleic acid even though they include amplifying restriction endonucleases. A standard curve using known amounts of target nucleic acid or known amounts target microorganisms or viruses can be used to aid in the determination of the amount of target nucleic acid or target microorganisms or viruses present within a sample.

Figure 3:
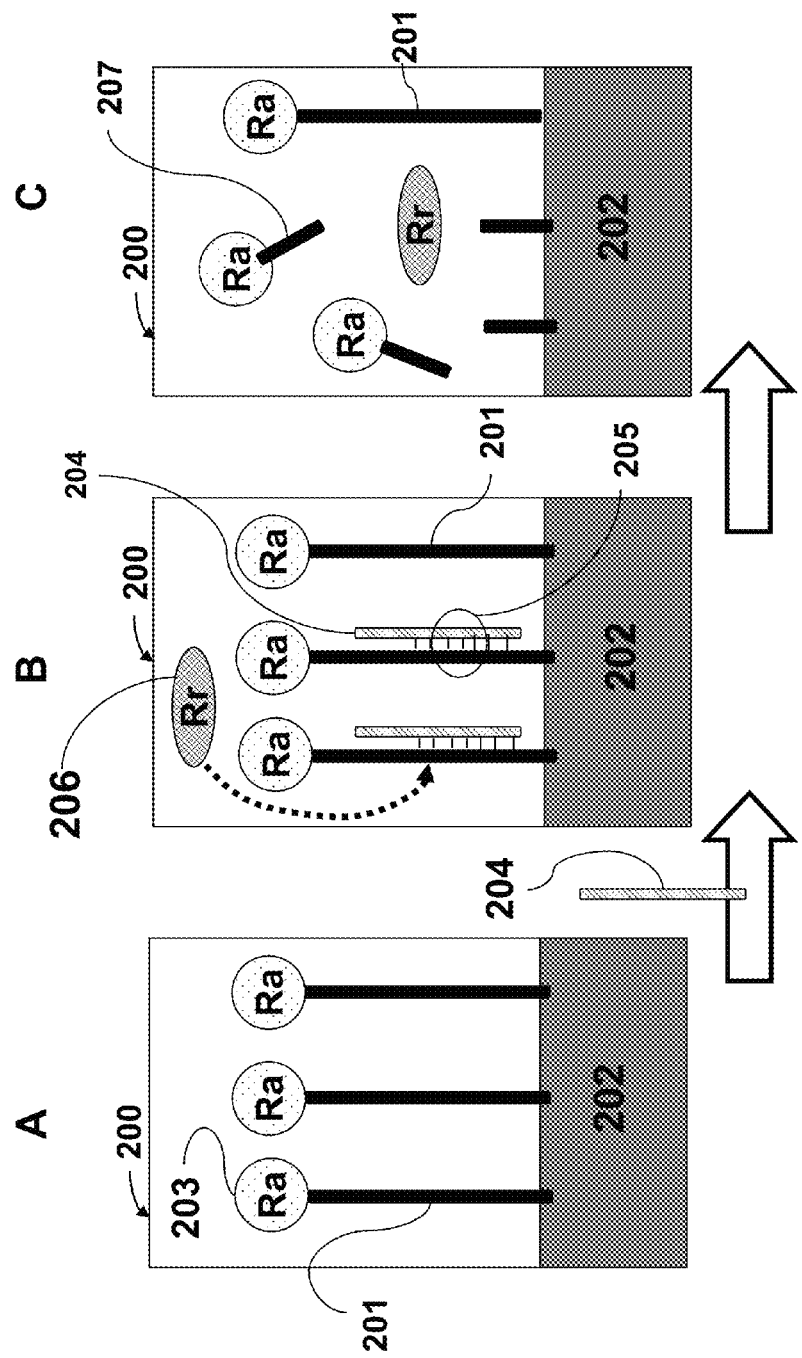
FIG. 3 is a schematic depicting an exemplary method for detecting target nucleic acid using probe nucleic acid, a recognition restriction endonuclease, first signal expansion nucleic acid, second signal expansion nucleic acid, and reporter nucleic acid.

Examples of a method of detecting target nucleic acid that includes using probe nucleic acid, first signal expansion nucleic acid, second signal expansion nucleic acid, and reporter nucleic acid are set forth in FIGS. 3-5. With reference to FIG. 3, first reaction chamber 200 (e.g., a microtiter plate well) can contain probe nucleic acid 201. Probe nucleic acid 201 can be attached (e.g., immobilized) to solid support 202 and can include initial amplifying restriction endonuclease 203 (Ra). Probe nucleic acid 201 can be attached to solid support 202 such that initial amplifying restriction endonuclease 203 is released from solid support 202 upon cleavage of a nucleic acid component of probe nucleic acid 201. Probe nucleic acid 201 can have a single-stranded section having a nucleotide sequence that is complementary to at least a portion of target nucleic acid 204. Probe nucleic acid 201 can be contacted with a sample that may or may not contain target nucleic acid 204. If target nucleic acid 204 is present, at least a portion of target nucleic acid 204 and probe nucleic acid 201 can hybridize to form a double-stranded section of nucleic acid. Such a double-stranded section can contain at least one recognition restriction endonuclease cut site 205. Addition of recognition restriction endonuclease 206 (Rr) to first reaction chamber 200 can result in the cleavage of probe nucleic acid 201 at recognition restriction endonuclease cut site 205 formed by one strand of probe nucleic acid and one strand of target nucleic acid, thereby releasing portion 207 of probe nucleic acid 201 from solid support 202. Portion 207 can include initial amplifying restriction endonuclease 203.

The reaction product from first reaction chamber 200 containing released portion 207, if target nucleic acid 204 was present, can be transferred (e.g., manually or automatically) to second reaction chamber 220. Second reaction chamber 220 can contain first signal expansion nucleic acid 226 and second signal expansion nucleic acid 225. First signal expansion nucleic acid 226 can have at least one double-stranded portion that contains at least one initial amplifying restriction endonuclease cut site 230. First signal expansion nucleic acid 226 can be attached (e.g., immobilized) to solid support 222 and can include secondary amplifying restriction endonuclease 223 (Rb). First signal expansion nucleic acid 226 can be attached to solid support 222 such that portion 234 containing secondary amplifying restriction endonuclease 223 is released from solid support 222 upon cleavage of first signal expansion nucleic acid 226 at initial amplifying restriction endonuclease cut site 230. For clarity, frame E of FIG. 3 omits depicting one strand from the cleaved versions of first signal expansion nucleic acid 226 and second signal expansion nucleic acid 225.

Second signal expansion nucleic acid 225 can have at least one double-stranded portion that contains at least one secondary amplifying restriction endonuclease cut site 232. Second signal expansion nucleic acid 225 can be attached (e.g., immobilized) to solid support 222 and can include initial amplifying restriction endonuclease 224. Second signal expansion nucleic acid 225 can be attached to solid support 222 such that portion 236 containing initial amplifying restriction endonuclease 224 is released from solid support 222 upon cleavage of second signal expansion nucleic acid 225 at secondary amplifying restriction endonuclease cut site 232. Initial amplifying restriction endonuclease 203 of probe nucleic acid 201 and initial amplifying restriction endonuclease 224 of second signal expansion nucleic acid 225 can be the same restriction endonuclease. For example, both can be an EcoRI restriction endonuclease.

Addition of the reaction product from first reaction chamber 200 to second reaction chamber 220 can result in the cleavage of first signal expansion nucleic acid 226 at initial amplifying restriction endonuclease cut site 230 if the reaction product contains portion 207. Such cleavage of first signal expansion nucleic acid 226 can result in the release of portion 234 from solid support 222. Portion 234, which can include secondary amplifying restriction endonuclease 223, can result in the cleavage of second signal expansion nucleic acid 225 at secondary amplifying restriction endonuclease cut site 232. Such cleavage of second signal expansion nucleic acid 225 can result in the release of portion 236 from solid support 222. Thus, this reaction can result in the accumulation of released portions 234 and 236.

The reaction product from second reaction chamber 220 containing released portion 207, released portion 234, and released portion 236, if target nucleic acid 204 was present, can be transferred (e.g., manually or automatically) to third reaction chamber 240. Third reaction chamber 240 can contain reporter nucleic acid 241. Reporter nucleic acid 241 can be attached (e.g., immobilized) to solid support 242 and can include marker (e.g., a label) 243 (M). Reporter nucleic acid 241 can be attached to solid support 242 such that marker 243 is released from solid support 242 upon cleavage of a nucleic acid component of reporter nucleic acid 241. Reporter nucleic acid 241 can have at least one double-stranded portion that contains at least one initial amplifying restriction endonuclease cut site 246. Addition of the reaction product from second reaction chamber 220 to third reaction chamber 240 can result in the cleavage of reporter nucleic acid 241 at initial amplifying restriction endonuclease cut site 246 if the reaction product contains portion 207 and portion 236. In some cases, reporter nucleic acid 241 can include at least one double-stranded portion that contains at least one cut site for secondary amplifying restriction endonuclease 223. In such cases, addition of the reaction product from second reaction chamber 220 to third reaction chamber 240 can result in the cleavage of reporter nucleic acid 241 at the cut site for secondary amplifying restriction endonuclease 223 if the reaction product contains portion 234. Cleavage of reporter nucleic acid 241 can result in the release of portion 247 from solid support 242. Portion 247 can include marker 243.

The reaction product from third reaction chamber 240 can be assessed to determine the presence, absence, or amount of portion 247. The presence of portion 247 can indicate that the sample contained target nucleic acid 204, while the absence of portion 247 can indicate that the sample lacked target nucleic acid 204. In some cases, the amount of portion 247 can be determined. In such cases, the amount of portion 247 can indicate the amount of target nucleic acid 204 present in the sample. The presence, absence, or amount of portion 247 can be determined using marker 243, and portion 247 having marker 243 can be distinguished from uncleaved reporter nucleic acid 241 having marker 243 since, in this example, portion 247 is released from solid support 242, while uncleaved reporter nucleic acid 241 remains attached to solid support 242. For example, in some cases, the reaction product from third reaction chamber 24 can be transferred to fourth reaction chamber where the presence or absence of portion 247 via marker 243 is assessed. If portion 347 is present, the amount of portion 247 present can be quantified.

In some cases and with reference to FIGS. 4 and 5, first signal expansion nucleic acid 226 can include marker (e.g., a label) 243 (M) and second signal expansion nucleic acid 225 can include marker (e.g., a label) 243 (M). In such cases, cleavage of first signal expansion nucleic acid 226 and cleavage of second signal expansion nucleic acid 225 can be assessed using marker 243 to determine the presence, absence, or amount of target nucleic acid within a sample. For example, detector 250 can be used to detect marker 243 released from solid support 222.

Probe nucleic acid 201, first signal expansion nucleic acid 226, second signal expansion nucleic acid 225, and reporter nucleic acid 241 can have various configurations. For example, with reference to FIG. 3, probe nucleic acid 201 can be designed to have a single nucleic acid strand such that the entire nucleic acid component of probe nucleic acid 201 is single-stranded prior to contact with target nucleic acid 204. In another example, probe nucleic acid 201 can be designed in a manner like probe nucleic acid 101 to have two or more strands. See, e.g., FIG. 2. For example, probe nucleic acid 201 can have a first strand and a second strand. The first strand can be attached to a solid support and can be designed to have a single-stranded section having a nucleotide sequence that is complementary to at least a portion of target nucleic acid. The second strand can include an initial amplifying restriction endonuclease and can have a single-stranded section having a nucleotide sequence that can hybridize to the first strand. In some cases, the first strand and second strand can be synthesized or obtained separately and then mixed together to form probe nucleic acid 201. For example, the first strand can be synthesized, biotinylated, and attached to a streptavidin-coated solid support. After synthesizing the nucleic acid component of the second strand and attaching an initial amplifying restriction endonuclease to the synthesized nucleic acid component, the second strand can be incubated with the first strand to form nucleic acid probe 201. In some cases, probe nucleic acid 201 can contain more than two strands. For example, probe nucleic acid can include a first strand, a second strand, and a third strand. In this case, the first strand can be attached to a solid support, the second strand can be hybridized to the first strand and can include a single-stranded section having a nucleotide sequence that is complementary to at least a portion of target nucleic acid, and the third strand can be hybridized to the second strand and can be attached to an initial amplifying restriction endonuclease. Similar one, two, three, or more strand configurations can be used to make first signal expansion nucleic acid, second signal expansion nucleic acid, or reporter nucleic acid. For example, first signal expansion nucleic acid and second signal expansion nucleic acid can be designed to have a configuration as shown in FIG. 4 or 5.

Probe nucleic acid described herein typically includes at least one single-stranded DNA section that is designed to hybridize with a desired target nucleic acid and thereby create a recognition restriction endonuclease cut site. The other portions of the probe nucleic acid can include DNA, RNA, or other molecules. For example, probe nucleic acid can include biotin such that the probe nucleic acid can be attached to a streptavidin-coated solid support. In some cases, the single-stranded section of the probe nucleic acid that is designed to hybridize with a desired target nucleic acid and create a recognition restriction endonuclease cut site can be RNA or a nucleic acid analog (e.g., a peptide nucleic acid (PNA)) provided that such a single-stranded section can (i) hybridize with the desired target nucleic acid and (ii) create a recognition restriction endonuclease cut site with the complementary target nucleic acid sequence that is capable of being cleaved by the recognition restriction endonuclease. Examples of restriction endonucleases that can be used as recognition restriction endonucleases to cleave a recognition restriction endonuclease cut site that is created between an RNA section of the probe nucleic acid and a DNA section of the target nucleic acid include, without limitation, HhaI, AluI, TaqI, HaeIII, EcoRI, HindII, SalI, and MspI restriction endonucleases.

Probe nucleic acid described herein can be any length provided that the single-stranded section of the probe nucleic acid that is designed to hybridize with a desired target nucleic acid is capable of hybridizing to the target nucleic acid and provided that the amplifying restriction endonuclease of the probe nucleic acid is capable of cleaving its amplifying restriction endonuclease cut site after the probe nucleic acid is cleaved by a recognition restriction endonuclease. In general, the single-stranded section of the probe nucleic acid that is designed to hybridize with a desired target nucleic acid can be between about 10 and about 500 or more nucleotides (e.g., between about 10 and about 400 nucleotides, between about 10 and about 300 nucleotides, between about 10 and about 200 nucleotides, between about 10 and about 100 nucleotides, between about 10 and about 50 nucleotides, between about 10 and about 25 nucleotides, between about 20 and about 500 nucleotides, between about 30 and about 500 nucleotides, between about 40 and about 500 nucleotides, between about 50 and about 500 nucleotides, between about 15 and about 50 nucleotides, between about 15 and about 25 nucleotides, between about 20 and about 50 nucleotides, between about 18 and about 25 nucleotides, between about 20 and about 60 nucleotides, between about 25 and about 55 nucleotides, between about 30 and about 50 nucleotides, between about 35 and about 45 nucleotides, or between about 38 and about 42 nucleotides) in length. The recognition restriction endonuclease cut site that will be created by the hybridization of target nucleic acid to this single-stranded section of the probe nucleic acid can be located at any position alone the single-stranded section. For example, the recognition restriction endonuclease cut site to be created can be towards the 5' end, towards the '3 end, or near the center of the single-stranded section of the probe nucleic acid. In general, the overall length of the probe nucleic acid described herein can be between about 10 and about 2500 or more nucleotides (e.g., between about 10 and about 2000 nucleotides, between about 10 and about 1000 nucleotides, between about 10 and about 500 nucleotides, between about 10 and about 400 nucleotides, between about 10 and about 300 nucleotides, between about 10 and about 200 nucleotides, between about 10 and about 100 nucleotides, between about 10 and about 50 nucleotides, between about 10 and about 25 nucleotides, between about 20 and about 500 nucleotides, between about 30 and about 500 nucleotides, between about 40 and about 500 nucleotides, between about 50 and about 500 nucleotides, between about 75 and about 500 nucleotides, between about 100 and about 500 nucleotides, between about 150 and about 500 nucleotides, between about 15 and about 50 nucleotides, between about 15 and about 25 nucleotides, between about 20 and about 50 nucleotides, between about 18 and about 25 nucleotides, between about 20 and about 60 nucleotides, between about 25 and about 55 nucleotides, between about 30 and about 50 nucleotides, between about 35 and about 45 nucleotides, or between about 38 and about 42 nucleotides) in length.

The recognition restriction endonuclease cut site to be created by hybridization of target nucleic acid to the probe nucleic acid can be a cut site of any type of restriction endonuclease. In addition, any type of restriction endonuclease can be used as a recognition restriction endonuclease to cleave probe nucleic acid upon target nucleic acid hybridization. Examples of restriction endonucleases that can be used as recognition restriction endonucleases include, without limitation, EcoRI, EcoRII, BamHI, HindIII, TaqI, NotI, HinfI, Sau3A, PovII, SmaI, HaeIII, HgaI, AluI, EcoRV, EcoP15I, KpnI, PstI, SacI, SalI, ScaI, SphI, StuI, XbaI, AarI, BanII, BseGI, BspPI, CfrI, EcoNI, Hsp92II, NlaIV, RsaI, TaiI, AasI, BbsI, BseJI, BspTI, ClaI, EcoO109I, I-PpoI, NmuCI, RsrII, TaqaI, AatII, BbuI, BseLI, BsrBI, CpoI, KasI, Acc65I, BbvCI, BseMI, BsrDI, Csp45I, Kpn2I, NruI, SacII, TasI, AccB7I, BbvI, BseMII, BsrFI, Csp6I, EheI, KpnI, NsbI, SalI, TatI, AccI, BceAI, BseNI, BsrGI, CspI, Esp3I, KspAI, NsiI, SapI, and TauI restriction endonucleases. In some cases, nucleic acid encoding a naturally-occurring restriction endonuclease can be genetically engineered to create a modified restriction endonuclease that has the ability to recognize a particular cut site. Common computer algorithms can be used to locate restriction endonuclease cut sites along the nucleotide sequence of any desired target nucleic acid. Once located, the sequence of the restriction endonuclease cut site along with additional flanking sequence (e.g., 5' flanking sequence, 3' flanking sequence, or both 5' and 3' flanking sequence) can be used to design the complementary sequence of the probe nucleic acid that is used to hybridize to the target nucleic acid and create the recognition restriction endonuclease cut site upon target nucleic acid hybridization. In some cases, a probe nucleic acid can be designed to have the restriction endonuclease cut site located in the middle or near the middle such that the restriction endonuclease cut site has both 5' and 3' flanking sequences that are complementary to the target nucleic acid.

In general, probe nucleic acid can be designed to have a single-stranded section that is designed to hybridize with desired target nucleic acid and to form a single recognition restriction endonuclease cut site upon target nucleic acid hybridization. In some cases, probe nucleic acid can be designed to have a single-stranded section that is designed to hybridize with desired target nucleic acid and to form more than one (e.g., two, three, four, five, six, seven, eight, nine, ten, or more) recognition restriction endonuclease cut site upon target nucleic acid hybridization. When more than one recognition restriction endonuclease cut site is used, the multiple recognition restriction endonuclease cut sites can be cut sites for the same restriction endonuclease or cut sites for different restriction endonucleases. For example, probe nucleic acid can be designed to have a single-stranded section that is designed to hybridize with desired target nucleic acid and to form one recognition restriction endonuclease cut site for an EcoRI recognition restriction endonuclease and one recognition restriction endonuclease cut site for an XbaI recognition restriction endonuclease upon target nucleic acid hybridization. In such cases, each recognition restriction endonuclease can be used individually or in combination (e.g., as a mixture) to cleave probe nucleic acid that hybridized to target nucleic acid and formed the corresponding recognition restriction endonuclease cut site via such hybridization.

Probe nucleic acid can be designed such that any target nucleic acid of a target microorganism or virus suspected of contaminating, for example, a food product can be detected. Examples of target nucleic acid that can be detected using the methods and materials provided herein include, without limitation, microbial DNA or RNA (e.g., bacterial, fungal, or protozoan DNA or RNA), methylated microbial DNA, and viral DNA or RNA. In some cases such as those involving assessing a sample for contamination by an RNA virus, the target nucleic acid can be an RNA or a cDNA generated from an RNA. When detecting an RNA target nucleic acid, restriction endonucleases having the ability to cleave a recognition restriction endonuclease cut site that is created between a DNA section of the probe nucleic acid and the RNA target nucleic acid can be used as recognition restriction endonucleases. Examples of such restriction endonucleases include, without limitation, HhaI, AluI, TaqI, HaeIII, EcoRI, HindII, SalI, and MspI restriction endonucleases. When detecting methylated target nucleic acid (e.g., a methylated target nucleic acid of a bacterial organism), restriction endonucleases having the ability to cleave a recognition restriction endonuclease cut site that includes a methylated nucleotide to be assessed can be used as recognition restriction endonucleases. Examples of restriction endonucleases having the ability to recognize methylated nucleotides include, without limitation, DpnI, GlaI, HpaII, MspI, AciI, HhaI, and SssI restriction endonucleases. In such cases, a control can include detecting the same target nucleic acid without the methylated nucleotide. In some cases, a combination of methylation insensitive and methylation sensitive restriction endonucleases can be used to assess a sample for methylated target nucleic acid. For example, similar generation of cleavage products using both methylation insensitive and methylation sensitive restriction endonucleases designed for the same site can indicate that the target nucleic acid lacks methylation at that site, while an increased level of cleavage products using a methylation insensitive restriction endonuclease as compared to the level generated using a methylation sensitive restriction endonuclease designed for the same site can indicate that the target nucleic acid is methylated at that site.

The nucleotide sequence of target nucleic acid to be detected can be obtained from, for example, common nucleic acid sequence databases such as GenBank®. A portion of target nucleic acid sequence can be selected using a computer-based program. For example, a computer-based program can be used to detect restriction endonuclease cut sites within a portion of target nucleic acid. Such information can be used to design probe nucleic acid such that the single-stranded section creates at least one recognition restriction endonuclease cut site upon hybridization of the target nucleic acid. In some cases, bioinformatics computer-based programs and tools can be used to assist in the design of probe nucleic acid. For example, computer programs (e.g., BLAST® and alignment programs) and computer databases (e.g., GenBank®) can be used to identify nucleic acid sequences from particular microorganisms and viruses and can be used to identify regions of high sequence similarity among various strains or variants of particular microorganisms and viruses. In addition, computer programs such as CLC Workbench or Vector NTI (Invitrogen) can be used to identify the location of restriction endonuclease cut sites within a particular nucleic acid sequence. In some cases, sequence analysis computer programs can be used to identify sequences with limited or an absence of repeats, a presence of high sequence complexity of a potential recognition restriction endonuclease cut site, and/or limited or an absence of hairpin structures. Identification of such sequences can help reduce the risk of probe self-hybridization and potentially unintended cutting by a recognition endonuclease.

Any appropriate method can be used to obtain the nucleic acid component of the probe nucleic acid. For example, common molecular cloning and chemical nucleic acid synthesis techniques can be used to obtain the nucleic acid component of the probe nucleic acid. In some cases, the nucleic acid component of the probe nucleic acid can be synthesized using commercially available automated oligonucleotide synthesizers such as those available from Applied Biosystems (Foster City, Calif.). In some cases, probe nucleic acids can be synthesized de novo using any of a number of procedures widely available in the art. Examples of such methods of synthesis include, without limitation, the β-cyanoethyl phosphoramidite method (Beaucage et al., *Tet. Let.,* 22:1859-1862 (1981)) and the nucleoside H-phosphonate method (Garegg et al., *Tet. Let.,* 27:4051-4054 (1986); Froehler et al., *Nucl. Acid Res.,* 14:5399-5407 (1986); Garegg et al., *Tet. Let.,* 27:4055-4058 (1986); and Gaffney et al., *Tet. Let.,* 29:2619-2622 (1988)). These methods can be performed by a variety of commercially-available automated oligonucleotide synthesizers. In some cases, recombinant nucleic acid techniques such as PCR and those that include using restriction enzyme digestion and ligation of existing nucleic acid sequences (e.g., genomic DNA or cDNA) can be used to obtain the nucleic acid component of the probe nucleic acid.

Probe nucleic acid described herein can be attached to a solid support. Examples of solid supports include, without limitation, a well of a microtiter plate (e.g., a 96-well microtiter plate or ELISA plate), beads (e.g., magnetic, glass, plastic, or gold-coated beads), slides (e.g., glass or gold-coated slides), micro- or nano-particles (e.g., carbon nanotubes), platinum solid supports, palladium solid supports, and a surface of a chamber or channel within a microfluidic device. In some cases, a solid support can be a silicon oxide-based solid support, a plastic polymer-based solid support (e.g., a nylon, nitrocellulose, or polyvinylidene fluoride-based solid support), or a biopolymer-based (e.g., a cross-linked dextran or cellulose-based solid support) solid support. Probe nucleic acid can be directly or indirectly attached to a solid support. For example, biotin can be a component of the probe nucleic acid, and the probe nucleic acid containing biotin can be indirectly attached to a solid support that is coated with streptavidin via a biotin-streptavidin interaction. In some cases, probe nucleic acid can be attached to a solid support via a covalent or non-covalent interaction. For example, probe nucleic acid can be covalently attached to magnetic beads as described elsewhere (Albretsen et al., *Anal. Biochem.,* 189 (1):40-50 (1990)).

Probe nucleic acid can be designed to contain any type of restriction endonuclease as an amplifying restriction endonuclease. In general, an amplifying restriction endonuclease of the probe nucleic acid is typically a different restriction endonuclease than the restriction endonuclease that is used as a recognition restriction endonuclease. For example, when an EcoRI restriction endonuclease is used as a recognition restriction endonuclease, a restriction endonuclease other than an EcoRI restriction endonuclease (e.g., a HindIII restriction endonuclease) is used as an amplifying restriction endonuclease. Examples of restriction endonucleases that can be used as amplifying restriction endonucleases include, without limitation, EcoRI, EcoRII, BamHI, HindIII, TaqI, NotI, HinfI, Sau3A, PovII, SmaI, HaeIII, HgaI, AluI, EcoRV, EcoP15I, KpnI, PstI, SacI, SalI, ScaI, SphI, StuI, XbaI, AarI, BanII, BseGI, BspPI, CfrI, EcoNI, Hsp92II, NlaIV, RsaI, TaiI, AasI, BbsI, BseJI, BspTI, ClaI, EcoO109I, I-PpoI, NmuCI, RsrII, TaqaI, AatII, BbuI, BseLI, BsrBI, CpoI, KasI, Acc65I, BbvCI, BseMI, BsrDI, Csp45I, Kpn2I, NruI, SacII, TasI, AccB7I, BbvI, BseMII, BsrFI, Csp6I, EheI, KpnI, NsbI, SalI, TatI, AccI, BceAI, BseNI, BsrGI, CspI, Esp3I, KspAI, NsiI, SapI, and TauI restriction endonucleases. Any number of molecules of the same amplifying restriction endonuclease can be attached to one probe nucleic acid molecule. For example, a single probe nucleic acid molecule can contain one, two, three, four, five, or more EcoRI amplifying restriction endonuclease molecules. In some cases, a single probe nucleic acid molecule can contain two or more (e.g., two, three, four, five, or more) different types of amplifying restriction endonucleases. For example, a single probe nucleic acid molecule can contain three EcoRI amplifying restriction endonuclease molecules and two BanII amplifying restriction endonuclease molecules.

Any appropriate method can be used to attach an amplifying restriction endonuclease to a nucleic acid component of the probe nucleic acid. In some cases, an amplifying restriction endonuclease can be attached by an ionic or covalent attachment. For example, covalent bonds such as amide bonds, disulfide bonds, and thioether bonds, or bonds formed by crosslinking agents can be used. In some cases, a non-covalent linkage can be used. The attachment can be a direct attachment or an indirect attachment. For example, a linker can be used to attach an amplifying restriction endonuclease to a nucleic acid component of the probe nucleic acid. In some cases, nucleic acid can include a thiol modification, and a restriction endonuclease can be conjugated to the thiol-containing nucleic acid based on succinimidyl 4-[N-maleimidomethyl]cyclohexane-1-carboxylate (SMCC) using techniques similar to those described elsewhere (Dill et al., *Biosensors and Bioelectronics,* 20:736-742 (2004)). In some cases, a biotinylated nucleic acid and a streptavidin-containing restriction endonuclease can be attached to one another via a biotin-streptavidin interaction. A restriction endonuclease can be conjugated with streptavidin using, for example, sulfosuccinimidyl 6-(3'-[2-pyridyldithio]-propionamido)hexanoate. An amplifying restriction endonuclease can be attached at any location of a nucleic acid component of the probe nucleic acid. For example, an amplifying restriction endonuclease can be attached at an end (e.g., a 5' end or 3' end) of a nucleic acid component, in the middle of a nucleic acid component, or at any position along the length of a nucleic acid component.

Signal expansion nucleic acid (e.g., first signal expansion nucleic acid and second signal expansion nucleic acid) and reporter nucleic acid described herein typically include at least one double-stranded DNA section that includes an amplifying restriction endonuclease cut site (e.g., an initial amplifying restriction endonuclease cut site, a secondary amplifying restriction endonuclease cut site, or a tertiary amplifying restriction endonuclease cut site). The other portions of the signal expansion nucleic acid or reporter nucleic acid can include DNA, RNA, or other molecules. For example, reporter nucleic acid can include biotin such that the reporter nucleic acid can be attached to a streptavidin-coated solid support. In some cases, one or both strands of the double-stranded section of the signal expansion nucleic acid or the reporter nucleic acid that contains an amplifying restriction endonuclease cut site can be RNA or a nucleic acid analog (e.g., a peptide nucleic acid (PNA)) provided that such a double-stranded section is capable of being cleaved by the amplifying restriction endonuclease. Examples of restriction endonucleases that can be used as amplifying restriction endonucleases to cleave a DNA:RNA hybrid section of signal expansion nucleic acid or reporter nucleic acid include, without limitation, HhaI, AluI, TaqI, HaeIII, EcoRI, HindII, SalI, and MspI restriction endonucleases.

Signal expansion nucleic acid or reporter nucleic acid described herein can be any length provided that the double-stranded section that contains the amplifying restriction endonuclease cut site is capable of being cleaved by the amplifying restriction endonuclease. In general, the double-stranded section of signal expansion nucleic acid or reporter nucleic acid can be between about 10 and about 500 or more nucleotides (e.g., between about 10 and about 400 nucleotides, between about 10 and about 300 nucleotides, between about 10 and about 200 nucleotides, between about 10 and about 100 nucleotides, between about 10 and about 50 nucleotides, between about 10 and about 25 nucleotides, between about 20 and about 500 nucleotides, between about 30 and about 500 nucleotides, between about 40 and about 500 nucleotides, between about 50 and about 500 nucleotides, between about 15 and about 50 nucleotides, between about 15 and about 25 nucleotides, between about 20 and about 50 nucleotides, or between about 18 and about 25 nucleotides, between about 20 and about 60 nucleotides, between about 25 and about 55 nucleotides, between about 30 and about 50 nucleotides, between about 35 and about 45 nucleotides, or between about 38 and about 42 nucleotides) in length. In some cases, the double-stranded section of signal expansion nucleic acid or reporter nucleic acid can be between 5 and 50 nucleotides in length. The amplifying restriction endonuclease cut site of the signal expansion nucleic acid or the reporter nucleic acid can be located at any position alone the double-stranded section. For example, the amplifying restriction endonuclease cut site can be towards the 5' end, towards the '3 end, or near the center of the double-stranded section of the signal expansion nucleic acid or the reporter nucleic acid. In general, the overall length of signal expansion nucleic acid or reporter nucleic acid described herein can be between about 10 and about 2500 or more nucleotides (e.g., between about 10 and about 2000 nucleotides, between about 10 and about 1000 nucleotides, between about 10 and about 500 nucleotides, between about 10 and about 400 nucleotides, between about 10 and about 300 nucleotides, between about 10 and about 200 nucleotides, between about 10 and about 100 nucleotides, between about 10 and about 50 nucleotides, between about 10 and about 25 nucleotides, between about 20 and about 500 nucleotides, between about 30 and about 500 nucleotides, between about 40 and about 500 nucleotides, between about 50 and about 500 nucleotides, between about 75 and about 500 nucleotides, between about 100 and about 500 nucleotides, between about 150 and about 500 nucleotides, between about 15 and about 50 nucleotides, between about 15 and about 25 nucleotides, between about 20 and about 50 nucleotides, between about 18 and about 25 nucleotides, between about 20 and about 60 nucleotides, between about 25 and about 55 nucleotides, between about 30 and about 50 nucleotides, between about 35 and about 45 nucleotides, or between about 38 and about 42 nucleotides) in length.

The amplifying restriction endonuclease cut site of signal expansion nucleic acid or reporter nucleic acid described herein can be a cut site of any type of restriction endonuclease. In addition, any type of restriction endonuclease can be used as an amplifying restriction endonuclease to cleave signal expansion nucleic acid or reporter nucleic acid. Examples of restriction endonucleases that can be used as amplifying restriction endonucleases include, without limitation, EcoRI, EcoRII, BamHI, HindIII, TaqI, NotI, HinfI, Sau3A, PovII, SmaI, HaeIII, HgaI, AluI, EcoRV, EcoP15I, KpnI, PstI, SacI, SalI, ScaI, SphI, StuI, XbaI, AarI, BanII, BseGI, BspPI, CfrI, EcoNI, Hsp92II, NlaIV, RsaI, TaiI, AasI, BbsI, BseJI, BspTI, ClaI, EcoO109I, I-PpoI, NmuCI, RsrII, TaqaI, AatII, BbuI, BseLI, BsrBI, CpoI, KasI, Acc65I, BbvCI, BseMI, BsrDI, Csp45I, Kpn2I, NruI, SacII, TasI, AccB7I, BbvI, BseMII, BsrFI, Csp6I, EheI, KpnI, NsbI, SalI, TatI, AccI, BceAI, BseNI, BsrGI, CspI, Esp3I, KspAI, NsiI, SapI, and TauI restriction endonucleases.

In general, signal expansion nucleic acid or reporter nucleic acid can be designed to have a double-stranded section that contains a single amplifying restriction endonuclease cut site. In some cases, signal expansion nucleic acid or reporter nucleic acid provided herein can be designed to have a double-stranded section that contains more than one (e.g., two, three, four, five, six, seven, eight, nine, ten, or more) amplifying restriction endonuclease cut site. When more than one amplifying restriction endonuclease cut site is used, the multiple amplifying restriction endonuclease cut sites can be cut sites for the same restriction endonuclease or cut sites for different restriction endonucleases. For example, reporter nucleic acid can be designed to have a double-stranded section that contains one initial amplifying restriction endonuclease cut site for an EcoRI initial amplifying restriction endonuclease and one secondary amplifying restriction endonuclease cut site for an XbaI secondary amplifying restriction endonuclease.

Any appropriate method can be used to obtain the nucleic acid component of signal expansion nucleic acid or reporter nucleic acid. For example, common molecular cloning and chemical nucleic acid synthesis techniques can be used to obtain the nucleic acid component of signal expansion nucleic acid or reporter nucleic acid. In some cases, the nucleic acid component of signal expansion nucleic acid or reporter nucleic acid can be synthesized using commercially available automated oligonucleotide synthesizers such as those available from Applied Biosystems (Foster City, Calif.). In some cases, signal expansion nucleic acid or reporter nucleic acid can be synthesized de novo using any of a number of procedures widely available in the art. Examples of such methods of synthesis include, without limitation, the β-cyanoethyl phosphoramidite method (Beaucage et al., *Tet. Let.*, 22:1859-1862 (1981)) and the nucleoside H-phosphonate method (Garegg et al., *Tet. Let.*, 27:4051-4054 (1986); Froehler et al., *Nucl. Acid Res.*, 14:5399-5407 (1986); Garegg et al., *Tet. Let.*, 27:4055-4058 (1986); and Gaffney et al., *Tet. Let.*, 29:2619-2622 (1988)). These methods can be performed by a variety of commercially-available automated oligonucleotide synthesizers. In some cases, recombinant nucleic acid techniques such as PCR and those that include using restriction enzyme digestion and ligation of existing nucleic acid sequences (e.g., genomic DNA or cDNA) can be used to obtain the nucleic acid component of signal expansion nucleic acid or reporter nucleic acid.

Signal expansion nucleic acid or reporter nucleic acid described herein can be attached to a solid support. Examples of solid supports include, without limitation, a well of a microtiter plate (e.g., a 96-well microtiter plate or ELISA plate), beads (e.g., magnetic, glass, plastic, or gold-coated beads), slides (e.g., glass or gold-coated slides), micro- or nano-particles (e.g., carbon nanotubes), platinum solid supports, palladium solid supports, and a surface of a chamber or channel within a microfluidic device. In some cases, a solid support can be a silicon oxide-based solid support, a plastic polymer-based solid support (e.g., a nylon, nitrocellulose, or polyvinylidene fluoride-based solid support) or a biopolymer-based (e.g., a cross-linked dextran or cellulose-based solid support) solid support.

Signal expansion nucleic acid or reporter nucleic acid can be directly or indirectly attached to a solid support. For example, biotin can be a component of signal expansion nucleic acid or reporter nucleic acid, and the signal expansion nucleic acid or the reporter nucleic acid containing biotin can be indirectly attached to a solid support that is coated with streptavidin via a biotin-streptavidin interaction. In some cases, signal expansion nucleic acid or reporter nucleic acid can be attached to a solid support via a covalent or non-covalent interaction. For example, signal expansion nucleic acid or reporter nucleic acid can be covalently attached to magnetic beads as described elsewhere (Albretsen et al., *Anal. Biochem.*, 189(1):40-50 (1990)).

Signal expansion nucleic acid can be designed to contain any type of restriction endonuclease as an amplifying restriction endonuclease (e.g., an initial amplifying restriction endonuclease, a secondary amplifying restriction endonuclease, or a tertiary amplifying restriction endonuclease). In general, an amplifying restriction endonuclease of signal expansion nucleic acid is typically a different restriction endonuclease than the restriction endonuclease that is used as a recognition restriction endonuclease. For example, when an EcoRI restriction endonuclease is used as a recognition restriction endonuclease, a restriction endonuclease other than an EcoRI restriction endonuclease (e.g., a HeaIII restriction endonuclease) is used as an amplifying restriction endonuclease. Examples of restriction endonucleases that can be used as amplifying restriction endonucleases include, without limitation, EcoRI, EcoRII, BamHI, HindIII, TaqI, NotI, HinfI, Sau3A, PovII, SmaI, HaeIII, HgaI, AluI, EcoRV, EcoP15I, KpnI, PstI, SacI, SalI, ScaI, SphI, StuI, XbaI, AarI, BanII, BseGI, BspPI, CfrI, EcoNI, Hsp92II, NlaIV, RsaI, TaiI, AasI, BbsI, BseJI, BspTI, ClaI, EcoO109I, I-PpoI, NmuCI, RsrII, TaqaI, AatII, BbuI, BseLI, BsrBI, CpoI, KasI, Acc65I, BbvCI, BseMI, BsrDI, Csp45I, Kpn2I, NruI, SacII, TasI, AccB7I, BbvI, BseMII, BsrFI, Csp6I, EheI, KpnI, NsbI, SalI, TatI, AccI, BceAI, BseNI, BsrGI, CspI, Esp3I, KspAI, NsiI, SapI, and TauI restriction endonucleases. Any number of molecules of the same amplifying restriction endonuclease can be attached to one signal expansion nucleic acid molecule. For example, a single signal expansion nucleic acid molecule can contain one, two, three, four, five, or more EcoRI amplifying restriction endonuclease molecules. In some cases, a single signal expansion nucleic acid molecule can contain two or more (e.g., two, three, four, five, or more) different types of amplifying restriction endonucleases. For example, a single signal expansion nucleic acid molecule can contain three BanII amplifying restriction endonuclease molecules and two SacII amplifying restriction endonuclease molecules.

Reporter nucleic acid can be designed to contain a label to aid in the detection of cleaved reporter nucleic acid. In some cases, signal expansion nucleic acid can be designed to contain a label. In such cases, signal expansion nucleic acid containing a label can be used in addition to reporter nucleic acid or in place of reporter nucleic acid to detect target nucleic acid. Examples of labels that can be a component of reporter nucleic acid or signal expansion nucleic acid include, without limitation, fluorescent labels (with or without the use of quenchers), dyes, antibodies, radioactive material, enzymes (e.g., horse radish peroxidase, alkaline phosphatase, laccase, galactosidase, or luciferase), redox labels (e.g., ferrocene redox labels), metallic particles (e.g., gold nanoparticles), and green fluorescent protein-based labels. In some cases, for a redox label, such as ferrocene, the detector can be an electrode for amperometric assay of redox molecules. For example, if the redox label is present in a reduced form of ferrocene, then the electrode at high electrode potential can provide an oxidation of the reduced form of ferrocene, thereby converting it to an oxidized form of ferrocene. The generated current can be proportional to the concentration of ferrocene label in the solution.

In one embodiment, reporter nucleic acid or signal expansion nucleic acid can contain a fluorescent label and a quencher such that cleaved reporter nucleic acid provides a fluorescent signal and uncleaved reporter nucleic acid does not provide a fluorescent signal. In some cases, the reporter nucleic acid or signal expansion nucleic acid can contain a label (e.g., a fluorescent label or an enzyme such as horse radish peroxidase) and can be attached to a solid support (e.g., a well of a microtiter plate). For example, the reporter nucleic acid or signal expansion nucleic acid can be attached to a solid support such that cleavage at the amplifying restriction endonuclease cut site by the amplifying restriction endonuclease releases a portion of the reporter nucleic acid or the signal expansion nucleic acid that contains the label. The resulting reaction mixture can be collected and assessed for the presence, absence, or amount of released portions of the reporter nucleic acid or signal expansion nucleic acid using the label. For example, the released portions of the reporter nucleic acid or the signal expansion nucleic acid, if present, can be transferred from one well of a microtiter plate (e.g., a 96-well plate) that contained the reporter nucleic acid or the signal expansion nucleic acid to another well of a microtiter plate, where the transferred material can be assessed for a signal from the label. Any number of molecules of a label can be attached to one reporter nucleic acid molecule or one signal expansion nucleic acid molecule. For example, a reporter nucleic acid molecule or a single signal expansion nucleic acid molecule can contain one, two, three, four, five, or more fluorescent molecules.

Any appropriate method can be used to attach a label to a nucleic acid component of reporter nucleic acid or signal expansion nucleic acid. In some cases, a label can be attached by an ionic or covalent attachment. For example, covalent bonds such as amide bonds, disulfide bonds, and thioether bonds, or bonds formed by crosslinking agents can be used. In some cases, a non-covalent linkage can be used. The attachment can be a direct attachment or an indirect attachment. For example, a linker can be used to attach a label to a nucleic acid component of reporter nucleic acid or signal expansion nucleic acid. In some cases, nucleic acid can include a thiol modification, and a label can be conjugated to the thiol-containing nucleic acid based on succinimidyl 4-[N-maleimidomethyl]cyclo-hexane-1-carboxylate (SMCC) using techniques similar to those described elsewhere (Dill et al., *Biosensors and Bioelectronics,* 20:736-742 (2004)). In some cases, a biotinylated nucleic acid and a streptavidin-containing label can be attached to one another via a biotin-streptavidin interaction. A label can be conjugated with streptavidin using, for example, sulfosuccinimidyl 6-(3'-[2-pyridyldithio]-propionamido)hexanoate. A label can be attached at any location of a nucleic acid component of reporter nucleic acid or signal expansion nucleic acid. For example, a label can be attached at an end (e.g., a 5' end or 3' end) of a nucleic acid component, in the middle of a nucleic acid component, or at any position along the length of a nucleic acid component of reporter nucleic acid or signal expansion nucleic acid.

As described herein, the methods and materials provided herein can be used to detect target nucleic acid of a target microorganism or virus in any type of sample. For example, food product samples, samples obtained from a material that has been in contact with a food product to be tested (e.g., wash or rinse samples), and environmental samples (e.g., water samples, soil samples, and air samples) can be collected and assessed for target nucleic acid. Once obtained, a sample to be assessed can be processed to obtain nucleic acid. For example, a nucleic acid extraction can be performed on a beef product sample to obtain a sample that is enriched for nucleic acid. In some cases, a sample can be heated or treated with a cell lysis agent to release nucleic acid from cells present in the sample.

As described herein, a sample (e.g., a food product sample) can be assessed for the presence, absence, or amount of target microbial or viral nucleic acid (e.g., target pathogen nucleic acid) using an enzymatic amplification cascade of restriction endonucleases described herein without using a nucleic acid amplification technique (e.g., a PCR-based nucleic acid technique). Assessing samples (e.g., food product samples) for the presence, absence, or amount of target nucleic acid using an enzymatic amplification cascade of restriction endonucleases described herein without using a nucleic acid amplification technique can allow food manufacturers, producers, processors, and suppliers as well as food testing entities and government agencies to test food products without the need for potentially expensive thermal cycling devices and potentially time consuming thermal cycling techniques. In some cases, the methods and materials provided herein can be used in combination with a PCR-based nucleic acid technique. For example, a PCR-based nucleic acid technique can be performed to amplify nucleic acid (e.g., a target pathogen's nucleic acid) present within a food product sample, and the resulting amplification material can be assessed using an enzymatic amplification cascade of restriction endonucleases described herein to detect the presence, absence, or amount of a particular nucleic acid (e.g., a target pathogen's nucleic acid). In some cases, a limited PCR-based nucleic acid technique can be performed to amplify a target nucleic acid to a point where the amount of amplified target nucleic acid is increased only slightly over the amount of target nucleic acid originally present within the food product sample. For example, a two to twelve cycle PCR technique (e.g., a 2, 3, 4, 5, 6, 7, 8, 9, 10, 11, or 12 cycle PCR technique) can be performed to slightly increase the amount of amplified target nucleic acid as compared to the amount of unamplified target nucleic acid originally present within the food product sample. Such limited PCR-based nucleic acid techniques, when used in combination with an enzymatic amplification cascade of restriction endonucleases described herein, can allow food manufacturers, producers, processors, and suppliers as well as food testing entities and government agencies to test food products with a potentially increased level of sensitivity and/or specificity without the potentially lengthy time involved in thermal cycling techniques that include a greater number of cycles. This increased level of sensitivity and/or specificity can be over the high level of sensitivity and specificity of a comparable testing procedure that includes an enzymatic amplification cascade of restriction endonucleases described herein without the limited PCR-based nucleic acid technique. In some cases, the PCR-based nucleic acid technique can be performed to amplify a target nucleic acid to a point where the amount of amplified target nucleic acid is easily detectable (e.g., visually detectable using gel electrophoresis and ethidium bromide staining). For example, a 15 or more cycle PCR technique (e.g., a 20 cycle PCR technique) can be performed to produce at least ng amounts (e.g., greater than 1 ng, 10 ng, 100 ng, 1 µg, 10 µg, or more) of amplified nucleic acid. Such PCR-based nucleic acid techniques, when used in combination with an enzymatic amplification cascade of restriction endonucleases described herein, can allow food manufacturers, producers, processors, and suppliers as well as food testing entities and government agencies to test food products with a potentially increased in the level of sensitivity and/or specificity. This increased level of sensitivity and/or specificity can be over the high level of sensitivity and specificity of a comparable testing procedure that includes an enzymatic amplification cascade of restriction endonucleases described herein without the PCR-based nucleic acid technique.

In some cases, a sample (e.g. a food product sample) can be obtained and subjected to a culturing technique. For example, a food product sample can be collected and cultured with medium (e.g., enrichment medium or broth with or without the ability to promote selective growth) to enrich the sample such that the number of microorganisms or viruses contaminating the sample can increase. Examples of enrichment medium or broth include, without limitation, tryptic soy broth, the universal pre-enrichment broth, the University of Vermont modification medium, and Fraser broth. In some cases, the culture medium can contain a nutrient, ingredient, or drug that prevents certain microbial species or strains from replicating while allowing other microbial species or strains to replicate. In some cases, the culturing technique can include incubating a sample at an appropriate temperature (e.g. between 15° C. and 45° C., between 20° C. and 45° C., between 25° C. and 45° C., between 30° C. and 45° C., between 30° C. and 40° C., between 35° C. and 45° C., or between 35° C. and 40° C.) for an appropriate period of time (e.g., between about 0.5 hours and 48 hours, between about 0.5 hours and 36 hours, between about 0.5 hours and 24 hours, between about 0.5 hours and 12 hours, between about 0.5 hours and 8 hours, between about 0.5 hours and 6 hours, between about 0.5 hours and 5 hours, between about 0.5 hours and 4 hours, between about 0.5 hours and 3 hours, between about 0.5 hours and 2 hours, between about 1 hour and 4 hours, or between about 2 hours and 4 hours). For example, a sample can be obtained and cultured in enrichment medium at 37° C. for 2 to 6 hours. Examples of culture techniques that can be used as described herein include, without limitation, those described elsewhere (Nam et al., *Foodborne Pathog. Dis.,* 1(1):37-44 (2004)) and Guerini et al., *J. Food Prot.,* 70(1):53-7 (2007)).

In some cases, a sample, obtained and subjected to a culturing technique or not, can be processed, for example, to remove non-nucleic acid material, to disrupt cell membranes to release nucleic acid, and/or to collect or extract nucleic acid, such that nucleic acid of the sample, if present within the sample, is available for hybridization to probe nucleic acid. For example, a food product sample can be treated with a lysis buffer and subjected to nucleic acid extraction such that a major component of the sample is nucleic acid. In some cases, a sample can be homogenized and treated to disrupt cells including microbial cells that are present in the sample. For example, a sample can be subjected to high speed mechanical homogenization with glass/silica/zirconium/stainless steel beads, can be subjected to high temperature (e.g., boiling or autoclaving), can be subjected to chemical lysis with detergents and/or surfactants (e.g., sodium dodecyl sulfate, cetyltrimethylammonium bromide, or sodium lauroyl sarcosin), can be subjected to one or more freeze-thaw cycles using, e.g., liquid nitrogen or dry ice, can be subjected to sonication, or can be subjected to combinations thereof. The resulting sample can be subjected to a standard nucleic acid extraction technique such as those described elsewhere (e.g., Sambrook and Russell, (2001) Molecular Cloning: A Laboratory Manual, Third Edition, Cold Spring Harbor Press) or a nucleic acid extraction technique that includes the use of magnetic beads or selective DNA-binding membranes (see, e.g., QIAGEN DNeasy® Blood & Tissue Kit, or Mo Bio PowerFood™ Microbial DNA Isolation Kit). For example, the sample can be contacted with magnetic beads that bind nucleic acid, the beads can be removed, and bound nucleic acid can be eluted into an appropriate buffer to form a processed sample for further analysis using the methods and materials provide herein. Such a process can be carried out using a variety of kits including, without limitation, Qiagen BioSprint 96 One-For-All Vet Kit (a rapid and economical automated purification of viral nucleic acid and/or bacterial nucleic acid from samples based on magnetic beads) and Chemicell geneMAG-PCR cleanup kit.

In some cases, a sample can be processed in a manner designed to fragment any nucleic acid present within the sample. For example, genomic or large pieces of nucleic acid present within a sample can be subjected to a sonication technique and/or restriction digestion with a restriction endonuclease such as DpnII or CviJI to generate nucleic acid fragments. Such fragmentation can be performed using restriction endonucleases that are different from those used as recognition or amplifying restriction endonucleases to assess the sample as described herein.

In some cases, the sample can be treated such that any double-stranded nucleic acid present within the sample is separated. For example, a sample can be heated and then snap-cooled or can be subjected to chemical (e.g., sodium hydroxide) denaturation. In some cases, when the sample is subjected to a PCR-based technique, certain primer or reaction modifications can be used to generate preferentially single-stranded product. For example, unidirectional DNA polymerase reaction can be performed with a single specific primer. In some cases, the strands of nucleic acid can be separated, and the strand of interest can be enrichment using specific biotinylated primers and streptavidin-conjugated magnetic beads. In some cases, selective digestion of one of the strands can be accomplished using lambda exonucleases.

As described herein, a sample can be subjected to a nucleic acid amplification technique. For example, a food product sample containing extracted nucleic acid can be subjected to a quick PCR-based amplification of one or more specific targets (e.g., 1 hour, end-point PCR) or to a whole genome amplification technique (e.g., Qiagen REPLI-g Screening Kit for high-throughput manual or automated whole genome amplification).

Once obtained, a sample to be assessed, whether subjected to a PCR-based nucleic acid technique or not, can be contacted with a probe nucleic acid as described herein. This contacting step can be carried out for any period of time and at any temperature that allows target nucleic acid to hybridize with probe nucleic acid. For example, this step can be performed between 10 seconds and 24 hours (e.g., between 30 seconds and 12 hours, between 30 seconds and 8 hours, between 30 seconds and 4 hours, between 30 seconds and 2 hours, between 30 seconds and 1 hour, between 1 minute and 24 hours, between 1 minute and 12 hours, between 1 minute and 8 hours, between 1 minute and 4 hours, between 1 minute and 2 hours, between 1 minute and 1 hour, between 5 minutes and 1 hour, between 10 minutes and 1 hour, between 15 minutes and 1 hour, or between 30 minutes and 1 hour). The initial temperature can be between 15° C. and 100° C. (e.g., between 23° C. and 98° C., between 23° C. and 90° C., between 23° C. and 85° C., between 23° C. and 75° C., between 23° C. and 65° C., between 23° C. and 55° C., between 23° C. and 45° C., between 23° C. and 35° C., between 30° C. and 95° C., between 30° C. and 85° C., between 30° C. and 75° C., between 30° C. and 65° C., between 30° C. and 55° C., between 30° C. and 45° C., between 20° C. and 40° C., between 20° C. and 30° C., and between 25° C. and 35° C.). The temperature during this contacting step can remain constant or can be increased or decreased. For example, the initial temperature can be between about 40° C. and about 85° C., and then the temperature can be allowed to decrease to room temperature over a period of about 30 seconds to about 30 minutes (e.g., between about 30 seconds and about 15 minutes, between about 30 seconds and about 10 minutes, between about 1 minute and about 30 minutes, between about 1 minute and about 15 minutes, or between about 1 minute and about 5 minutes).

Contact of the sample (e.g., a food product sample to be tested) with probe nucleic acid can occur in the presence of the recognition restriction endonucleases, or a separate step of adding the recognition restriction endonucleases to the reaction can be performed. The recognition restriction endonuclease step can be carried out for any period of time and at any temperature that allows the recognition restriction endonuclease to cleave recognition restriction endonuclease cut sites formed by the hybridization of target nucleic acid to the probe nucleic acid. For example, this step can be performed between one second and 24 hours (e.g., between one second and 30 minutes, between one second and one hour, between five seconds and one hour, between 30 seconds and 24 hours, between 30 seconds and 12 hours, between 30 seconds and 8 hours, between 30 seconds and 4 hours, between 30 seconds and 2 hours, between 30 seconds and 1 hour, between 1 minute and 24 hours, between 1 minute and 12 hours, between 1 minute and 8 hours, between 1 minute and 4 hours, between 1 minute and 2 hours, between 1 minute and 1 hour, between 5 minutes and 1 hour, between 10 minutes and 1 hour, between 15 minutes and 1 hour, or between 30 minutes and 1 hour). The temperature can be between 15° C. and 75° C. (e.g., between 15° C. and 75° C., between 15° C. and 65° C., between 15° C. and 55° C., between 15° C. and 45° C., between 15° C. and 35° C., between 15° C. and 30° C., between 23° C. and 55° C., between 23° C. and 45° C., between 30° C. and 65° C., between 30° C. and 55° C., between 30° C. and 45° C., between 30° C. and 40° C., between 35° C. and 40° C., and between 36° C. and 38° C.). Any appropriate concentration of recognition restriction endonuclease can be used. For example, between about 0.001 units and 1000 units (e.g., between about 0.001 units and 750 units, between about 0.001 units and 500 units, between about 0.001 units and 250 units, between about 0.001 units and 200 units, between about 0.001 units and 150 units, between about 0.001 units and 100 units, between about 0.001 units and 50 units, between about 0.001 units and 25 units, between about 0.001 units and 10 units, between about 0.001 units and 1 unit, between about 0.001 units and 0.1 units, between about 0.01 units and 1000 units, between about 0.1 units and 1000 units, between about 1 unit and 1000 units, between about 10 units and 1000 units, between about 50 units and 1000 units, between about 0.5 units and 100 units, or between about 1 unit and 100 units) of restriction endonuclease can be used. Other restriction endonuclease reaction conditions such as salt conditions can be used according to manufacture's instructions.

When one step of a method provided herein is completed, the resulting reaction product containing cleaved nucleic acid can be used in the next step. For example, cleaved nucleic acid of a reaction product can be removed from uncleaved nucleic acid and used in the next step of the method. For example, when probe nucleic acid is attached to a solid support, the released portions of probe nucleic acid that contain an amplifying restriction endonuclease can be collected and placed in contact with reporter nucleic acid or signal expansion nucleic acid as described herein. The resulting reaction products of a particular step can be manually or automatically (e.g., robotically) transferred to a location containing nucleic acid for the next step (e.g., reporter nucleic acid or signal expansion nucleic acid), which nucleic acid can be attached or not attached to a solid support. In some cases, one reaction of a method described herein can be carried out at one location (e.g., a chamber) of a microfluidic device or blister package device, and the reaction products that are generated can be moved to another location (e.g., another chamber) that contains nucleic acid for the next step (e.g., reporter nucleic acid or signal expansion nucleic acid) via a channel. In some cases, cleaved nucleic acid of a reaction product can be used in the next step of the method by removing the uncleaved nucleic acid from the reaction product. For example, when magnetic beads are used as a solid support, a magnetic force can be used to remove the magnetic beads and any attached uncleaved nucleic acid from the reaction product. In some cases, two or more reactions of a method provided herein can be carried out at one location (e.g., a single well of a microtiter plate or a single chamber of a microfluidic device). For example, a single compartment can have one region that contains immobilized probe nucleic acid and another region that contains immobilized reporter nucleic acid provided that the amplifying restriction endonuclease of the immobilized probe nucleic acid is not capable of cleaving the amplifying restriction endonuclease cut site of the reporter nucleic acid unless target nucleic acid hybridizes to the probe nucleic acid and the recognition restriction endonuclease cleaves the probe nucleic acid, thereby releasing a portion of the probe nucleic acid that contains the amplifying restriction endonuclease so that it is capable of cleaving the reporter nucleic acid. In another example, a single compartment can have one region that contains immobilized probe nucleic acid, other regions that contain immobilized signal expansion nucleic acid (e.g., one region that contains a first signal expansion nucleic acid and another region that contains a second signal expansion nucleic acid), and another region that contains immobilized reporter nucleic acid provided that the amplifying restriction endonucleases of immobilized probe nucleic acid and signal expansion nucleic acid are not capable of cleaving their intended amplifying restriction endonuclease cut sites until they are released as described herein. Such single compartments can be made using partitions or sub-compartments within the single compartment. For example, a sample to be tested can be placed into a single well of a microtiter plate that contains probe nucleic acid, recognition restriction endonucleases, first and second signal expansion nucleic acid, and reporter nucleic acid such that cleaved reporter nucleic acid and/or signal expansion nucleic acid is produced as described herein when target nucleic acid is present in the sample being tested and little or no cleaved reporter nucleic acid and/or signal expansion nucleic acid is produced when target nucleic acid is not present in the sample being tested.

Any appropriate method can be used to detect cleaved reporter nucleic acid and/or signal expansion nucleic acid to determine the presence, absence, or amount of target nucleic acid in a sample, which can indicate the presence, absence, or amount of a target microorganism or virus. For example, size separation techniques can be used to assess reaction products for cleaved reporter nucleic acid and/or signal expansion nucleic acid. Examples of such size separation techniques include, without limitation, gel electrophoresis and capillary electrophoresis techniques. In some cases, a melt curve analysis can be performed to assess reaction products for cleaved reporter nucleic acid and/or signal expansion nucleic acid. As described herein, a label can be used to aid in the detection of cleaved nucleic acid (e.g., reporter nucleic acid and/or signal expansion nucleic acid). Examples of labels that can be used include, without limitation, fluorescent labels (with or without the use of quenchers), dyes, antibodies, radioactive material, enzymes (e.g., horse radish peroxidase, alkaline phosphatase, laccase, galactosidase, or luciferase), redox labels (e.g., ferrocene redox labels), metallic particles (e.g., gold nanoparticles), and green fluorescent protein based labels. For example, the release of fluorescently labeled portions of reporter nucleic acid and/or signal expansion nucleic acid from a solid support can be assessed using common fluorescent label detectors. In some cases, cleaved reporter nucleic acid and/or signal expansion nucleic acid can be detected electrochemically. For electrochemical detection, the reporter nucleic acid and/or signal expansion nucleic acid can include a ferrocene redox label. Reporter nucleic acid and/or signal expansion nucleic acid containing ferrocene can be obtained by coupling ferrocene carboxylic acid with an amino-modified oligonucleotide using the carbodiimide reaction in the presence of an excess of ferrocene carboxylic acid. In one embodiment, for a redox label, such as ferrocene, the detector can be an electrode for amperometric assay of redox molecules. For example, if the redox label is present in a reduced form of ferrocene, then the electrode at high electrode potential can provide an oxidation of the reduced form of ferrocene, thereby converting it to an oxidized form of ferrocene. The generated current can be proportional to the concentration of ferrocene label in the solution.

The methods and materials provided herein can be used to assess one or more samples for target nucleic acid in real-time. For example, a fluorescent label/quencher system or an electrochemical redox label system can be used to detect cleavage of reporter nucleic acid and/or signal expansion nucleic acid in real time.

The methods and materials provided herein can be used to assess one or more samples (e.g., two, three, four, five, six, seven, eight, nine, ten, 20, 50, 100, 500, 1000, or more) for a single type of target nucleic acid. For example, 1000s of food product samples (e.g., beef samples) can be assessed for a target nucleic acid present in O157:H7 E. coli. In some case, the methods and materials provided herein can be used in a multiplex manner to assess one or more samples for more than one (e.g., two, three, four, five, six, seven, eight, nine, ten, 20, 50, 100, 500, 1000, or more) type of target nucleic acid. For example, target nucleic acid for ten different sequences (e.g., ten different sequences from a single bacterial species or strain, or a different sequence from ten different bacterial species or strains) can be used to design ten different probe nucleic acid molecules. In such cases, a different label can be used to correspond to each probe nucleic acid such that the detected signals can indicate which of the ten target nucleic acids are being detected. In some cases, the methods and materials provided herein can be used in a multiplex manner to assess 1000s of food product samples for contamination by a particular bacterial species that can exist in nature as a heterogeneous species. For example, the methods and materials provided herein can be used in a multiplex manner to assess 1000s of beef samples for contamination by any one of a group of different *E. coli* strains that exist in nature. In such cases, many different target nucleic acids can be designed and included in a particular testing protocol or device such that the presence of any one of the group of different *E. coli* strains are detected.

This document also provides kits for performing the methods described herein. For example, a kit provided herein can include probe nucleic acid with or without being attached to a solid support and/or reporter nucleic acid with or without being attached to a solid support. In some cases, such a kit can include a recognition restriction endonuclease, first signal expansion nucleic acid, second signal expansion nucleic acid, or a combination thereof. In some cases, a kit can be configured into a microfluidic device that allows for the movement of probe nucleic acid, first signal expansion nucleic acid, second signal expansion nucleic acid, reporter nucleic acid, or recognition restriction endonucleases (or any combination thereof) as well as a cleaved portion of any such nucleic acid in a manner that allows a detection method provided herein to be carried out with or without the nucleic acid being attached to a solid support. For example, a kit provided herein can be a microfluidic device capable of receiving a sample and contacting that sample with probe nucleic acid. The probe nucleic acid can be designed to include a length of nucleotides followed by the sequence complementary to the target nucleic acid, which can create a recognition restriction endonuclease cut site, followed by an amplifying restriction endonuclease. The distance from the recognition restriction endonuclease cut site to the amplifying restriction endonuclease can be relatively short (e.g., 100, 50, 25, 10, or less nucleotides), while the distance from the recognition restriction endonuclease cut site to the beginning of the length of nucleotides can be relatively long (e.g., 50, 100, 150, 200, 500, 1000, 2000, or more). In such cases, cleavage of the probe nucleic acid at the recognition restriction endonuclease cut site can result in a relatively small portion that contains the amplifying restriction endonuclease and is capable of travelling faster than the larger uncleaved probe nucleic acid. This difference can allow the cleaved portion containing the amplifying restriction endonuclease to reach an area of the microfluidic device containing signal expansion nucleic acid or reporter nucleic acid so that the next reaction can be carried out without the presence of uncleaved probe nucleic acid. In some cases, after the smaller portion containing the amplifying restriction endonuclease enters the area containing signal expansion nucleic acid or reporter nucleic acid, a valve can be used to prevent the larger uncleaved probe nucleic acid from entering. In some cases, a filter can be used to limit the ability of larger uncleaved probe nucleic acid from proceeding to the next reaction location. Similar approaches can be used during other steps of a method provided herein to separate cleaved nucleic acid from uncleaved nucleic acid.

In some cases, a kit provided herein can be a portable or self-contained device, packet, vessel, or container that can be used, for example, in field applications. For example, such a kit can be configured to allow a user to insert a sample for analysis. Once inserted, the sample can be heated (e.g., heated to about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 75, 80, 85, 90, 95, or more ° C.) and/or cooled by a heating or cooling mechanism located within the kit. For example, an exothermic or endothermic chemical reaction can be initiated within the kit to increase, decrease, or maintain the temperature. Such exothermic or endothermic chemical reactions can be carried out within the kit without being in fluid communication with the reactions of the target nucleic acid detection method. An iron oxidation reaction is an example of an exothermic chemical reaction that can be used to heat a kit provided herein. An endothermic chemical reaction that can be used to cool a kit provided herein can be a reaction that includes the use of ammonium chloride and water, potassium chloride and water, or sodium carbonate and ethanoic acid. In general, when detecting DNA target nucleic acid, the kit can be designed to generate, if needed, enough heat to denature double stranded DNA present within the sample. The kit also can be designed to generate appropriate heating and cooling temperatures to carry out each step of a detection method provided herein. In some cases, a kit provided herein can include a temperature indicator (e.g., color indicator or thermometer) to allows a user to assess temperature.

In some cases, a kit can be designed to provide a user with a "yes" or "no" indication about the presence of target nucleic acid within a tested sample. For example, a label having the ability to generate a change in pH can be used, and a visual indicator (e.g., a pH-based color indicator) can be used to inform the user of the presence of target nucleic acid based on a change in pH.

In some cases, high throughput systems can be designed to provide a user with an indication about the presence, absence, or amount of target nucleic acid in tested samples. In some cases, a system can include a reel-to-reel type sample substrate carrier, which can operate in a manner analogous to a paper making machine, for example. The substrate in a reel-to-reel system can include, e.g., a roll of transparent film or tape, which can be flat or can have embedded wells, and which can have a series of individual reaction sections for binding of probe nucleic acid and application of test samples. A film substrate can be made from a material such as, for example, clear nylon, polyethylene, polyurethane, polypropylene, acetal, acrylic, nylon (polyamides), polystyrene, acrylonitrile, butadiene styrene (ABS), polycarbonate, or combinations thereof. Such a substrate can have a width of about 0.5 cm to about 2 cm (e.g., 0.5 cm, 0.75 cm, 1 cm, 1.25 cm, 1.5 cm, 1.75 cm, or 2 cm), and a length of about 100 cm to about 1000 m (e.g., 100 cm, 250 cm, 500 cm, 1 m, 10 m, 25 m, 50 m, 75 m, 100 m, 250 m, 500 m, 750 m, or 1000 m). Reaction sections or wells can be positioned along the substrate such that about each 0.75 to 1.25 linear cm (e.g., 0.75, 0.8, 0.9, 1, 1.1, 1.2, or 1.25 linear cm) contains one reaction section or well.

The substrate can have a first end and a second end. The first end can be attached (reversibly or irreversibly) to a first reel, the second end can be attached (reversibly or irreversibly) to a second reel, and the body of the substrate can be wrapped around the first reel, the second reel, or a combination thereof. During use of a reel-to-reel type system, the reels can rotate such that the substrate is transferred from the first reel to the second reel. The individual reaction wells or sections can pass through various assay stages as the substrate is passed between the reels. For example, the reaction sections or wells can pass through a stage at which streptavidin and other reagents are attached to the substrate, e.g., by washable ball-point probes or ink jet style syringes with disposable needles. In some cases, a probe nucleic acid containing a single stranded nucleic acid sequence linked to an amplification restriction endonuclease can be prepared and subsequently attached to the substrate. Similarly, a reporter nucleic acid linked to a marker can be prepared and subsequently attached to the substrate. Alternatively, a probe nucleic acid and/or a reporter nucleic acid can be attached to the substrate in stages, such that the nucleic acid portion(s) of the probe and the amplification restriction endonuclease, or the nucleic acid portion(s) of the reporter and the marker, are separately added to and assembled on the substrate.

During subsequent stages of using a reel-to-reel system, test samples of nucleic acid (e.g., single stranded DNA or RNA) can be added to the reaction sections or wells, recognition restriction endonuclease can be added, and the substrate can run through a light chamber to detect fluorescent markers, for example. During use of such a system, individual reaction samples may or may not be transferred from one area of the substrate to another. For example, in some cases, the binding of test sample nucleic acid to probe nucleic acid, cleavage by recognition restriction endonuclease, and cleavage of reporter nucleic acid by amplification restriction endonuclease can take place in a single well or reaction section. In some cases, all or a portion of a reaction mixture can be transferred from one position or well to another (e.g., such that a reaction sample containing amplification restriction endonuclease released from the probe nucleic acid can be transferred to an area of the substrate containing reporter nucleic acid).

In some cases, the substrate can run through an aseptic channel to prevent or reduce assay contamination, and/or a second film or substrate layer can be included to cover, protect, or seal the sample wells or sections for process needs and/or storage, for example. In some cases, the system can include a bar-code scanning system to attach a date and/or time stamp at the location of each sample spot or well on the substrate. Activity (e.g., fluorescence) information can be date stamped on the substrate, and corresponding digitized photographs can be stored in memory for later recall. In some cases, a finished roll of substrate can be stored, e.g., in cold storage, for later reference if needed.

Figure 7:
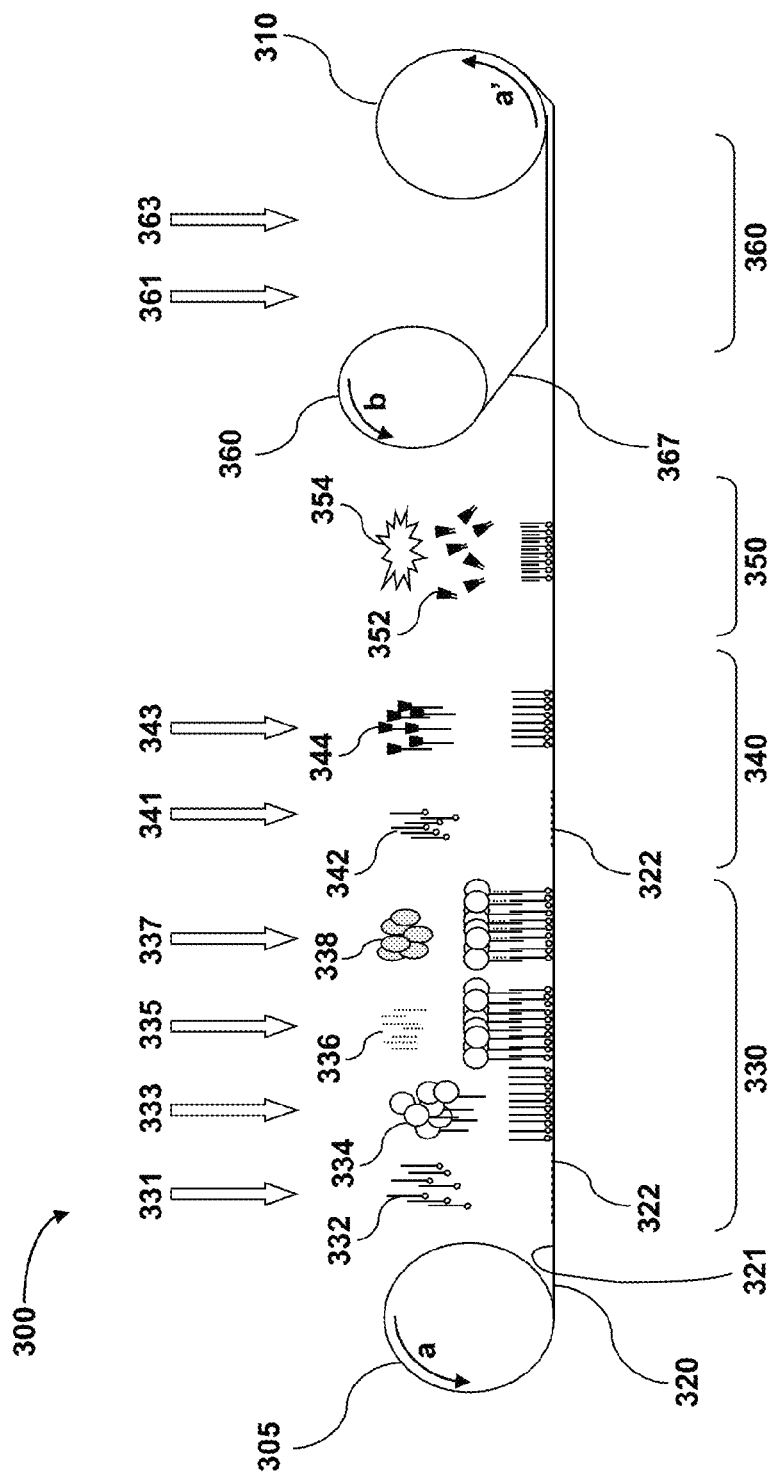
FIG. 7 is a schematic of an exemplary configuration for a reel-to-reel high throughput system, showing a side view of the film to which system components (e.g., probe and reporter nucleic acids) are attached, and indicating stages for addition of probe nucleic acid components, target nucleic acid, recognition restriction endonuclease, and reporter nucleic acid components.
Figure 8C:
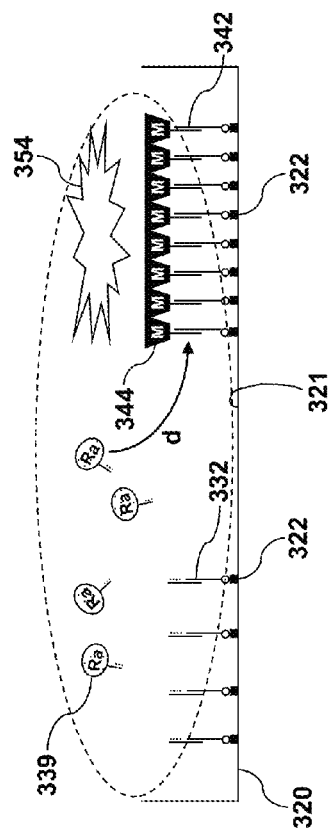
Figure 8D:
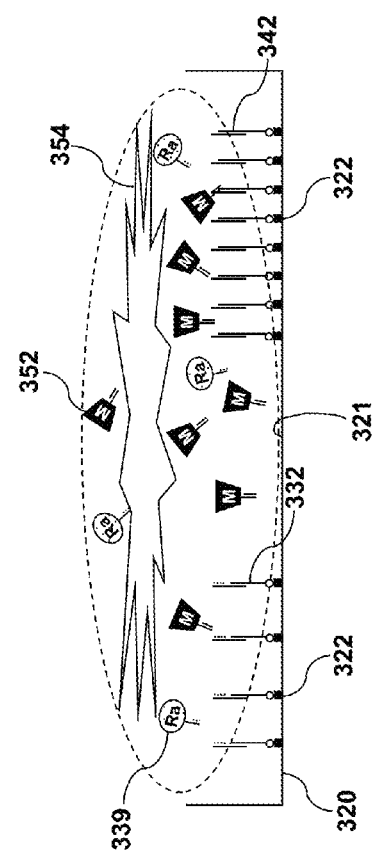

An example of a reel-to-reel system is depicted in FIGS. 7 and 8. FIG. 7 depicts a system from a side view, while the panels in FIGS. 8A-8D depict a cross-sectional end-on view of a single reaction section. System 300 can include first reel 305, second reel 310, and film 320 having reaction surface 321. Portions of film 320 (e.g., reaction sections or wells) can be coated with streptavidin 322. The use of system 300 can include a series of stages, indicated by brackets 330, 340, 350, and 360 in FIG. 7. Each stage can include steps during which components of the enzymatic amplification cascade reactions are added to the reaction sections, and steps of the cascade can occur. The various stages and steps of system can occur as film 320 is transferred from first reel 305 to second reel 310, which can rotate in the direction indicated by arrows a and a'. As nucleic acid and endonuclease components are added, reactions can be mixed by, for example, vibrating film 320. In some cases, the test nucleic acid can be linked to magnetic beads, and reactions can be mixed using a magnetic mixer.

With further reference to FIG. 7, recognition stage 330 can include steps indicated by arrows 331, 333, 335, and 337. In step 331, a biotin-linked single strand 332 can be added. In step 333, amplification restriction endonuclease 334 can be added. Amplification restriction endonuclease 334 can be linked a single stranded nucleic acid having a sequence that is complementary to a portion of biotin-linked single strand 332, such that amplification restriction endonuclease 334 becomes attached to film 320 via biotin-linked single strand 332. The biotin-linked single strand 332, amplification restriction endonuclease 334, and single stranded nucleic acid linked to amplification restriction endonuclease 334 can for probe nucleic acid.

In step 335, test nucleic acid 336 can be added, and in step 337, recognition restriction endonuclease 338 can be added. Recognition restriction endonuclease 338 can then cleave probe nucleic acid to which test nucleic acid has bound to generate a double-stranded recognition sequence for recognition restriction endonuclease 338. After such cleavage, amplification restriction endonuclease 334 is released from film 320 (not depicted in FIG. 7).

Amplification stage 340 can include the steps indicated by arrows 341 and 343. In step 341, biotin-linked single stranded nucleic acid 342 can be added. In step 343, marker 344 can be added. Marker 344 can be linked a single stranded nucleic acid having a sequence that is complementary to a portion of biotin-linked single stranded nucleic acid 342, such that marker 344 becomes attached to film 320 via biotin-linked single stranded nucleic acid 342 when the complementary portions anneal. The annealed portions contain a recognition sequence for amplification restriction endonuclease 334. Biotin-linked single stranded nucleic acid 342, marker 344, and single stranded nucleic acid having a sequence that is complementary to a portion of biotin-linked single stranded nucleic acid 342 can form reporter nucleic acid.

After amplification restriction endonuclease 334 is released from film 320 during recognition stage 330, amplification restriction endonuclease 334 can cleave reporter nucleic acid at its double stranded recognition sequence, releasing marker 344 from film 320. The released marker is depicted as free marker 352 in FIG. 7.

During detection stage 350, film 320 can pass through a reader that can detect signal 354 generated by free marker 352. In some cases, detection stage 350 also can include passage through a photo scanner, which can generate digital images for storage.

Sealing and storage stage 360 can include step 361, during which identifying information (e.g., date, time, lot identification, technician identification, and other vital information) can be stamped onto film 320. Sealing and storage stage 360 also can include sealing step 363, during which blank sealing film 367 is transferred from third reel 365 (e.g., by rotation of reel 365 in the direction of arrow b) and layered over reaction surface 321 of film 320. The sealed film can be stored on second reel 310.

FIGS. 8A-8D depict several steps of system 300 as seen in an end-on cross-sectional view through a single reaction section of film 320. As depicted in FIGS. 8A-8D, probe nucleic acids and reporter nucleic acids are positioned on adjacent but non-overlapping areas within the same reaction section. Probe nucleic acids and recognition stage steps are shown on the left side of the depicted reaction section, while reporter nucleic acids and amplification stage steps are shown on the right side. Dashed ovals indicate relative liquid sample volumes.

As shown in FIGS. 8A and 8B, components of the recognition and amplification stages are kept separate from each other due to relatively small sample volumes. FIG. 8A depicts addition of test nucleic acid 336 in step 335, which increases the sample volume. FIG. 8B depicts addition of recognition restriction endonuclease 338 in step 337, which further increases the sample volume. As indicated by arrow c, recognition restriction endonuclease 338 then can cleave probe nucleic acid to which test nucleic acid has bound to generate its double stranded recognition sequence.

After cleavage of probe nucleic acid 332 by recognition restriction endonuclease 338, free amplification restriction endonuclease 339 is released from film 320, as depicted in FIG. 8C. As indicated by the dashed oval, the sample volume now large enough that free amplification restriction endonuclease 339 has access to and can cleave double stranded reporter nucleic acid (indicated by arrow d). Such cleavage results in release of free marker 352, which can diffuse throughout the reaction mixture.

It is noted that in the example depicted in FIGS. 8A-8D, signal 354 from marker 344 is present throughout the reaction process. Prior to cleavage of reporter nucleic acid by free amplification restriction endonuclease 339, however, signal 354 is limited to the right side of the reaction section. After cleavage, free marker 352 can diffuse throughout the reaction section. The differential distribution of signal 354 can indicate whether the target nucleic acid sequence is present.

In some cases, a platen style system with a regenerative substrate can be used in a high-throughput system. For example, a system can include a platen with a matrix of nickel with platinum coated or plastic ballpoint needles. The platens can be readily removable, or can be automatically dipped in washing solutions. In some cases, a quick dip method can be used to attach streptavidin and/or the probe nucleic acids. After use, the platen can be cleaned and reused.

In some cases, the methods and materials provided herein can be used to assess water for possible microbial contamination. For example, water to be tested can be filtered using a membrane filet cartridge such as a Millipore Sterivex with 0.2 µm pores. Microbes, if present, will stay on the filter. After filtering about 0.25 L to about 500 L or more of water (e.g., 0.5 to 5 L of water), the filter can processed to obtain a sample from the filter that would contain any captured microorganisms. In some cases, the sample can be cultured and then processed to contain extracted nucleic acid (e.g., DNA) or can be processed to contain extracted nucleic acid (e.g., DNA) without culturing the sample. Once processed, the sample can be assessed as described herein to determine the presence, absence, or amount of microbial contamination.

In some cases, the methods and materials provided herein can be used to determine whether detected target nucleic acid of a microorganism is the result of live or dead microorganisms present within the sample. For example, a sample can be obtained and divided into at least two portions. One portion can be assessed for target nucleic acid without performing a culturing technique, while another portion of the sample can be assessed for target nucleic acid after performing a culturing technique (e.g., an enrichment culture performed at 37° C. for 2 to 6 hours). The results from each portion can be compared to determine if the sample portion subjected to culturing contained more target nucleic acid than the sample portion not subjected to culturing. If the sample portion subjected to culturing contains more target nucleic acid than the sample portion not subjected to culturing, then the sample can be classified as being contaminated by live microorganisms.

In some cases, to determine whether a sample contains live or dead microbial contamination, the probe nucleic acid can be designed to detect microbial ribosomal RNA (e.g., microbial 16S rRNA) as the target nucleic acid. The amounts of ribosomal RNA can be very high in growing microbial cells and can be at least an order of magnitude higher than those of genomic microbial DNA. In addition, the presence of microbial rRNA can indicate the presence of live microorganisms since RNA typically degrades quickly (e.g., within minutes of cell death). In some cases, the methods described herein can be performed using probe nucleic acid designed to hybridize to an rRNA target nucleic acid and recognition endonucleases designed to cleave DNA:rRNA hybrids. When assessing samples for RNA target nucleic acid, the sample can be collected, used, or stored in a manner to preserve RNA from degradation. For example, a sample can be placed or maintained in an Ambion® RNAlater® solution.

In some cases, the sample being tested can be treated with a reverse transcriptase to produce cDNA from any RNA present within the sample. In such cases, the methods described herein can be performed using probe nucleic acid designed to hybridize to the produced cDNA if present within the sample. When assessing samples for RNA and using reverse transcriptase to produce cDNA target nucleic acid, the sample can be processed such that the sample contains RNA at a relatively high degree of purity. If a sample is found to contain microbial rRNA at a level above that observed in samples lacking live microorganisms, then the sample can be classified as being contaminated by live microorganisms.

In some cases, to determine whether a sample contains live or dead microbial contamination, the methods and materials provided herein can be used in combination with techniques designed to assess oxygen consumption such as those described elsewhere (e.g., O'Mahony and Papkovsky, *Applied and Environmental Microbiology*, 72:1279-1287 (2006) and O'Mahony et al., *Food Control*, 20:129-135 (2009)). For example, a portion of a sample can be subjected to culturing techniques using continuous (near real-time) fluorescent detection of oxygen consumption to assess the presence of growing cells. This can allow for a quick detection of microbial growth at early stages. The same portion or another portion of the sample can be assessed as described herein to determine whether the sample contains a target nucleic acid of a particular microorganism. The presence of active growing cells and the detection of the microbial target nucleic acid can indicate that the sample is contaminated by live microorganisms.

The invention will be further described in the following examples, which do not limit the scope of the invention described in the claims.

EXAMPLES

Example 1

Formation and Cleavage of Target-Probe Hybrids

An oligonucleotide probe (5'-thiol-GGT AGT GCG AAA TGC CAT TGC TAG TTG TTT-biotin-3'; SEQ ID NO:1) that was modified with a thiol group at the 5' end and a biotin molecule at the 3' end was conjugated to horseradish peroxidase (HRP). Conjugation was performed using the SMCC reagent according to a technique modified from Dill et al. (*Biosensors and Bioelectronics*, 20:736-742 (2004)). The HRP conjugate solution was incubated with a streptavidin-coated ELISA plate to immobilize the HRP-oligonucleotide probe to the surface via a biotin-streptavidin interaction. The ELISA plate was then incubated with different concentrations of a target oligonucleotide (5'-AAA CAA CTA GCA ATG GCA TTT-3'; SEQ ID NO:2). The target oligonucleotide sequence was reverse-complementary to the probe sequence to form a double-stranded hybrid molecule. After washing, the plate was incubated in a solution containing the restriction endonuclease BfaI. BfaI specifically recognizes the sequence 5'-CTAG-3' and cleaves the double-stranded, target-probe hybrids to release the HRP-oligonucleotide into the reaction solution. After a two-hour incubation at 37° C., the reaction solution was transferred to a new ELISA plate. The cleaved HRP-oligonucleotide was contacted to 3,3',5,5'-tetramethyl benzidine (TMB) to form a colored reaction product.

Figure 6:
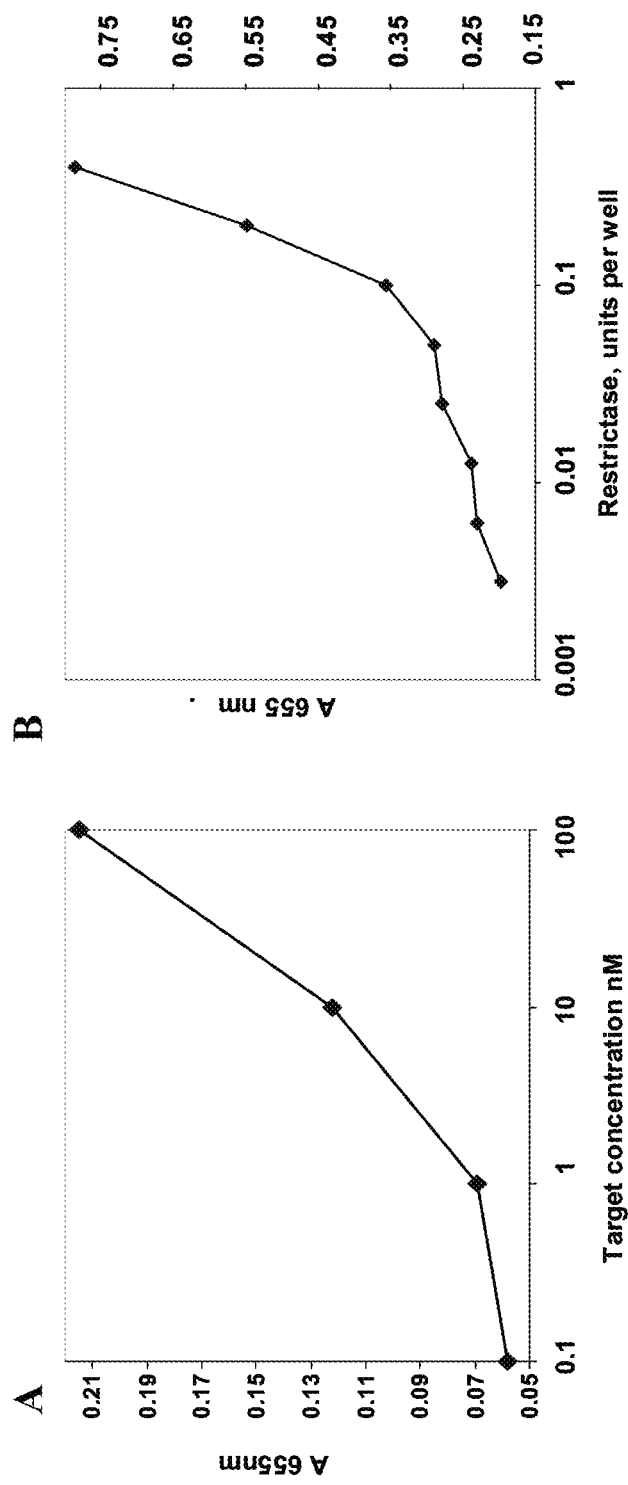
FIG. 6 contains line graphs demonstrating the effect of target oligonucleotide concentration (A) and recognition restriction endonuclease concentration (B) on the cleavage of HRP-labeled nucleic acid as detected by the formation of colored reaction product.

When the restriction endonuclease BfaI was added in excess to the reaction mixture, a clear direct dependence between the amount of released HRP-probe and the concentration of oligonucleotide target was observed (FIG. 6A). The detectable target concentration was approximately 1 nM. This detection limit was obtained by direct measurement without any secondary signal amplification. The addition of a restriction endonuclease signal amplification cascade as described herein can further improve the detection limit by several orders of magnitude.

When the HRP-oligonucleotide probes were pre-incubated with an excess of target oligonucleotide (500 nM), the amount of cleaved HRP-oligonucleotide probe was limited by the amount of recognition restriction endonuclease BfaI (FIG. 6B). Taken together, these data demonstrate that recognition restriction endonucleases can be used to initiate the restriction endonuclease cascades described herein.

Example 2

Detecting Target Nucleic Acid Using Probe Nucleic Acid and Reporter Nucleic Acid A target microorganism or virus suspected of contaminating a food product is selected, and a target nucleic acid of that selected target microorganism or virus is selected. Sequence alignments are used to locate conserved sequence regions such that a target nucleic acid is selected for which a number of different strains or variants of the target microorganism or virus can be detected. Other target nucleic acid sequences are selected and used to detect strains and variants that may not be detected using the selected conserved regions. Once selected, target nucleic acid is analyzed using a common genetic database such as GenBank® and/or a computer-based sequence analysis program to identify a portion of the target nucleic acid that contains a cut site for a restriction endonuclease. Probe nucleic acid is designed to be complementary to at least a portion of target nucleic acid that contains a cut site. Once designed and obtained by standard oligonucleotide synthesis methods, probe nucleic acid is conjugated to an amplifying restriction endonuclease and immobilized to the surface of a first well of a microtiter plate. A sample to be tested is incubated in the first well. If target nucleic acid is present in the sample, at least a portion of the target nucleic acid hybridizes to the probe nucleic acid, and thereby forms a recognition restriction endonuclease cut site. The recognition restriction endonuclease is added to the first well having the sample and probe nucleic acid. The microtiter plate is incubated at 37° C. for an appropriate length of time for the cleavage reaction to proceed.

Upon cleavage of probe nucleic acid by the recognition restriction endonuclease, the reaction solution containing the released portion of the probe nucleic acid is transferred into a second well. The second well contains reporter nucleic acid that is immobilized to the surface and contains at least one double-stranded portion having an amplifying restriction endonuclease cut site. Reporter nucleic acid also has a fluorescent label. Upon transfer to the second chamber, the amplifying restriction endonuclease bound to the released portion of the probe nucleic acid contacts the reporter nucleic acid. The amplifying restriction endonuclease cleaves reporter nucleic acid at the double-stranded amplifying restriction endonuclease cut site to form at least two portions. The liberated portion of the reporter nucleic acid having the fluorescent label is moved to a third microtiter plate well, and a standard fluorescent reader is used to measure any fluorescent signal.

A standard curve of known amounts of target nucleic acid is used to quantify the amount of target nucleic acid in the tested sample.

Example 3

Detecting Target Nucleic Acid Using Probe Nucleic Acid, First Signal Expansion Nucleic Acid, Second Signal Expansion Nucleic Acid, and Reporter Nucleic Acid A target microorganism or virus suspected of contaminating a food product is selected, and a target nucleic acid of that selected target microorganism or virus is selected. Sequence alignments are used to locate conserved sequence regions such that a target nucleic acid is selected for which a number of different strains or variants of the target microorganism or virus can be detected. Other target nucleic acid sequences are selected and used to detect strains and variants that may not be detected using the selected conserved regions. Once selected, target nucleic acid is analyzed using a common genetic database such as GenBank® and/or a computer-based sequence analysis program to identify a portion of target nucleic acid that contains a cut site for a restriction endonuclease. Probe nucleic acid is designed based on the desired target nucleic acid as described herein. Standard oligonucleotide synthesis methods are used to make the probe nucleic acid, which is then conjugated to an initial amplifying restriction endonuclease and immobilized to the surface of a first well of a microtiter plate. A sample to be tested for the target nucleic acid is incubated in the first well. If target nucleic acid is present in the sample, at least a portion of target nucleic acid hybridizes to probe nucleic acid and thereby forms a recognition restriction endonuclease cut site. Recognition restriction endonuclease is added to the first well having the sample and probe nucleic acid. The microtiter plate is incubated at 37° C. for an appropriate length of time for the cleavage reaction to proceed.

After cleavage of the probe nucleic acid:target nucleic acid hybrid by the recognition restriction endonuclease, the reaction solution containing the free portion of probe nucleic acid is transferred to another well that includes first signal expansion nucleic acid and second signal expansion nucleic acid. The first signal expansion nucleic acid and second signal expansion nucleic acid creates a positive feedback loop that causes an exponential acceleration of release of initial amplifying restriction enzymes. The reaction product from this well is transferred to another well containing reporter nucleic acid, and cleavage of the reporter nucleic acid is used to determine the presence, absence, or amount of target nucleic acid in the sample. A standard curve of known amounts of target nucleic acid is used to quantify the amount of target nucleic acid in the tested sample.

Example 4

Detecting the Presence or Absence of O157:H7 *E. coli* in Beef

The presence or absence of O157:H7 *E. coli* in a beef sample is detected using an enzymatic amplification cascade. An O157:H7 *E. coli* nucleic acid (GenBank® Accession No. BA000007; GenBank® GI No. 15829254) was analyzed using the GenBank® genetic database and CLC DNA Workbench software to identify a portion of target O157:H7 *E. coli* nucleic acid that contains Shiga toxin 2 subunit B gene (GenBank® GI No. 15829254 at 1267936-1268205) with a cut site for the DdeI restriction endonuclease, which cleaves at the 5 bp nucleotide sequence 5'-CTCAG-3'. A 40 nt probe nucleic acid (5'-ACAGTCATTCCTGTCAACTGAG-CACTTTGCAGTA-ACGGTT-3'; SEQ ID NO:3) was designed from positions 1269071 to 1269110 of the selected target nucleic acid.

Once designed and obtained by standard oligonucleotide synthesis methods, probe nucleic acid is conjugated to an amplifying restriction endonuclease (e.g., NcoI) and immobilized to the surface of a first well of a microtiter plate. A beef sample (e.g., a pooled sample from 60 randomly selected samples for beef trimmings of a lot, e.g., a 2,000 pound bin or combo) to be tested is obtained, and the nucleic acid of that sample is incubated in the first well. If O157:H7 *E. coli* is present in the sample, at least a portion of the O157:H7 *E. coli* nucleic acid hybridizes to the probe nucleic acid and thereby forms a DdeI cut site. DdeI recognition restriction endonuclease, which is present within the first well or which is added to the first well, is allowed to cleave any formed recognition restriction endonuclease cut sites by incubating the microtiter plate at 37° C. for an appropriate length of time (e.g., 1 minute to 2 hours) for the cleavage reaction to proceed.

After cleavage of the probe nucleic acid:target nucleic acid hybrid by DdeI recognition restriction endonuclease, the reaction solution in the first well is transferred to a second well containing reporter nucleic acid that is immobilized to the surface of the second well and that has at least one double-stranded portion having an amplifying restriction endonuclease cut site. The reporter nucleic acid can be a double-stranded nucleic acid having a first strand (e.g., 5'-CATTGCTAGTTGTTT CCATGGGGTAGT-GCGAAATGC-3'; SEQ ID NO:4) and a second strand (e.g., 5'-GCATTTCGC-ACTACCCCATG-GAAACAACTAGCAATG-3'; SEQ ID NO:5). The reporter nucleic acid also has a fluorescent label. In some cases, first signal expansion nucleic acid and second signal expansion nucleic acid are used prior to the reporter nucleic acid step to increase the level of target nucleic acid detection. The first signal expansion nucleic acid and second signal expansion nucleic acid can include labels, in which case they can be used together with reporter nucleic acid or in place of reporter nucleic acid.

After transferring the reaction mixture to the second chamber, the amplifying restriction endonucleases of the released portions of probe nucleic acid contact reporter nucleic acid, and the microtiter plate is incubated at an appropriate temperature (e.g., at 37° C.) for an appropriate length of time (e.g., 1 minute to 2 hours) for the cleavage reaction to proceed. The amplifying restriction endonucleases cleave reporter nucleic acid at the double-stranded amplifying restriction endonuclease cut site to form at least two portions. The reaction solution of the second well is transferred to a third well for fluorescence detection using a fluorescent microtiter plate reader. Fluorescence in the third well is indicative of O157:H7 *E. coli* nucleic acid present in the sample.

Example 5

Detecting the Presence or Absence of *Salmonella enterica* in a Beef Product

The presence or absence of *Salmonella enterica* in a beef product sample is detected using an enzymatic amplification cascade. A *Salmonella enterica* nucleic acid (GenBank® Accession No. NC_003198; GenBank® GI No. 16758993) was analyzed using the GenBank® genetic database and CLC DNA Workbench software to identify a portion of target *Salmonella enterica* nucleic acid that contains invasin A gene (GenBank® GI No. 16758993:c2892457-2890400) with a cut site for the RsaI restriction endonuclease, which cleaves at the 4 bp nucleotide sequence 5'-GTAC-3'. A 40 nt probe nucleic acid (5'-GCTGGCTTTCCCTTTCCAGTACGCT-TCGCCGTTCGCGC-3'; SEQ ID NO:6) was designed from positions 2890889 to 2890928 of the selected target nucleic acid.

Once designed and obtained by standard oligonucleotide synthesis methods, probe nucleic acid is conjugated to an amplifying restriction endonuclease NcoI and immobilized to the surface of a first well of a microtiter plate. A beef product sample (e.g., a pooled sample from 60 randomly selected samples for beef trimmings of a lot, e.g., a 2,000 pound bin or combo) to be tested is obtained, and the nucleic acid of that sample is incubated in the first well. If *Salmonella enterica* is present in the sample, at least a portion of the *Salmonella enterica* nucleic acid hybridizes to the probe nucleic acid and thereby forms a RsaI recognition restriction endonuclease cut site. RsaI recognition restriction endonuclease, which is present within the first well or which is added to the first well, is allowed to cleave any formed recognition restriction endonuclease cut sites by incubating the microtiter plate at 37° C. for an appropriate length of time (e.g., 1 minute to 2 hours) for the cleavage reaction to proceed.

After cleavage of the probe nucleic acid:target nucleic acid hybrid by RsaI, the reaction solution in the first well is transferred to a second well containing reporter nucleic acid that is immobilized to the surface of the second well and that has at least one double-stranded portion having an amplifying restriction endonuclease cut site. The reporter nucleic acid can be a double-stranded nucleic acid having a first strand (e.g., 5'-CATTGCTAGTTGTTTCCATGGGGTAGT-GCGAAATGC-3'; SEQ ID NO:4) and a second strand (e.g., 5'-GCATTTCGCACTACCCCATGGAAACAAC-TAGCAATG-3'; SEQ ID NO:5). The reporter nucleic acid also has a fluorescent label. In some cases, first signal expansion nucleic acid and second signal expansion nucleic acid are used prior to the reporter nucleic acid step to increase the level of target nucleic acid detection. The first signal expansion nucleic acid and second signal expansion nucleic acid can include labels, in which case they can be used together with reporter nucleic acid or in place of reporter nucleic acid.

After transferring the reaction mixture to the second chamber, the amplifying restriction endonucleases of the released portions of probe nucleic acid contact reporter nucleic acid, and the microtiter plate is incubated at an appropriate temperature (e.g., at 37° C.) for an appropriate length of time (e.g., 1 minute to 2 hours) for the cleavage reaction to proceed. The amplifying restriction endonucleases cleave reporter nucleic acid at the double-stranded amplifying restriction endonuclease cut site to form at least two portions. The reaction solution of the second well is transferred to a third well for fluorescence detection using a fluorescent microtiter plate reader. Fluorescence in the third well is indicative of *Salmonella enterica* nucleic acid present in the sample.

Example 6

Detecting the Presence or Absence of *Listeria monocytogenes* in a Beef Product

The presence or absence of *Listeria monocytogenes* in a beef product sample is detected using an enzymatic amplification cascade. A *Listeria monocytogenes* nucleic acid (GenBank® Accession No. NC_003210; GenBank® GI No. 16802048) was analyzed using the GenBank® genetic database and CLC DNA Workbench software to identify a portion of target *Listeria monocytogenes* nucleic acid that contains phosphoribosyl pyrophosphate synthetase gene (GenBank® GI No. 16802048:202641-203597) with a cut site for the HinfI restriction endonuclease, which cleaves at the 5 bp nucleotide sequence 5'-GANTC-3'. A 40 nt probe nucleic acid (5'-CTATGAAACGTATTGAAGAATCG-CCAATC-GAAAAATTAGT-3'; SEQ ID NO:7) was designed to be complementary to nucleotides 203105 to 203144 of the selected target nucleic acid.

Once designed and obtained by standard oligonucleotide synthesis methods, probe nucleic acid is conjugated to an amplifying restriction endonuclease and immobilized to the surface of a first well of a microtiter plate. A beef product sample (e.g., a pooled sample from 60 randomly selected samples for beef trimmings of a lot, e.g., a 2,000 pound bin or combo) to be tested is obtained, and the nucleic acid of that sample is incubated in the first well. If *Listeria monocytogenes* is present in the sample, at least a portion of the *Listeria monocytogenes* nucleic acid hybridizes to the probe nucleic acid and thereby forms a HinfI recognition restriction endonuclease cut site. HinfI recognition restriction endonuclease, which is present within the first well or which is added to the first well, is allowed to cleave any formed recognition restriction endonuclease cut sites by incubating the microtiter plate at 37° C. for an appropriate length of time (e.g., 1 minute to 2 hours) for the cleavage reaction to proceed.

After cleavage of the probe nucleic acid:target nucleic acid hybrid by HinfI, the reaction solution in the first well is transferred to a second well containing reporter nucleic acid that is immobilized to the surface of the second well and that has at least one double-stranded portion having an amplifying restriction endonuclease NcoI cut site. The reporter nucleic acid can be a double-stranded nucleic acid having a first strand (e.g., 5'-CATTGCTAGTTGTTTCCATGGGGTAGT-GCGAAATGC-3'; SEQ ID NO:4) and a second strand (e.g., 5'-GCATTTCGCACTACCCCATGGAAACAAC-TAGCAATG-3'; SEQ ID NO:5). The reporter nucleic acid also has a fluorescent label. In some cases, first signal expansion nucleic acid and second signal expansion nucleic acid are used prior to the reporter nucleic acid step to increase the level of target nucleic acid detection. The first signal expansion nucleic acid and second signal expansion nucleic acid can include labels, in which case they can be used together with reporter nucleic acid or in place of reporter nucleic acid.

After transferring the reaction mixture to the second chamber, the amplifying restriction endonucleases of the released portions of probe nucleic acid contact reporter nucleic acid, and the microtiter plate is incubated at an appropriate temperature (e.g., at 37° C.) for an appropriate length of time (e.g., 1 minute to 2 hours) for the cleavage reaction to proceed. The amplifying restriction endonucleases cleave reporter nucleic acid at the double-stranded amplifying restriction endonuclease cut site to form at least two portions. The reaction solution of the second well is transferred to a third well for fluorescence detection using a fluorescent microtiter plate reader. Fluorescence in the third well is indicative of *Listeria monocytogenes* nucleic acid present in the sample.

Example 7

Detecting the Presence or Absence of any of a Plurality of *E. coli* Strains

Publicly available information regarding gene sets and PCR primers for common pathogens was used to develop probe nucleic acid for use in an enzymatic amplification cascade method for detecting *E. coli*. *E. coli* strains are generally genetically heterogeneous, and some *E. coli* strains share only 40% genomic sequence identity. The general probe design process therefore was based on Multi Locus Sequence Typing genes (MLST; online at "mist" dot "net"). Seven such genes are used for *E. coli* genotyping. One of these, adenylate kinase (adk), was used to develop an enzymatic cascade assay for detecting the presence of *E. coli*.

Figure 9:
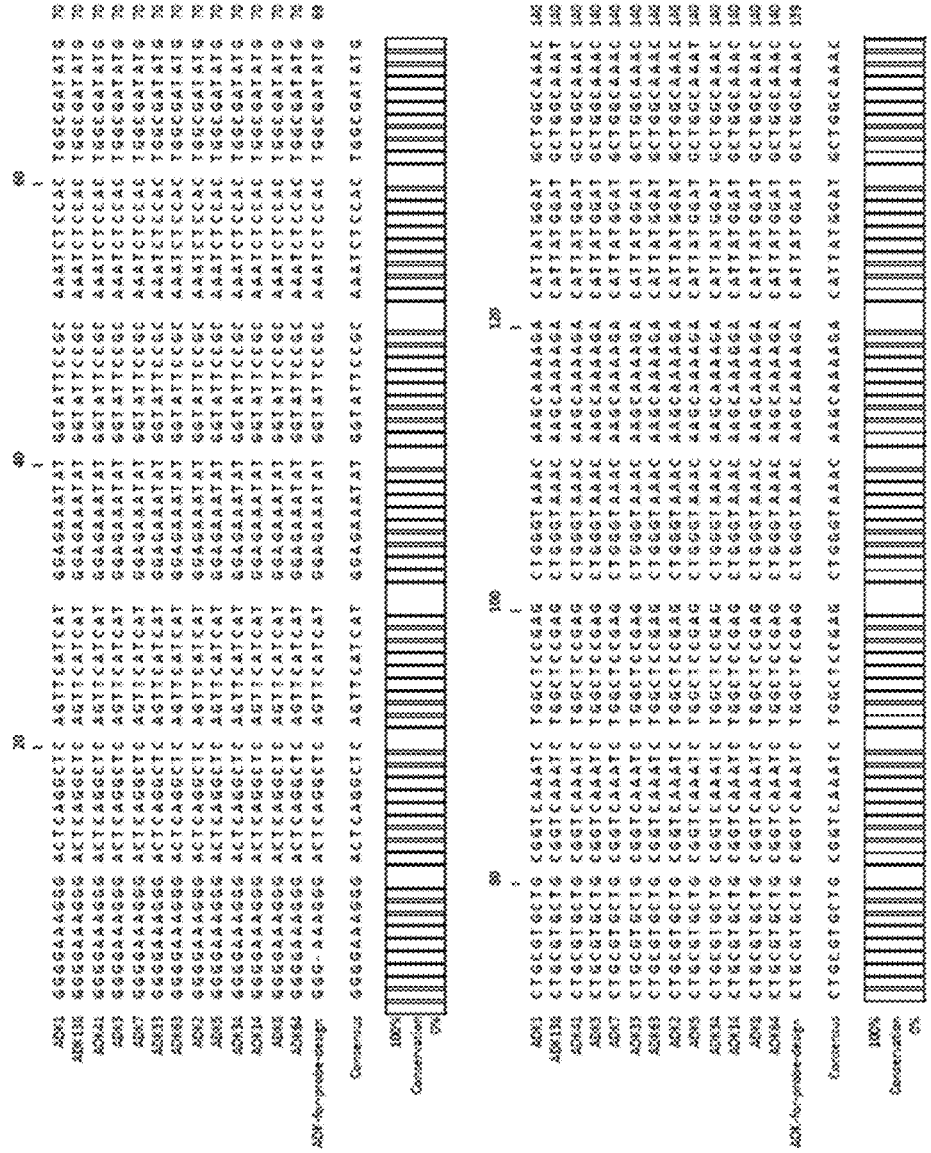
FIG. 9 is a diagram showing a sequence alignment of *E. coli* adk alleles. The sequence labeled ADK-for-probe-design is set forth in SEQ ID NO:28. The sequences labeled ADK138 and ADK5 are set forth in SEQ ID NO:29. The sequence labeled ADK14 is set forth in SEQ ID NO:30. The remaining sequences are set forth in SEQ ID NO:27.
Figure 10:
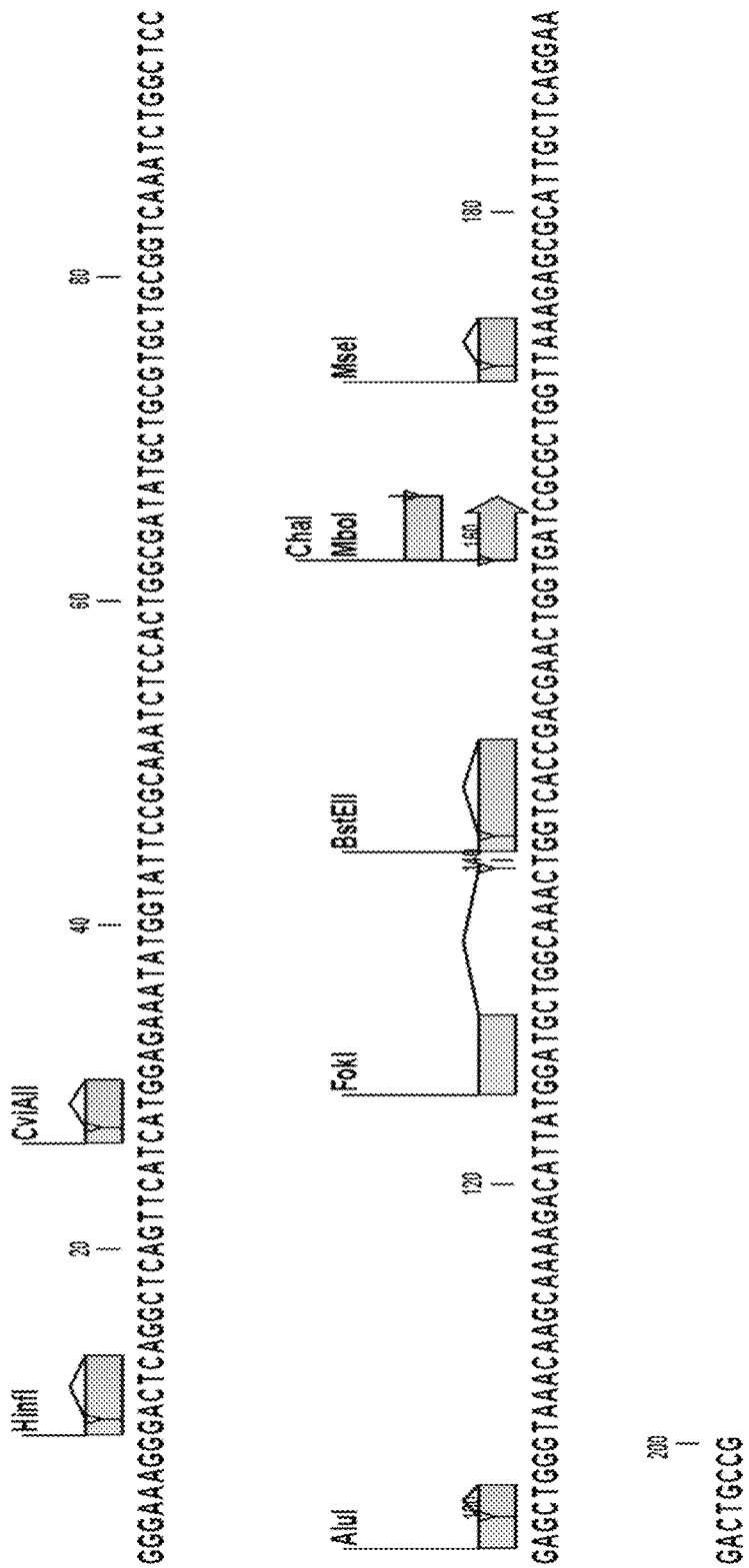
FIG. 10 is a diagram of a restriction map of the conserved adk sequence (SEQ ID NO:31) common for a majority of *E. coli* adk alleles.

An alignment of sequences from different alleles of the *E. coli* adk gene (FIG. 9) demonstrated that the first 200 nucleotides of these sequences are very conserved across 170 currently known alleles. The consensus sequence of this conserved adk region was selected for restriction endonuclease mapping, as shown in FIG. 10.

From the map, FokI was selected as the recognition restriction endonuclease. FokI has a 5 bp recognition sequence (GGATG) that is conserved in all adk allelic variants. A 40-mer probe nucleic acid having the FokI restriction site roughly in the middle of the sequence was selected to cover the currently known adk allelic variants (Table 2). The probe nucleic acid is used to detect the presence of the majority of *E. coli* strains. In a similar fashion, other MLST genes are used for probe nucleic acid design. If necessary, the probe nucleic acids are selected to distinguish among allelic variants of MLST genes.

Probe nucleic acids also were designed to distinguish between pathogenic enterohaemorrhagic (EHEC) and enteropathogenic (EPEC) isolates and common commensal *E. coli* strains. EHEC and EPEC isolates typically produce one or two types of Shiga toxins (indicators of severe clinical outcomes in infected patients), and also carry a genomic island known as the locus of enterocyte effacement (LEE). The LEE carries genes encoding, for example, intimin, which serves as an indicator of bacterial function. Shiga toxins encoded by STEC and EHEC belong to two families known as Stx1 and Stx2. The sequences of all known alleles of Stx1 and Stx2 genes were aligned, and genetically conserved regions at the 5' ends were selected. A search was conducted for restriction endonuclease cut sites that were common in the majority of alleles. The major criteria for recognition restriction endonuclease selection were (i) only one restriction site within the sequence of interest; (ii) a recognition sequence of at least 4-5 bases in length and having reasonably high sequence complexity; and (iii) no sequence overlaps with preselected common amplification restriction endonucleases. As above, a set of probe nucleic acids was then designed using sequences flanking the selected restriction endonuclease cut site, so that the cut site was roughly in the center of a 40-mer oligonucleotide. Typically, several probe nucleic acids were designed for each target gene in order to cover all allelic variation. For example, to detect Stx1 and Stx2, sets of 2 and 4 probe nucleic acids (corresponding to one or two recognition restriction endonucleases), respectively, were designed. Finally, all designed probes were used in BLAST searches to ensure their specificity to the corresponding target sequences.

In a similar fashion, probe nucleic acids were developed to detect the intimin (Eae) and alpha-hemolysin (hlyA) gene sequences as target nucleic acid (Table 2), which gene sequences have been used to detect pathogenic *E. coli* using other techniques (Zhang et al., *J. Clin. Microbiol.*, 40:4486-92 (2002)).

TABLE 2

Genes, probe nucleic acids, and recognition restriction endonucleases for the development of enzymatic amplification cascades of restriction endonucleases for detecting food pathogens.

| Pathogen | Gene name | Allele | Recognition restriction endonuclease | Probe nucleic acid (SEQ ID NO:) |
|---|---|---|---|---|
| E. coli, all | adk (adenylate kinase) | majority of 170 alleles | FokI (ggatg) | GCAAAAGACATTATGGATGCTGG CAAACTGGTCACCGACG (8) |
| | | adk5, 52, 90, 126 | FokI (ggatg) | GCAAAAGACATTATGGATGCTGG CAAATTGGTCACCGACG (9) |
| EHEC | Shiga toxin stx1 | stx1, 1-O48, 1-CB168 | HinfI (gantc) | GAGAAGAAGAGACTGAAGATTCC ATCTGTTGGTAAATAAT (10) |
| | stx1 | stx1c, 1d | HinfI (gantc) | GAGAAGAAGAGACTGAAGATTCC ATCTGTTAGTAAATAAT (11) |
| EPEC | Shiga toxin stx2 | stx2b, 2v-hac | DdeI (ctgag) | ACAGTCATTCCTGTCAACTGAGC ACTTTGCAGTAACGGTT (12) |
| | | stx2v-hbd | DdeI (ctgag) | ACAGTCATTCCTGTCAGCTGAGC ACTTTGCAGTAACGGTT (13) |
| | | stx2ge | HpaI (gttaac) | TTGTTACGGTCATTCCTGTTAAC TGTGCACTTTGTAACAA (14) |
| | | stx2-NV206f, EC1586g | HpaI (gttaac) | TTGTGACTGTCATTCCTGTTAAC TGTGCACTTTGCAGTAG (15) |
| | intimins (eae genes) | intimins β, γ2, ε | PstI (ctgcag) | TCAAAGTTATTACCACTCTGCAG ATTAACCTCTGCCGTTC (16) |
| | | intimin γ1 | PstI (ctgcag) | TCAAAGTTATCACCACTCTGCAG ATTAACCTCTGCCGTTC (17) |
| | α-hemolysin (hlyA) | hlyA | HpaI (gttaac) | AATTTCCTCACCGGGAGTTAACA ATGGCGTAACAAATTTC (18) |
| S. enterica strains | invA (invasin A) | 8 alleles | RsaI (gtac) | GCTGGCTTTCCCTTTCCAGTACG CTTCGCCGTTCGCGC (19) |
| Listeria monocytogenes | prs (P-ribosyl pyro-PP synthase) | 3 alleles | HinfI (gantc) | CTATGAAACGTATTGAAGAATCG CCAATCGAAAAATTAGT (20) |
| Thermophylic Campylobacter | 16S rRNA | 33 alleles | MseI (ttaa) | TTCCCTACTCAACTTGTGTTAAG CAGGAGTATAGAGTATT (21) |
| Vibrio parahaemolyticus | VP1316 (LysR transcription reg) | 1 allele | EcoRV (gatatc) | GCTCAATGGACAACTCGATATCG GAGTGATCAGCTGTGAC (22) |

An assay for pathogenic E. coli can include multiple probe nucleic acids and recognition restriction endonucleases to distinguish the pathogenic E. coli from common commensal E. coli strains. The assay scheme can be simplified if the goal is to detect all strains/species from a group/genus, which is the case for Campylobacter, where a PCR-based assay has been used for a specific fragment of 16S rRNA conserved in this genus (Perelle et al., Mol. Cell. Probes, 18:321-327 (2004)). In a similar fashion, an enzymatic amplification cascade-based assay was designed by selecting a conserved restriction site within this sequence and creating a set of probe nucleic acids using flanking sequences to cover the allelic variation within the Campylobacter genus (Table 2).

Pathogenic Salmonella strains can carry alleles of invA (invasin A) in their genomes. Corresponding probe nucleic acids and recognition restriction endonucleases were developed for all eight Salmonella invA allelic variants (Table 2). In addition, an enzymatic amplification cascade assay was developed for the Listeria monocytogenes prs gene, which encodes phoshoribosyl pyrophosphate synthetase (Jin et al., Appl. Environ. Microbiol., 75:6647-54 (2009)). Further, probe nucleic acid and recognition restriction endonucleases were designed for the common waterborne and seafood pathogen Vibrio parahaemolyticus, using the VP1316 (LysR transcription reg) gene (Table 2).

The selected recognition restriction endonucleases do not require chemical modification or additional purification, are available commercially, are used directly for enzymatic amplification cascade assays, and are specific to the designed probe nucleic acid. In contrast, the same amplification restriction endonuclease can be attached to different probe nucleic acids, and they are modified to be conjugated to the probe nucleic acids via linkers. A possible criterion for selection of amplification restriction endonucleases is a unique sequence recognition site that does not overlap with sites specific for recognition restriction endonucleases. One way to fulfill this criterion is to select a restriction endonuclease with a cut site that has a very low probability of being encountered in the target of interest. In this regard, NcoI, with the 6-base long restriction site C/CATGG, is useful as an amplification restriction endonuclease. NcoI maintains 100% of its activity in all major restriction buffer solutions, including NEBuffers 1, 2, 3, and 4 (New England Biolabs; Ipswich, Mass.), providing for reaction conditions compatible with a large variety of other restriction endonucleases.

A 36 nt reporter nucleic acid for attachment of label molecule M was designed to include a central NcoI restriction cut site (underlined): 5'-CATTGCTAGTTGTTT CCATGGGGTAGTG CGAAATGC-3' (SEQ ID NO:4). The NcoI amplification restriction endonuclease is coupled to thiol-modified oligonucleotide probes using conjugation performed with succinimidyl 4-[N-maleimidomethyl]cyclohexane-1-carboxylate reagent as described elsewhere (Dill et al., *Biosens. Bioelectron.*, 20:736-742 (2004)). To ensure conjugate quality, commercially obtained NcoI is purified using ion exchange and gel filtration chromatography.

The probe nucleic acid and reporter nucleic acid are attached to a solid surface of a slide, plate (e.g., the well of a 96-well microtiter plate), bead, or film using a biotin-streptavidin technique in which the probe nucleic acid and reporter nucleic acid contain biotin and are attached to a solid support coated with streptavidin. The probe nucleic acid and reporter nucleic acid are attached to a solid surface a manner such that the amplification restriction endonucleases of the probe nucleic acid do not cleave the reporter nucleic acid at the amplification restriction endonuclease cut site until an amplification restriction endonuclease of the probe nucleic acid is released via cleavage of the probe nucleic acid at the recognition restriction endonuclease cut site of the probe nucleic acid.

A beef product sample is collected and homogenized. One portion of the beef product sample is processed by direct preparation of potential DNA targets, while another portion of the beef product sample is cultured with nutrient medium for 2-6 hours prior to being processed for preparation of potential DNA targets. To determine whether detected bacteria are dead or alive, the results from each portion are compared. A significant signal increase or appearance of positive results in the cultured sample indicates the presence of live bacterial pathogens.

Prior to performing the enzymatic amplification cascade of restriction endonucleases, the samples to be tested are treated to disrupt the cells, including bacteria, present within the sample. Disruption can be achieved by (1) high speed mechanical disruption with glass, silica, zirconium, or stainless steel beads, (2) high temperature (e.g., boiling or autoclaving), (3) chemical lysis with detergents, (4) repetitive freeze-thaw cycles (e.g., using liquid nitrogen or dry ice), (5) sonication, or (6) any combination thereof. The sample is subjected to total DNA extraction.

The samples containing extracted DNA are used for enzymatic amplification cascade of restriction endonucleases-based detection of *E. coli*, or the degree of purification of the extracted DNA in the sample can be adjusted according to further analytical steps. In such cases, the samples are subjected to quick (1 hour) PCR-based amplification of specific pathogen targets, or for whole genome amplification (e.g., with Qiagen REPLI-g Screening Kit for high-throughput manual or automated whole genome amplification; Qiagen, Valencia, Calif.). Such approaches are used with samples of limited size, or to increase assay sensitivity. Purifying DNA in the sample to a relatively high degree removes potential inhibitors of DNA polymerases used for PCR-based amplification.

When a sample is applied to an enzymatic amplification cascade of restriction endonucleases assay with no PCR-based amplification involved, the DNA within the sample is fragmented into shorter sequences. This is achieved using restriction endonuclease digestion with DpnII or CviJI, which frequently are applied for this purpose, or using sonication techniques.

The samples are provided with a buffer compatible with the corresponding recognition restriction endonuclease. Prior to detection, double stranded DNA within a sample is separated into single strands by heating and snap-cooling or by chemical denaturation. Alternatively, when DNA targets fragments within the sample are generated by PCR, certain primer or reaction modifications are used to generate preferentially single-stranded product. These include (i) unidirectional DNA polymerase reaction with a single specific primer, (ii) separation of strands of double-stranded PCR products, and enrichment of the strand of interest using specific biotinylated primers and streptavidin-conjugated magnetic beads, and (iii) selective digestion of one strand with lambda exonuclease. Selection of the appropriate technique depends on the assay goals and required sensitivity. In some cases, detection of the target strand of interest can achieve increased sensitivity or detection limits in the absence of a complementary second strand. The exponential effects of an enzymatic amplification cascade of restriction endonucleases assay can, however, achieve very high signal intensities based on a small number of hybridization and recognition events. Such assays likely do not require complete strand separation or a very high degree of DNA purification, especially if the DNA is applied in a semi-quantitative way to produce quick 'yes/no' answers or simple colored reactions for visual estimation.

In some cases (e.g., when it is desired to detect live microbes), samples are collected and processed for detecting target RNA instead of target DNA. For example, 16S rRNA gene sequences or an internal transcribed spacer of an rRNA gene cassette can be used as the target nucleic acid. After the samples are processed to contain extracted rRNA, single stranded targets are prepared using reverse transcription to convert total RNA into cDNA. Since cDNA is single-stranded, it is applied directly to the probe nucleic acid(s) for assay. For RNA-based assays, samples are collected and carefully stored (e.g., in Ambion RNAlater solution; Ambion, Austin, Tex.) so as to preserve RNA from degradation. In addition, RNA of the sample is in a relatively high degree of purity since reverse transcriptases can be sensitive to contamination.

The following outlines the steps in an exemplary enzymatic amplification cascade of restriction endonucleases for detecting EHEC and EPEC *E. coli* in beef 1. Sterile sponge swabs are used to collect potential bacteria from the surface of cut meat. For ground beef, 60 randomly selected 15 g samples are collected and pooled into a 900 g sample of which a 375 g sample is obtained.
2. For each sample, half of the collected material is applied for pre-cultivation in a liquid nutrient medium, such as Tryptic soy broth b (TSBb), at 37° C. for 2-6 hours.
3. All samples, enriched by pre-culturing and non-enriched, are subjected to total DNA isolation using Qiagen BioSprint 96 One-For-All Vet Kit.
4. One aliquot of each sample is applied for PCR-based amplification of *E. coli* adk, stx, hlyA, and eae genes. This amplification is done using modified primers to selectively enrich for the single-stranded targets. The resultant samples containing amplicons, after strand separation, are directly applied to an enzymatic amplification cascade of restriction endonucleases as described herein.
5. Another aliquot of each sample is subjected to DNA fragmentation and double-strand separation. The resultant samples are applied to an enzymatic amplification cascade of restriction endonucleases as described herein.
6. Comparison of the results obtained for each sample, and between enriched and non-enriched samples, provides sufficient information to make conclusions about the presence and relative amount of live bacteria in the samples. To make the analyses more quantitative (rather than 'yes-no' type), standard, specifically contaminated beef samples (or bacterial cultures) are included in the assays.

Example 8

Detecting the Presence or Absence of *Staphylococcus aureus* in a Poultry Product The presence or absence of *Staphylococcus aureus* in a poultry product sample is detected using an enzymatic amplification cascade. A *Staphylococcus aureus* nucleic acid (GenBank® Accession No. NC_013450; GenBank® GI No. 269201690) was analyzed using the GenBank® genetic database and CLC DNA Workbench software to identify a portion of target *Staphylococcus aureus* nucleic acid that contains the DNA gyrase subunit B gene (GenBank® GI No. 269201690: 5034-6968) with a cut site for the EcoRV restriction endonuclease, which cleaves at the 6 bp nucleotide sequence 5'-GATATC-3'. A 40 nt probe nucleic acid (5'-TGAT-CTAGCGAAAGCAAGATATCA-CAAAATCGTCATTATG-3'; SEQ ID NO:23) was designed to be complementary to nucleotides 5340 to 5389 of the selected target nucleic acid.

Once designed and obtained by standard oligonucleotide synthesis methods, probe nucleic acid is conjugated to an amplifying restriction endonuclease and immobilized to the surface of a first well of a microtiter plate. A poultry product sample to be tested is obtained, and the nucleic acid of that sample is incubated in the first well. If *Staphylococcus aureus* is present in the sample, at least a portion of the *Staphylococcus aureus* nucleic acid hybridizes to the probe nucleic acid and thereby forms a EcoRV site. EcoRV recognition restriction endonuclease, which is present within the first well or which is added to the first well, is allowed to cleave any formed recognition restriction endonuclease cut sites by incubating the microtiter plate at 37° C. for an appropriate length of time (e.g., 1 minute to 2 hours) for the cleavage reaction to proceed.

After cleavage of the probe nucleic acid:target nucleic acid hybrid by EcoRV, the reaction solution in the first well is transferred to a second well containing reporter nucleic acid that is immobilized to the surface of the second well and that has at least one double-stranded portion having an amplifying restriction endonuclease NcoI cut site. The reporter nucleic acid can be a double-stranded nucleic acid having a first strand (e.g., 5'-CATTGCTAGTTGT-TT CCATGGGGTAGTGCGAAATGC-3'; SEQ ID NO:4) and a second strand (e.g., 5'-GCATTTCGCACTACCCCATG-GAAACAACTAGCAATG-3'; SEQ ID NO:5). The reporter nucleic acid also has a fluorescent label. In some cases, first signal expansion nucleic acid and second signal expansion nucleic acid are used prior to the reporter nucleic acid step to increase the level of target nucleic acid detection. The first signal expansion nucleic acid and second signal expansion nucleic acid can include labels, in which case they can be used together with reporter nucleic acid or in place of reporter nucleic acid.

After transferring the reaction mixture to the second chamber, the amplifying restriction endonucleases of the released portions of probe nucleic acid contact reporter nucleic acid, and the microtiter plate is incubated at an appropriate temperature (e.g., at 37° C.) for an appropriate length of time (e.g., 1 minute to 2 hours) for the cleavage reaction to proceed. The amplifying restriction endonucleases cleave reporter nucleic acid at the double-stranded amplifying restriction endonuclease cut site to form at least two portions. The reaction solution of the second well is transferred to a third well for fluorescence detection using a fluorescent microtiter plate reader. Fluorescence in the third well is indicative of *Staphylococcus aureus* nucleic acid present in the sample.

Example 9

Detecting the Presence or Absence of *Campylobacter jejuni* in a Poultry Product The presence or absence of *Campylobacter jejuni* in a poultry product sample is detected using an enzymatic amplification cascade. A *Campylobacter jejuni* target nucleic acid (GenBank® Accession No. NC_003912; GenBank® GI No. 57236892) was analyzed using the GenBank® genetic database and CLC DNA Workbench software to identify a portion of target *Campylobacter jejuni* nucleic acid that contains 16S rRNA processing protein RimM gene (GenBank® GI No. 57236892:746394-746933) with a cut site for the EcoRV restriction endonuclease, which cleaves at the 6 bp nucleotide sequence 5'-GATATC-3'. A 40 nt probe nucleic acid (5'-AG-ATTAGGTAAAGTGGTTGATATCTTG-GAAACTGGAGCTT-3'; SEQ ID NO:24) was designed to be complementary to nucleotides 746739 to 746778 of the selected target nucleic acid.

Once designed and obtained by standard oligonucleotide synthesis methods, probe nucleic acid is conjugated to an amplifying restriction endonuclease and immobilized to the surface of a first well of a microtiter plate. A poultry product sample to be tested is obtained, and the nucleic acid of that sample is incubated in the first well. If *Campylobacter jejuni* is present in the sample, at least a portion of the *Campylobacter jejuni* nucleic acid hybridizes to the probe nucleic acid and thereby forms a EcoRV recognition restriction endonuclease cut site. EcoRV recognition restriction endonuclease, which is present within the first well or which is added to the first well, is allowed to cleave any formed recognition restriction endonuclease cut sites by incubating the microtiter plate at 37° C. for an appropriate length of time (e.g., 1 minute to 2 hours) for the cleavage reaction to proceed.

After cleavage of the probe nucleic acid:target nucleic acid hybrid by EcoRV, the reaction solution in the first well is transferred to a second well containing reporter nucleic acid that is immobilized to the surface of the second well and that has at least one double-stranded portion having an amplifying restriction endonuclease NcoI cut site. The reporter nucleic acid can be a double-stranded nucleic acid having a first strand (e.g., 5'-CATTGCTAGTT-GTTT CCATGGGGTAGTGCGAAATGC-3'; SEQ ID NO:4) and a second strand (e.g., 5'-GCATTTCGCACTACCCCATG-GAAACAACTAGCAATG-3'; SEQ ID NO:5). The reporter nucleic acid also has a fluorescent label. In some cases, first signal expansion nucleic acid and second signal expansion nucleic acid are used prior to the reporter nucleic acid step to increase the level of target nucleic acid detection. The first signal expansion nucleic acid and second signal expansion nucleic acid can include labels, in which case they can be used together with reporter nucleic acid or in place of reporter nucleic acid.

After transferring the reaction mixture to the second chamber, the amplifying restriction endonucleases of the released portions of probe nucleic acid contact reporter nucleic acid, and the microtiter plate is incubated at an appropriate temperature (e.g., at 37° C.) for an appropriate length of time (e.g., 1 minute to 2 hours) for the cleavage reaction to proceed. The amplifying restriction endonucleases cleave reporter nucleic acid at the double-stranded amplifying restriction endonuclease cut site to form at least two portions. The reaction solution of the second well is transferred to a third well for fluorescence detection using a fluorescent microtiter plate reader. Fluorescence in the third well is indicative of *Campylobacter jejuni* nucleic acid present in the sample.

Example 10

Detecting the Presence or Absence of *Shigella dysenteriae* in a Vegetable Product The presence or absence of *Shigella dysenteriae* in a vegetable product sample is detected using an enzymatic amplification cascade. A *Shigella dysenteriae* nucleic acid (GenBank® Accession No. NC_007607; GenBank® GI No. 82524407) was analyzed using the GenBank® genetic database and CLC DNA Workbench software to identify a portion of target *Shigella dysenteriae* nucleic acid that contains an ipaH invasion plasmid antigen gene (GenBank® GI No. 82524407:110427-111971) with a cut site for the HindIII restriction endonuclease, which cleaves at the 6 bp nucleotide sequence 5'-AAGCTT-3'. A 40 nt probe nucleic acid (5'-TCCTCCG-GCAGAAGCAGAAAAAGCTTATTATGCT-TCCATC-3'; SEQ ID NO:25) was designed to be complementary to nucleotides 111909 to 111948 of the selected target nucleic acid.

Once designed and obtained by standard oligonucleotide synthesis methods, probe nucleic acid is conjugated to an amplifying restriction endonuclease and immobilized to the surface of a first well of a microtiter plate. A vegetable product sample to be tested is obtained, and the nucleic acid of that sample is incubated in the first well. If *Shigella dysenteriae* is present in the sample, at least a portion of the *Shigella dysenteriae* nucleic acid hybridizes to the probe nucleic acid and thereby forms a HindIII recognition restriction endonuclease cut site. HindIII recognition restriction endonuclease, which is present within the first well or which is added to the first well, is allowed to cleave any formed recognition restriction endonuclease cut sites by incubating the microtiter plate at 37° C. for an appropriate length of time (e.g., 1 minute to 2 hours) for the cleavage reaction to proceed.

After cleavage of the probe nucleic acid:target nucleic acid hybrid by HindIII, the reaction solution in the first well is transferred to a second well containing reporter nucleic acid that is immobilized to the surface of the second well and that has at least one double-stranded portion having an amplifying restriction endonuclease NcoI cut site. The reporter nucleic acid can be a double-stranded nucleic acid having a first strand (e.g., 5'-CATTGCTAGTT-GTTT CCATGGGGTAGTGCGAAATGC-3'; SEQ ID NO:4) and a second strand (e.g., 5'-GCATTTCGCACTACCCCATG-GAAACAACTAGCAATG-3'; SEQ ID NO:5). The reporter nucleic acid also has a fluorescent label. In some cases, first signal expansion nucleic acid and second signal expansion nucleic acid are used prior to the reporter nucleic acid step to increase the level of target nucleic acid detection. The first signal expansion nucleic acid and second signal expansion nucleic acid can include labels, in which case they can be used together with reporter nucleic acid or in place of reporter nucleic acid.

After transferring the reaction mixture to the second chamber, the amplifying restriction endonucleases of the released portions of probe nucleic acid contact reporter nucleic acid, and the microtiter plate is incubated at an appropriate temperature (e.g., at 37° C.) for an appropriate length of time (e.g., 1 minute to 2 hours) for the cleavage reaction to proceed. The amplifying restriction endonucleases cleave reporter nucleic acid at the double-stranded amplifying restriction endonuclease cut site to form at least two portions. The reaction solution of the second well is transferred to a third well for fluorescence detection using a fluorescent microtiter plate reader. Fluorescence in the third well is indicative of *Shigella dysenteriae* nucleic acid present in the sample.

Example 11

Detecting the Presence or Absence of *Vibrio parahaemolyticus* in a Seafood Product The presence or absence of *Vibrio parahaemolyticus* in a seafood product sample is detected using an enzymatic amplification cascade. A *Vibrio parahaemolyticus* target nucleic acid (GenBank® Accession No. NC_004603; GenBank® GI No. 28896774) was analyzed using the GenBank® genetic database and CLC DNA Workbench software to identify a portion of target *Vibrio parahaemolyticus* nucleic acid that contains phosphoribosyl pyrophosphate synthetase gene (GenBank® GI No. 28896774:1395987-1396856) with a cut site for the EcoRV restriction endonuclease, which cleaves at the 6 bp nucleotide sequence 5'-GATATC-3'. A 40 nt probe nucleic acid (5'-GCTCAATGGACAACTCGATATCG-GAGTGATCAGCTGTGAC-3'; SEQ ID NO:26) was designed from positions 1396222 to 1396261 of the selected target nucleic acid.

Once designed and obtained by standard oligonucleotide synthesis methods, probe nucleic acid is conjugated to an amplifying restriction endonuclease and immobilized to the surface of a first well of a microtiter plate. A seafood product sample to be tested is obtained, and the nucleic acid of that sample is incubated in the first well. If *Vibrio parahaemolyticus* is present in the sample, at least a portion of the *Vibrio parahaemolyticus* nucleic acid hybridizes to the probe nucleic acid and thereby forms an EcoRV recognition restriction endonuclease cut site. EcoRV recognition restriction endonuclease, which is present within the first well or which is added to the first well, is allowed to cleave any formed recognition restriction endonuclease cut sites by incubating the microtiter plate at 37° C. for an appropriate length of time (e.g., 1 minute to 2 hours) for the cleavage reaction to proceed.

After cleavage of the probe nucleic acid:target nucleic acid hybrid by EcoRV, the reaction solution in the first well is transferred to a second well containing reporter nucleic acid that is immobilized to the surface of the second well and that has at least one double-stranded portion having an amplifying restriction endonuclease NcoI cut site. The reporter nucleic acid can be a double-stranded nucleic acid having a first strand (e.g., 5'-CATTGCTAGTT-GTTT CCATGGGGTAGTGCGAAATGC-3'; SEQ ID NO:4) and a second strand (e.g., 5'-GCATTTCGCACTACCCCATG-GAAACAACTAGCAATG-3'; SEQ ID NO:5). The reporter nucleic acid also has a fluorescent label. In some cases, first signal expansion nucleic acid and second signal expansion nucleic acid are used prior to the reporter nucleic acid step to increase the level of target nucleic acid detection. The first signal expansion nucleic acid and second signal expansion nucleic acid can include labels, in which case they can be used together with reporter nucleic acid or in place of reporter nucleic acid.

After transferring the reaction mixture to the second chamber, the amplifying restriction endonucleases of the released portions of probe nucleic acid contact reporter nucleic acid, and the microtiter plate is incubated at an appropriate temperature (e.g., at 37° C.) for an appropriate length of time (e.g., 1 minute to 2 hours) for the cleavage reaction to pro ceed. The amplifying restriction endonucleases cleave reporter nucleic acid at the double-stranded amplifying restriction endonuclease cut site to form at least two portions. The reaction solution of the second well is transferred to a third well for fluorescence detection using a fluorescent microtiter plate reader. Fluorescence in the third well is indicative of *Vibrio parahaemolyticus* nucleic acid present in the sample.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for assessing a food product for contamination, said method comprising:
   (a) contacting a sample from said food product with a probe nucleic acid comprising a nucleotide sequence complementary to a sequence of a target nucleic acid present within a microorganism or virus under conditions wherein, if said target nucleic acid is present in said sample, at least a portion of said target nucleic acid hybridizes to at least a portion of said probe nucleic acid to form a double-stranded portion of nucleic acid comprising a restriction endonuclease cut site, wherein said probe nucleic acid comprises a restriction endonuclease,
   (b) contacting said double-stranded portion of nucleic acid with a recognition restriction endonuclease having the ability to cut said double-stranded portion of nucleic acid at said restriction endonuclease cut site under conditions wherein said recognition restriction endonuclease cleaves said double-stranded portion of nucleic acid at said restriction endonuclease cut site, thereby separating a portion of said probe nucleic acid comprising said restriction endonuclease from at least another portion of said probe nucleic acid,
   (c) contacting said portion of said probe nucleic acid comprising said restriction endonuclease with signal expansion nucleic acid comprising an amplifying restriction endonuclease, a label, and a double-stranded portion of nucleic acid comprising a restriction endonuclease cut site of said restriction endonuclease under conditions wherein said restriction endonuclease cleaves said signal expansion nucleic acid at said restriction endonuclease cut site of said restriction endonuclease, thereby separating a first portion of said signal expansion nucleic acid from at least another portion of said signal expansion nucleic acid, wherein said first portion comprises said label, and
   (d) detecting the presence or absence of said first portion using said label, wherein the presence of said first portion indicates that said sample contains said target nucleic acid and is thereby contaminated, and wherein the absence of said first portion indicates that said sample does not contain said target nucleic acid and is thereby not contaminated.

2. The method of claim 1, wherein said food product is selected from the group consisting of beef products, poultry products, pork products, and dairy products.

3. The method of claim 1, wherein said food product is ground beef or a beef trimming.

4. The method of claim 1, wherein said food product is milk.

5. The method of claim 1, wherein said food product is chicken meat.

6. The method of claim 1, wherein said sample comprises a food product sample obtained from said food product.

7. The method of claim 1, wherein said sample comprises a liquid rinse obtained from said food product.

8. The method of claim 1, wherein said sample comprises a pooled plurality of samples randomly obtained from said food product.

9. The method of claim 1, wherein, prior to step (a), said sample was cultured to enrich the population of microorganisms or viruses, if present, within said sample.

10. The method of claim 9, wherein said sample was cultured for at least 30 minutes in the presence of enrichment medium.

11. The method of claim 1, wherein, prior to step (a), said sample was processed to remove non-nucleic acid material from said sample, thereby increasing the concentration of nucleic acid, if present, within said sample.

12. The method of claim 1, wherein said probe nucleic acid is attached to a solid support.

13. The method of claim 1, wherein step (a) and step (b) are performed in the same compartment.

14. The method of claim 1, wherein step (a) and step (b) are performed by adding said sample to a compartment comprising said probe nucleic acid and said recognition restriction endonuclease.

15. The method of claim 1, wherein said label is a fluorescent label, a radioactive label, an enzyme label, or a redox label.

16. The method of claim 1, wherein said detecting step comprises quantifying the amount of said target nucleic acid present within said sample.

17. The method of claim 1, wherein said probe nucleic acid is single-stranded probe nucleic acid.

18. The method of claim 1, wherein said restriction endonuclease is an EcoRI endonuclease, and wherein said amplifying restriction endonuclease is an EcoRI endonuclease.

19. The method of claim 1, wherein said restriction endonuclease is a BamHI endonuclease, and wherein said amplifying restriction endonuclease is a BamHI endonuclease.

20. The method of claim 1, wherein said restriction endonuclease cut site of said restriction endonuclease is an EcoRI endonuclease cut site or a BamHI endonuclease cut site.

* * * * *